United States Patent
Suto et al.

(10) Patent No.: US 11,623,918 B2
(45) Date of Patent: Apr. 11, 2023

(54) COMPOUNDS FOR THE TREATMENT OF ACUTE AND CHRONIC KIDNEY DISEASE

(71) Applicants: Southern Research Institute, Birmingham, AL (US); UAB Research Foundation, Birmingham, AL (US); The United States Government as Represented by the Department of Veterans Affairs, Washington, DC (US)

(72) Inventors: Mark J. Suto, Homewood, AL (US); Bini Mathew, Hoover, AL (US); Anupam Agarwal, Mountain Brook, AL (US); Amie M. Traylor, Talladega, AL (US)

(73) Assignees: Southern Research Institute, Birmingham, AL (US); UAB Research Foundation, Birmingham, AL (US); The United States Government as Represented by the Department of Veterans Affairs, Washington, DC (US)

( * ) Notice: Subject to any disclaimer, the term of this patent is extended or adjusted under 35 U.S.C. 154(b) by 0 days.

(21) Appl. No.: 17/529,201

(22) Filed: Nov. 17, 2021

(65) Prior Publication Data
US 2022/0153702 A1    May 19, 2022

Related U.S. Application Data

(60) Provisional application No. 63/115,420, filed on Nov. 18, 2020.

(51) Int. Cl.
| C07D 215/36 | (2006.01) |
| C07D 215/40 | (2006.01) |
| C07D 215/48 | (2006.01) |
| C07D 213/70 | (2006.01) |
| C07D 217/22 | (2006.01) |
| C07C 321/28 | (2006.01) |

(52) U.S. Cl.
CPC .......... C07D 215/36 (2013.01); C07C 321/28 (2013.01); C07D 213/70 (2013.01); C07D 215/40 (2013.01); C07D 215/48 (2013.01); C07D 217/22 (2013.01)

(58) Field of Classification Search
CPC .. C07D 215/36; C07D 215/40; C07D 215/48; C07D 213/70; C07D 217/22; C07C 321/28
See application file for complete search history.

(56) References Cited

U.S. PATENT DOCUMENTS

| 8,642,660 B2 * | 2/2014 | Goldfarb .............. A61K 31/122 514/18.9 |
| 10,766,888 B1 | 9/2020 | Biddle et al. |
| 2011/0207151 A1 | 8/2011 | Barbreau et al. |

FOREIGN PATENT DOCUMENTS

| JP | 59048458 | 3/1984 |
| WO | WO 2017/100268 | 6/2017 |
| WO | PCT/US2021/059786 | 11/2021 |
| WO | PCT/WO2021/059787 | 11/2021 |
| WO | WO 2015/010107 | 1/2022 |

OTHER PUBLICATIONS

U.S. Appl. No. 63/115,420, filed Nov. 18, 2020, Mark J. Suto (Southern Research Institute).
U.S. Appl. No. 63/115,421, filed Nov. 18, 2020, Mark J. Suto (Southern Research Institute).
U.S. Appl. No. 17/529,199 (US 2022/0153702 A1), filed Nov. 17, 2021, Mark J. Suto (Southern Research Institute).
Hanaineh-Abdelnour, et al. (1999) "Some Synthetic Applications of 2,3-Dichloro-N-phenylmaleimide: A Novel Synthesis of 2-Phenylpyrrolo[3,4-b]quinoxaline-1, 3-diones. I," Tetrahedron 55(40): 11859-11870.
Li, et al. (2016) "A Mild and Selective Protecting and Reversed Modification of Thiols." Tetrahedron Letters, 57(24), 2660-2663.
Liu, et al. (1981) "Potential antineoplastic sulfhydryl agents. II. Synthesis and determination of the lipophilic constants of $N,N^2$-diaryl-2-aminomaleimides," Taiwan Yaoxue Zazhi 32(2): English language Abstract.
Pubchem SID 365284177, Available Date: May 25, 2018 [retrieved on Jan. 14, 20220 retrieved from the internet <URL: https://pubchem.ncbi.nlm.nih.gov/substance/365284177 > entire document.
Pubchem SID 236264058, Available Date: Feb. 13, 2015 [retrieved on Jan. 14, 20220 retrieved from the internet <URL: https://pubchem.ncbi.nlm.nih.gov/substance/236264058 > entire document.
Deshane, et al. (2010) "Sp1 regulates chromatin looping between an intronic enhancer and distal promoter of the human heme oxygenase-1 gene in renal cells" *J Biol Chem* 285(22): 16476-86.
Liby, et al. (2005) "The synthetic triterpenoids, CDDO and CDDO-imidazolide, are potent inducers of heme oxygenase-1 and Nrf2/ARE signaling" *Cancer Res* 65(11): 4789.
Hock, et al. (2007) "JunB and JunD regulate human heme oxygenase-1 gene expression in renal epithelial cells," *J Biol Chem* 282: 6875-6886.

* cited by examiner

*Primary Examiner* — Timothy R Rozof
(74) *Attorney, Agent, or Firm* — Ballard Spahr LLP

(57) ABSTRACT

The present disclosure is concerned with thioquinolinone compounds for the treatment of disorders associated with heme oxygenase-1 (HO-1) signaling dysfunction such as, for example, kidney diseases (e.g., chronic kidney disease, acute kidney injury). This abstract is intended as a scanning tool for purposes of searching in the particular art and is not intended to be limiting of the present invention.

19 Claims, 1 Drawing Sheet
Specification includes a Sequence Listing.

SEQUENCE LISTING

<160> NUMBER OF SEQ ID NOS: 2

<210> SEQ ID NO 1
<211> LENGTH: 214
<212> TYPE: DNA
<213> ORGANISM: Artificial sequence
<220> FEATURE:
<223> OTHER INFORMATION: synthetic construct; 220-bp enhancer

<400> SEQUENCE: 1

```
acaaggctgc atcttaaagc gattgagaac gtggcctgaa tgaggatggg agtctcttga      60
aggcctgccc acaggtggga ggctcagcag ttgggaagga ccccacccccc agccagcttt    120 gtgttcacct ttcccatttc ctcctcagca tgccccagga tttgtcagag gccctgaagg    180
aggccaccaa ggaggtgcac acccaggcag agaa                                 214
```

<210> SEQ ID NO 2
<211> LENGTH: 4500
<212> TYPE: DNA
<213> ORGANISM: Artificial sequence
<220> FEATURE:
<223> OTHER INFORMATION: synthetic construct; 4.5-kb promoter

<400> SEQUENCE: 2

```
gcccagggtc cttcctgcct tccttggcag gtgggtccct gacctcctgc attgtggtca      60
ctcccaacca aacacctccc gggaggcgga agttgcaatg agccaagatc aggccattgc    120
actccagtgt gggcaacaag agcaaagctc catctcaaaa aaaaaaaaaa aaaaaaaaa     180 aaagttgccc tttcgaatcc aagggctgct gttttgcaa gtggatgaag ctttccctg      240 agtattcctc ttgcttcctc ccacctcctc ctgtaactga aggattgtcc tgtcctcctt    300
aagcattcat tctgcatgtt accccagcag gaccaggaac cccaaataca aattttcctc    360
tattcctcta atcacttcca tgcccttctc aagatgcatc aagaccctca aggtcaggcc    420
gggcacggtg gctcaagcct ggaatcccag cactttggga ggctgaggag gcggatcac    480 gaggtcagga gatcaagacc atcctggcta acacagtgaa acctggtctc tactaaaaac    540
acaaaaaatt agccgggcgt ggtcgcgggc acctgtagtc ccagctactc gggaggctga    600
ggcaggagaa tggtgtgaac ccgggaggcg gagcttgcag tcacccaaga tcgcgccacc    660
gcactccagc ctgggcaaca gagcgaaacc ccgtcacaaa aaaaaaaag aaaaaagaaa     720 aaaagaaaaa aaaagaccct caaggtcata ttcaaaggga aggaagtcca gccccctga    780 ggcagctggc tgaaaaacag gtttctcata tactaaaaga acttgggaaa tgggaatcag    840
aaatggataa tcattttgtt gctagcatgc tccaagctag ggtcattata aggtgatgga    900
gacaaggaca taggctggcc caaggccaca ggcacaggag acaaaaatac ccgcaggaca    960
gagatgaagg ctgatcccag gctaacagat gaccattaga acacagatga aggccaggtt   1020
aaactggttt attctggaac cccaaggatg aagagggagc ccccggttca cttcagtatc   1080
tcctctgttc tcagtgggta attatgatga gatggggcca aggttaaggg tacacagtaa   1140
gactggttca ttccgaaacc ctaaggatga atgaggaacg ccctgttcag gaaaggataa   1200
caggaaaata agaggatgcc ttctttctg tttttttttt ctgctttgtt ctctctttgc     1260
aggtgggtaa tcacgtcacc gtatgtcagg acatgcccct gcattctcaa aaactgggaa   1320
gtttgatcac ccaaatcttg gaacaaaaag ccacttttcc ttttgaatac tgtttggcct   1380
aaaaatgaac tgggagaaaa ttacaaaagt cagcctttct ttctccaaaa gaatccagtg   1440
cctctatgca ggaaatcctc aaattagcct tctcaggtct tttataatca acagcagaat   1500
```

```
gaggaggaca gggataaaga gacagagaaa tgcagggaac agagagaggc tcaactattg    1560
gctgttttat aagccctcca gccccaccca ggttgccctc agaatcccct cctaggtaac    1620
tgccatcagc gccagaagcc aggccactgg cagataaact gcccccatgg gataaatggg    1680
gaaaagcccc acatagcttg ttcccttttgc cacaagctca gccactggaa acgggactgc   1740
cctgagggtc ataggaaccc ccccaggaca gaatcccaac ccctgatggc catgagctga    1800
aggggttctc tgccctggct ggcttccaaa tcagacattg tcattaacag gacaaagcca    1860
agggtaactt tggaggcggc aagtaaaatt ataaatttcc ctcttgagtt caagagctgc    1920
ctactctgtg ctaatctcct tatctgagca actctcttcc aaatcctgtt gggtaatggg    1980
ggaaaatggc accttctttc tccaaaagaa aaaaatcttt atattactta agggaccaag    2040
gagtttgaga ccagcctggg caacatagtg agaccctgtc tccatcagaa acacaaaaaa    2100
attagccagg tggacgtggt ggcacaggcc tgtggtccta gctacttggg aggctagggt    2160
gggaggatcg cttgagcccg ggtgatggag gctgcagtga gccgagatcg tgccactgca    2220
ctccagcctg agtgacagag tgagacccca tcgcaaaaaa aaaaaaaaat aagtcaagga    2280
tgatgatgat atagactcag ggaatatcat taagtgaacg agaaattatc tttattcccc    2340
acttttaaca tggggaaact gaggcccccag gaagacaacc aagtattggc tgaattgagc    2400
tgagggagat ctcaaatcac tcaatagcga ccaccacctt cccaggcagc tatcgaagtt    2460
cccataatgg gcagatggat cacctggggt caggagttcg agaccagcct ggccaacatg    2520
ataaaacccc atctctacta aaaaatacaaa aattagcc ggatgtggta taattacagc    2580
tgtaatccca gctactaggg aggatgaggc aggaaaattg cttgaacctg ggagacaggt    2640
tgcagtgagc cgaaatcacg ccactgcact ccagcctggg cgacagagca agactcgtca    2700
aaaaaaaaaa aaaaaaaaag gccgggtgcg gtggctcaca cctgtaatca cagcactttg    2760
ggaggctgag gcaggtggat cacgaggtca ggagttcaag acctgcctgg ccaaaatggt    2820
gaaaccccca tctgtactaa aaatacaaaa attagctggg catggtgatg gtgcctgta    2880 atcccagcta ctcgggaggc tgaggcagag aattgcttga acccaggagg cagaggttgc    2940
agtgagccaa gatcgtgcca ctgcactcca gcctgggtga cagagcaaga ctccatctca    3000
aaaaaaaaaa aaaaaaaaag ttcccacggt gctgccgagc ctgtgattgg cagaggcatt    3060
gtttattcgt tcaaggtttt tgttaaggg acccggtgag tatcaactac taggcagttc     3120
tcacttctgc tcacttctgg gctcacttaa gcctaccagc agccctgaag gctgttaacc    3180
accctttaga gcttagagag tcgaagaggc aggggccagg tcctaaagaa aggcacactg    3240
tccccagagc ctggggcgcg atgccacccg ccccccccc cccgcccag gcgtaccccc     3300 ccttaccccg ccccccaccc gctcgccgcg cccagcccat ctggcgccgc tctgcccctg    3360
ctgagtaatc ctttcccgag ccacgtggcc gtgttttttcc tgctgagtca cggtcccgag   3420
gtctattttc gctaagtcac cgccccgaga tctgttttcg ctgagtcacg gtcccggtgt   3480
ctgttttcgc tgagtcacgg tctagagatt tgttttcctc agagttccag ctgctccagg   3540
tttaatcccc tggggcaaag tccggactgt ccggctggag tctggagtcg gacatgcct     3600 cagccagcac gtcctcggcc tcgtctgggg cctgaatcct agggaagcca tagcagctcc    3660 tccaccttc ctctcactcc tcctctagcc tcttgctact ccccgcacca ctgttttagg     3720
gaacctctat ctcccgacgg cctgccacgg gccaggcgct gtgctggggg cttcacactt    3780
taaatcgctg ttgagcgggg cgcggggggcg ctgcaaccta aggtgggag ctactcaaat    3840 ggaggggcat ctgttaaaat ggccggcctg tcattttcaa aaacttcaag gccgggcgcg    3900
```

-continued

```
gtggctcacg cctgtaatcc cagcactttg ggaggccgag gcgggcggat cacgaggtca    3960
ggagatcgag atcatcttgt ctaacacggt gaaacttcat ctctactaaa aatagaaaaa    4020
attagccggg cgtggtggcg ggcgcctgta atcccagcta ctcaggaggc tgaggcagga    4080
gaatggcatg aacccgggag gcggagcttg cagtgagccg aaatcgcgcc actgcagtcc    4140
ggcctgggcg aaagagcaag actccgcctc aaaaaaaaaa aaaaaaaaaa acttcaaagg    4200
ctgaggaacc caaagaggca ggacaagtga atgcaatgca acctcttggg ctggaacctg    4260
gactggtaaa acggctaaag aggaggttat tggggcaata ggggacattt gaatataggc    4320
tttatattga aggagttcag gatatgccac ccaaaatgtg ccactttgga ttaaggatca    4380
ttattattat tattattatt attttgagac agggtctctg tcacccaagc tgcagtgcag    4440
tggcacaatc tcggctcact gcaacctctg cctcctaggt tcaagcgatt ctcgtgcctc    4500
```

COMPOUNDS FOR THE TREATMENT OF ACUTE AND CHRONIC KIDNEY DISEASE

CROSS-REFERENCE TO RELATED APPLICATIONS

This application claims the benefit of U.S. Provisional Application No. 63/115,420, filed on Nov. 18, 2020, the contents of which is incorporated herein by reference in its entirety.

REFERENCE TO SEQUENCE LISTING

The Sequence Listing submitted Nov. 17, 2021 as a text file named "19044_0453U2_ST25.txt," created on Nov. 5, 2021, and having a size of 8,192 bytes is hereby incorporated by reference pursuant to 37 C.F.R. § 1.52(e)(5).

BACKGROUND

Acute kidney injury (AKI) is a major cause for morbidity and mortality in hospitalized patients, developing in about 5-7% of patients and impairing recovery of about 15-25% of intensive care unit (ICU) patients. Despite major advances in renal replacement therapy, the mortality in patients with AKI remains largely unchanged and can be as high as 80% in ICU patients. Additionally, AKI is now linked to the subsequent development of chronic kidney disease (CKD). Numerous therapeutic interventions have been evaluated in clinical trials, with none proven successful. General supportive care and dialysis remain the primary treatment modalities. Thus, there remains a need for compounds and compositions for treating kidney diseases, and methods of making and using same.

SUMMARY

In accordance with the purpose(s) of the invention, as embodied and broadly described herein, the invention, in one aspect, relates to compounds and compositions for use in the prevention and treatment of disorders associated with heme oxygenase-1 (HO-1) signaling such as, for example, kidney diseases including, but not limited to, chronic kidney disease and acute kidney injury.

Thus, disclosed are compounds having a structure represented by a formula:

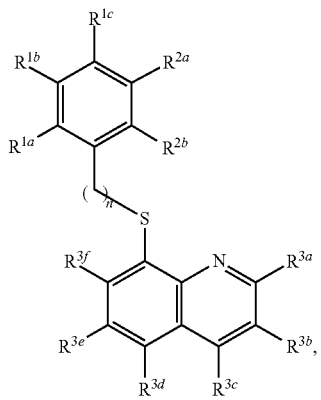

wherein n is 1 or 2; wherein each of $R^{1a}$, $R^{1b}$, and $R^{1c}$ is independently selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl, provided that at least one of $R^{1a}$, $R^{1b}$, and $R^{1c}$ is —OH, C1-C4 alkoxy, or C1-C4 alkylamino; wherein each of $R^{2a}$ and $R^{2b}$ is independently selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; and wherein each of $R^{3a}$, $R^{3b}$, $R^{3c}$, $R^{3d}$, $R^{3e}$, and $R^{3f}$ is independently selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl, provided that at least two of $R^{1a}$, $R^{1b}$, $R^{1c}$, $R^{2a}$, and $R^{2b}$ are non-hydrogen groups, and provided that when n is 1, Z is —S—, and $R^{1a}$ is —OH or C1-C4 alkoxy, then exactly two of $R^{1a}$, $R^{1b}$, $R^{1c}$, $R^{2a}$, and $R^{2b}$ are non-hydrogen groups, or a pharmaceutically acceptable salt thereof.

Also disclosed are methods for treating a disorder associated with heme oxygenase-1 (HO-1) signaling dysfunction in a subject in need thereof, the method comprising administering to the subject an effective amount of compound having a structure represented by a formula:

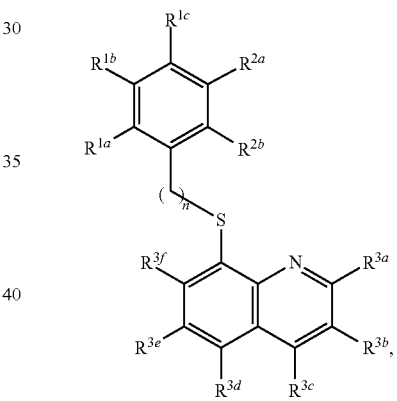

wherein n is 1 or 2; wherein each of $R^{1a}$, $R^{1b}$, and $R^{1c}$ is independently selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl, provided that at least one of $R^{1a}$, $R^{1b}$, and $R^{1c}$ is —OH, C1-C4 alkoxy, or C1-C4 alkylamino; wherein each of $R^{2a}$ and $R^{2b}$ is independently selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; and wherein each of $R^{3a}$, $R^{3b}$, $R^{3c}$, $R^{3d}$, $R^{3e}$, and $R^{3f}$ is independently selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl, provided that at least two of $R^{1a}$, $R^{1b}$, $R^{1c}$, $R^{2a}$, and $R^{2b}$ are non-hydrogen groups, and provided that when n is 1, Z is —S—, and $R^{1a}$ is —OH or C1-C4 alkoxy, then exactly two of $R^{1a}$, $R^{1b}$, $R^{1c}$, $R^{2a}$, and $R^{2b}$ are non-hydrogen groups, or a pharmaceutically acceptable salt thereof, thereby treating the disorder in the subject.

Also disclosed are methods for modifying HO-1 signaling in a subject, the method comprising administering to the subject an effective amount of compound having a structure represented by a formula:

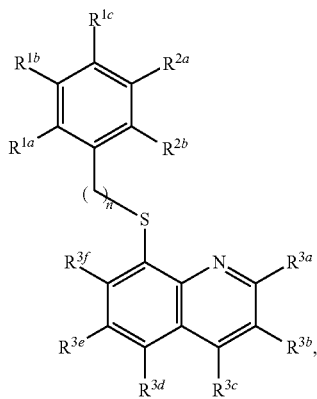

wherein n is 1 or 2; wherein each of $R^{1a}$, $R^{1b}$, and $R^{1c}$ is independently selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl, provided that at least one of $R^{1a}$, $R^{1b}$, and $R^{1c}$ is —OH, C1-C4 alkoxy, or C1-C4 alkylamino; wherein each of $R^{2a}$ and $R^{2b}$ is independently selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; and wherein each of $R^{3a}$, $R^{3b}$, $R^{3e}$, $R^{3d}$, $R^{3e}$, and $R^{31}$ is independently selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl, or a pharmaceutically acceptable salt thereof, thereby modifying HO-1 signaling in the subject.

Also disclosed are methods for modifying HO-1 signaling in a cell, the method comprising contacting the cell with an effective amount of compound having a structure represented by a formula:

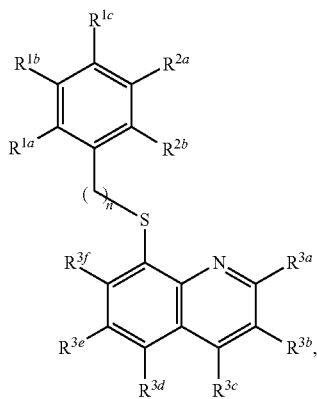

wherein n is 1 or 2; wherein each of $R^{1a}$, $R^{1b}$, and $R^{1c}$ is independently selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl, provided that at least one of $R^{1a}$, $R^{1b}$, and $R^{1c}$ is —OH, C1-C4 alkoxy, or C1-C4 alkylamino; wherein each of $R^{2a}$ and $R^{2b}$ is independently selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; and wherein each of $R^{3a}$, $R^{3b}$, $R^{3e}$, $R^{3d}$, $R^{3e}$, and $R^{3f}$ is independently selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl, or a pharmaceutically acceptable salt thereof, thereby modifying HO-1 signaling in the cell.

Also disclosed are kits comprising compound having a structure represented by a formula:

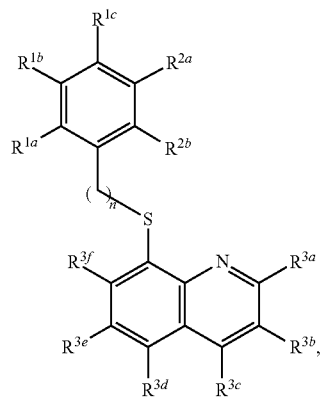

wherein n is 1 or 2; wherein each of $R^{1a}$, $R^{1b}$, and $R^{1c}$ is independently selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl, provided that at least one of $R^{1a}$, $R^{1b}$, and $R^{1c}$ is —OH, C1-C4 alkoxy, or C1-C4 alkylamino; wherein each of $R^{2a}$ and $R^{2b}$ is independently selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; and wherein each of $R^{3a}$, $R^{3b}$, $R^{3c}$, $R^{3d}$, $R^{3e}$, and $R^{3f}$ is independently selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl, or a pharmaceutically acceptable salt thereof, and one or more of: (a) an agent associated with the treatment of a disorder associated with HO-1 signaling dysfunction; (b) instructions for administering the compound in connection with treating a disorder associated with HO-1 signaling dysfunction; and (c) instructions for treating a disorder associated with HO-1 signaling dysfunction.

Also disclosed are compounds having a structure selected from:

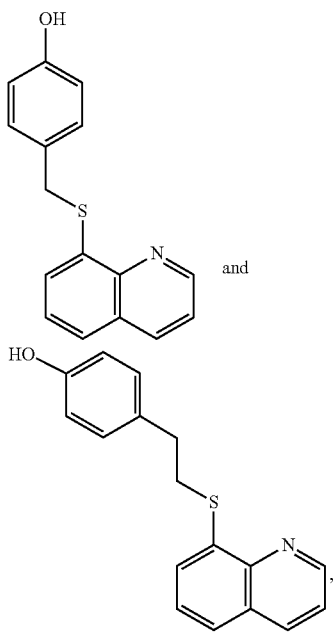

and or a pharmaceutically acceptable salt thereof.

Also disclosed are pharmaceutical compositions comprising a therapeutically effective amount of a disclosed compound and a pharmaceutically acceptable carrier.

Also disclosed are methods for treating a disorder associated with HO-1 signaling dysfunction in a subject in need thereof, the method comprising administering to the subject an effective amount of a disclosed compound, thereby treating the disorder.

Also disclosed are methods for modifying HO-1 signaling in a subject, the method comprising administering to the subject an effective amount of a disclosed compound, thereby modifying HO-1 signaling in the subject.

Also disclosed are methods for modifying HO-1 signaling in a cell, the method comprising contacting the cell with an effective amount of a disclosed compound, thereby modifying HO-1 signaling in the cell.

Also disclosed are kits comprising a disclosed compound, and one or more of: (a) an agent associated with the treatment of a disorder associated with HO-1 signaling dysfunction; (b) instructions for administering the compound in connection with treating a disorder associated with HO-1 signaling dysfunction; and (c) instructions for treating a disorder associated with HO-1 signaling dysfunction.

Also disclosed are methods of identifying a compound that modulates heme oxygenase-1 (HO-1) signaling, the method comprising: (a) contacting a cell with a candidate compound, wherein the cell comprises: (i) a vector comprising: (1) a promoter operably linked to a nucleic acid comprising the sequence of NCBI Accession No. Z82244; (2) an enhancer, wherein the enhancer comprises the sequence of SEQ ID NO: 1; and (3) a selectable marker; or (ii) a vector comprising: (1) a promoter operably linked to a nucleic acid comprising a triple mutant of the sequence of NCBI Accession No. Z82244; and (2) a selectable marker; wherein the vector expresses HO-1 or a mutant thereof, (b) determining expression of the selectable marker in the cell; and (c) identifying the candidate compound as a compound that modulates HO-1 signaling when expression of the selectable marker is modulated in the cell.

Also disclosed are compounds that modulate heme oxygenase-1 (HO-1) identified by a disclosed method.

Also disclosed are method of increasing heme oxygenase-1 (HO-1) signaling in a subject, the method comprising administering a compound that increases HO-1 signaling, wherein the ability of the compound to increase HO-1 signaling is determined by: (a) contacting a cell with a candidate compound, wherein the cell comprises: (i) a vector comprising: (1) a promoter operably linked to a nucleic acid comprising the sequence of NCBI accession no. Z82244; (2) an enhancer, wherein the enhancer comprises the sequence of SEQ ID NO: 1; and (3) a selectable marker; or (ii) a vector comprising: (1) a promoter operably linked to a nucleic acid comprising a triple mutant of the sequence of NCBI accession no. Z82244; and (2) a selectable marker; wherein the vector expresses HO-1 or a mutant thereof, (b) determining expression of the selectable marker in the cell; and (c) identifying the candidate compound as a compound that that increases HO-1 signaling when expression of the selectable marker is increased in the cell.

While aspects of the present invention can be described and claimed in a particular statutory class, such as the system statutory class, this is for convenience only and one of skill in the art will understand that each aspect of the present invention can be described and claimed in any statutory class. Unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

BRIEF DESCRIPTION OF THE FIGURES

The accompanying figures, which are incorporated in and constitute a part of this specification, illustrate several aspects and together with the description serve to explain the principles of the invention.

Figure 1:
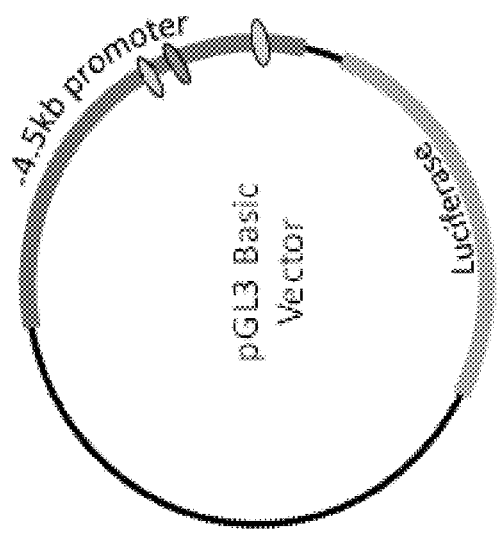
FIG. 1 shows a representative schematic of a pHOGL3/4.5+220 construct.

Additional advantages of the invention will be set forth in part in the description which follows, and in part will be obvious from the description, or can be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention.

DETAILED DESCRIPTION

The present invention can be understood more readily by reference to the following detailed description of the invention and the Examples included therein.

Before the present compounds, compositions, articles, systems, devices, and/or methods are disclosed and described, it is to be understood that they are not limited to specific synthetic methods unless otherwise specified, or to particular reagents unless otherwise specified, as such may, of course, vary. It is also to be understood that the terminology used herein is for the purpose of describing particular aspects only and is not intended to be limiting. Although any methods and materials similar or equivalent to those described herein can be used in the practice or testing of the present invention, example methods and materials are now described.

While aspects of the present invention can be described and claimed in a particular statutory class, such as the system statutory class, this is for convenience only and one of skill in the art will understand that each aspect of the present invention can be described and claimed in any statutory class. Unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

Throughout this application, various publications are referenced. The disclosures of these publications in their entireties are hereby incorporated by reference into this application in order to more fully describe the state of the art to which this pertains. The references disclosed are also individually and specifically incorporated by reference herein for the material contained in them that is discussed in the sentence in which the reference is relied upon. Nothing herein is to be construed as an admission that the present invention is not entitled to antedate such publication by virtue of prior invention. Further, the dates of publication provided herein may be different from the actual publication dates, which can require independent confirmation.

A. Definitions

As used in the specification and the appended claims, the singular forms "a," "an" and "the" include plural referents unless the context clearly dictates otherwise. Thus, for example, reference to "a functional group," "an alkyl," or "a residue" includes mixtures of two or more such functional groups, alkyls, or residues, and the like.

As used in the specification and in the claims, the term "comprising" can include the aspects "consisting of" and "consisting essentially of".

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

As used herein, the terms "about" and "at or about" mean that the amount or value in question can be the value designated some other value approximately or about the same. It is generally understood, as used herein, that it is the nominal value indicated ±10% variation unless otherwise indicated or inferred. The term is intended to convey that similar values promote equivalent results or effects recited in the claims. That is, it is understood that amounts, sizes, formulations, parameters, and other quantities and characteristics are not and need not be exact, but can be approximate and/or larger or smaller, as desired, reflecting tolerances, conversion factors, rounding off, measurement error and the like, and other factors known to those of skill in the art. In general, an amount, size, formulation, parameter or other quantity or characteristic is "about" or "approximate" whether or not expressly stated to be such. It is understood that where "about" is used before a quantitative value, the parameter also includes the specific quantitative value itself, unless specifically stated otherwise.

References in the specification and concluding claims to parts by weight of a particular element or component in a composition denotes the weight relationship between the element or component and any other elements or components in the composition or article for which a part by weight is expressed. Thus, in a compound containing 2 parts by weight of component X and 5 parts by weight component Y, X and Y are present at a weight ratio of 2:5, and are present in such ratio regardless of whether additional components are contained in the compound.

A weight percent (wt. %) of a component, unless specifically stated to the contrary, is based on the total weight of the formulation or composition in which the component is included.

As used herein, "$IC_{50}$," is intended to refer to the concentration of a substance (e.g., a compound or a drug) that is required for 50% inhibition of a biological process, or component of a process, including a protein, subunit, organelle, ribonucleoprotein, etc. In one aspect, an $IC_{50}$ can refer to the concentration of a substance that is required for 50% inhibition in vivo, as further defined elsewhere herein. In a further aspect, $IC_{50}$ refers to the half-maximal (50%) inhibitory concentration (IC) of a substance.

As used herein, "$EC_{50}$," is intended to refer to the concentration of a substance (e.g., a compound or a drug) that is required for 50% agonism of a biological process, or component of a process, including a protein, subunit, organelle, ribonucleoprotein, etc. In one aspect, an $EC_{50}$ can refer to the concentration of a substance that is required for 50% agonism in vivo, as further defined elsewhere herein. In a further aspect, $EC_{50}$ refers to the concentration of agonist that provokes a response halfway between the baseline and maximum response.

As used herein, the terms "optional" or "optionally" means that the subsequently described event or circumstance can or cannot occur, and that the description includes instances where said event or circumstance occurs and instances where it does not.

As used herein, the term "subject" can be a vertebrate, such as a mammal, a fish, a bird, a reptile, or an amphibian. Thus, the subject of the herein disclosed methods can be a human, non-human primate, horse, pig, rabbit, dog, sheep, goat, cow, cat, guinea pig or rodent. The term does not denote a particular age or sex. Thus, adult and newborn subjects, as well as fetuses, whether male or female, are intended to be covered. In one aspect, the subject is a mammal. A patient refers to a subject afflicted with a disease or disorder. The term "patient" includes human and veterinary subjects.

As used herein, the term "treatment" refers to the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder. In various aspects, the term covers any treatment of a subject, including a mammal (e.g., a human), and includes: (i) preventing the disease from occurring in a subject that can be predisposed to the disease but has not yet been diagnosed as having it; (ii) inhibiting the disease, i.e., arresting its development; or (iii) relieving the disease, i.e., causing regression of the disease. In one aspect, the subject is a mammal such as a primate, and, in a further aspect, the subject is a human. The term "subject" also includes domesticated animals (e.g., cats, dogs, etc.), livestock (e.g., cattle, horses, pigs, sheep, goats, etc.), and laboratory animals (e.g., mouse, rabbit, rat, guinea pig, fruit fly, etc.).

As used herein, the term "prevent" or "preventing" refers to precluding, averting, obviating, forestalling, stopping, or hindering something from happening, especially by advance action. It is understood that where reduce, inhibit or prevent are used herein, unless specifically indicated otherwise, the use of the other two words is also expressly disclosed.

As used herein, the term "diagnosed" means having been subjected to a physical examination by a person of skill, for example, a physician, and found to have a condition that can be diagnosed or treated by the compounds, compositions, or methods disclosed herein.

As used herein, the terms "administering" and "administration" refer to any method of providing a pharmaceutical preparation to a subject. Such methods are well known to those skilled in the art and include, but are not limited to, oral administration, transdermal administration, administration by inhalation, nasal administration, topical administration, intravaginal administration, ophthalmic administration, intraaural administration, intracerebral administration, rectal administration, sublingual administration, buccal administration, and parenteral administration, including injectable such as intravenous administration, intra-arterial administration, intramuscular administration, and subcutaneous administration. Administration can be continuous or intermittent. In various aspects, a preparation can be administered therapeutically; that is, administered to treat an existing disease or condition. In further various aspects, a preparation can be administered prophylactically; that is, administered for prevention of a disease or condition.

As used herein, the terms "effective amount" and "amount effective" refer to an amount that is sufficient to achieve the desired result or to have an effect on an undesired condition. For example, a "therapeutically effective amount" refers to an amount that is sufficient to achieve the desired therapeutic result or to have an effect on undesired symptoms, but is generally insufficient to cause adverse side effects. The specific therapeutically effective dose level for any particular patient will depend upon a variety of factors including the disorder being treated and the severity of the disorder; the specific composition employed; the age, body weight, general health, sex and diet of the patient; the time of administration; the route of administration; the rate of excretion of the specific compound employed; the duration of the treatment; drugs used in combination or coincidental with the specific compound employed and like factors well known in the medical arts. For example, it is well within the skill of the art to start doses of a compound at levels lower than those required to achieve the desired therapeutic effect and to gradually increase the dosage until the desired effect is achieved. If desired, the effective daily dose can be divided into multiple doses for purposes of administration. Consequently, single dose compositions can contain such amounts or submultiples thereof to make up the daily dose. The dosage can be adjusted by the individual physician in the event of any contraindications. Dosage can vary, and can be administered in one or more dose administrations daily, for one or several days. Guidance can be found in the literature for appropriate dosages for given classes of pharmaceutical products. In further various aspects, a preparation can be administered in a "prophylactically effective amount"; that is, an amount effective for prevention of a disease or condition.

As used herein, "dosage form" means a pharmacologically active material in a medium, carrier, vehicle, or device suitable for administration to a subject. A dosage forms can comprise inventive a disclosed compound, a product of a disclosed method of making, or a salt, solvate, or polymorph thereof, in combination with a pharmaceutically acceptable excipient, such as a preservative, buffer, saline, or phosphate buffered saline. Dosage forms can be made using conventional pharmaceutical manufacturing and compounding techniques. Dosage forms can comprise inorganic or organic buffers (e.g., sodium or potassium salts of phosphate, carbonate, acetate, or citrate) and pH adjustment agents (e.g., hydrochloric acid, sodium or potassium hydroxide, salts of citrate or acetate, amino acids and their salts) antioxidants (e.g., ascorbic acid, alpha-tocopherol), surfactants (e.g., polysorbate 20, polysorbate 80, polyoxyethylene 9-10 nonyl phenol, sodium desoxycholate), solution and/or cryo/lyo stabilizers (e.g., sucrose, lactose, mannitol, trehalose), osmotic adjustment agents (e.g., salts or sugars), antibacterial agents (e.g., benzoic acid, phenol, gentamicin), antifoaming agents (e.g., polydimethylsilozone), preservatives (e.g., thimerosal, 2-phenoxyethanol, EDTA), polymeric stabilizers and viscosity-adjustment agents (e.g., polyvinylpyrrolidone, poloxamer 488, carboxymethylcellulose) and co-solvents (e.g., glycerol, polyethylene glycol, ethanol). A dosage form formulated for injectable use can have a disclosed compound, a product of a disclosed method of making, or a salt, solvate, or polymorph thereof, suspended in sterile saline solution for injection together with a preservative.

As used herein, "kit" means a collection of at least two components constituting the kit. Together, the components constitute a functional unit for a given purpose. Individual member components may be physically packaged together or separately. For example, a kit comprising an instruction for using the kit may or may not physically include the instruction with other individual member components. Instead, the instruction can be supplied as a separate member component, either in a paper form or an electronic form which may be supplied on computer readable memory device or downloaded from an internet website, or as recorded presentation.

As used herein, "instruction(s)" means documents describing relevant materials or methodologies pertaining to a kit. These materials may include any combination of the following: background information, list of components and their availability information (purchase information, etc.), brief or detailed protocols for using the kit, trouble-shooting, references, technical support, and any other related documents. Instructions can be supplied with the kit or as a separate member component, either as a paper form or an electronic form which may be supplied on computer readable memory device or downloaded from an internet website, or as recorded presentation. Instructions can comprise one or multiple documents, and are meant to include future updates.

As used herein, the terms "therapeutic agent" include any synthetic or naturally occurring biologically active compound or composition of matter which, when administered to an organism (human or nonhuman animal), induces a desired pharmacologic, immunogenic, and/or physiologic effect by local and/or systemic action. The term therefore encompasses those compounds or chemicals traditionally regarded as drugs, vaccines, and biopharmaceuticals including molecules such as proteins, peptides, hormones, nucleic acids, gene constructs and the like. Examples of therapeutic agents are described in well-known literature references such as the Merck Index ($14^{th}$ edition), the Physicians' Desk Reference ($64^{th}$ edition), and The Pharmacological Basis of Therapeutics ($12^{th}$ edition), and they include, without limitation, medicaments; vitamins; mineral supplements; substances used for the treatment, prevention, diagnosis, cure or mitigation of a disease or illness; substances that affect the structure or function of the body, or pro-drugs, which become biologically active or more active after they have been placed in a physiological environment. For example, the term "therapeutic agent" includes compounds or compositions for use in all of the major therapeutic areas including, but not limited to, adjuvants; anti-infectives such as antibiotics and antiviral agents; anti-cancer and anti-neoplastic agents such as kinase inhibitors, poly ADP ribose polymerase (PARP) inhibitors and other DNA damage response modifiers, epigenetic agents such as bromodomain and extra-terminal (BET) inhibitors, histone deacetylase (HDAc) inhibitors, iron chelators and other ribonucleotides reductase inhibitors, proteasome inhibitors and Nedd8-activating enzyme (NAE) inhibitors, mammalian target of rapamycin (mTOR) inhibitors, traditional cytotoxic agents such as paclitaxel, dox, irinotecan, and platinum compounds, immune checkpoint blockade agents such as cytotoxic T lymphocyte antigen-4 (CTLA-4) monoclonal antibody (mAB), programmed cell death protein 1 (PD-1)/programmed cell death-ligand 1 (PD-L1) mAB, cluster of differentiation 47 (CD47) mAB, toll-like receptor (TLR) agonists and other immune modifiers, cell therapeutics such as chimeric antigen receptor T-cell (CAR-T)/chimeric antigen receptor natural killer (CAR-NK) cells, and proteins such as interferons (IFNs), interleukins (ILs), and mAbs; anti-ALS agents such as entry inhibitors, fusion inhibitors, non-nucleoside reverse transcriptase inhibitors (NNRTIs), nucleoside reverse transcriptase inhibitors (NRTIs), nucleotide reverse transcriptase inhibitors, NCP7 inhibitors, protease inhibitors, and integrase inhibitors; analgesics and analgesic combinations, anorexics, anti-inflammatory agents, anti-epileptics, local and general anesthetics, hypnotics, sedatives, antipsychotic agents, neuroleptic agents, antidepressants, anxiolytics, antagonists, neuron blocking agents, anticholinergic and cholinomimetic agents, antimuscarinic and muscarinic agents, antiadrenergics, antiarrhythmics, antihypertensive agents, hormones, and nutrients, antiarthritics, antiasthmatic agents, anticonvulsants, antihistamines, antinauseants, antineoplastics, antipruritics, antipyretics; antispasmodics, cardiovascular preparations (including calcium channel blockers, beta-blockers, beta-agonists and antiarrythmics), antihypertensives, diuretics, vasodilators; central nervous system stimulants; cough and cold preparations; decongestants; diagnostics; hormones; bone growth stimulants and bone resorption inhibitors; immunosuppressives; muscle relaxants; psychostimulants; sedatives; tranquilizers; proteins, peptides, and fragments thereof (whether naturally occurring, chemically synthesized or recombinantly produced); and nucleic acid molecules (polymeric forms of two or more nucleotides, either ribonucleotides (RNA) or deoxyribonucleotides (DNA) including both double- and single-stranded molecules, gene constructs, expression vectors, antisense molecules and the like), small molecules (e.g., doxorubicin) and other biologically active macromolecules such as, for example, proteins and enzymes. The agent may be a biologically active agent used in medical, including veterinary, applications and in agriculture, such as with plants, as well as other areas. The term "therapeutic agent" also includes without limitation, medicaments; vitamins; mineral supplements; substances used for the treatment, prevention, diagnosis, cure or mitigation of disease or illness; or substances which affect the structure or function of the body; or pro-drugs, which become biologically active or more active after they have been placed in a predetermined physiological environment.

The term "pharmaceutically acceptable" describes a material that is not biologically or otherwise undesirable, i.e., without causing an unacceptable level of undesirable biological effects or interacting in a deleterious manner.

As used herein, the term "derivative" refers to a compound having a structure derived from the structure of a parent compound (e.g., a compound disclosed herein) and whose structure is sufficiently similar to those disclosed herein and based upon that similarity, would be expected by one skilled in the art to exhibit the same or similar activities and utilities as the claimed compounds, or to induce, as a precursor, the same or similar activities and utilities as the claimed compounds. Exemplary derivatives include salts, esters, amides, salts of esters or amides, and N-oxides of a parent compound.

As used herein, the term "pharmaceutically acceptable carrier" refers to sterile aqueous or nonaqueous solutions, dispersions, suspensions or emulsions, as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol and the like), carboxymethylcellulose and suitable mixtures thereof, vegetable oils (such as olive oil) and injectable organic esters such as ethyl oleate. Proper fluidity can be maintained, for example, by the use of coating materials such as lecithin, by the maintenance of the required particle size in the case of dispersions and by the use of surfactants. These compositions can also contain adjuvants such as preservatives, wetting agents, emulsifying agents and dispersing agents. Prevention of the action of microorganisms can be ensured by the inclusion of various antibacterial and antifungal agents such as paraben, chlorobutanol, phenol, sorbic acid and the like. It can also be desirable to include isotonic agents such as sugars, sodium chloride and the like. Prolonged absorption of the injectable pharmaceutical form can be brought about by the inclusion of agents, such as aluminum monostearate and gelatin, which delay absorption. Injectable depot forms are made by forming microencapsule matrices of the drug in biodegradable polymers such as polylactide-polyglycolide, poly(orthoesters) and poly(anhydrides). Depending upon the ratio of drug to polymer and the nature of the particular polymer employed, the rate of drug release can be controlled. Depot injectable formulations are also prepared by entrapping the drug in liposomes or microemulsions which are compatible with body tissues. The injectable formulations can be sterilized, for example, by filtration through a bacterial-retaining filter or by incorporating sterilizing agents in the form of sterile solid compositions which can be dissolved or dispersed in sterile water or other sterile injectable media just prior to use. Suitable inert carriers can include sugars such as lactose. Desirably, at least 95% by weight of the particles of the active ingredient have an effective particle size in the range of 0.01 to 10 micrometers.

As used herein, "modulate," "modulating," and "modulation" mean a change in activity or function or number. The change may be an increase or a decrease, an enhancement or an inhibition of the activity, function, or number.

The terms "alter" or "modulate" can be used interchangeably herein. When used in reference to, for example, the expression of a nucleotide sequence in a cell, "alter" or "modulate" means that the level of expression of the nucleotide sequence in a cell after applying a method as described herein is different from its expression in the cell before applying the method.

As used herein, a "candidate compound" can be a compound suspected to modulate HO-1 signaling.

The term "vector" or "construct" refers to a nucleic acid sequence capable of transporting into a cell another nucleic acid to which the vector sequence has been linked. The term "expression vector" includes any vector, (e.g., a plasmid, cosmid, or phage chromosome) containing a gene construct in a form suitable for expression by a cell (e.g., linked to a transcriptional control element). "Plasmid" and "vector" are used interchangeably, as a plasmid is a commonly used form of vector. Moreover, the invention is intended to include other vectors that serve equivalent functions.

The term "expression vector" is used herein to refer to vectors that are capable of directing the expression of genes to which they are operatively-linked. Common expression vectors of utility in recombinant DNA techniques are often in the form of plasmids. Recombinant expression vectors can comprise a nucleic acid as disclosed herein in a form suitable for expression of the acid in a host cell. In other words, the recombinant expression vectors can include one or more regulatory elements or promoters, which can be selected based on the host cells used for expression that is operatively linked to the nucleic acid sequence to be expressed.

The term "operatively linked to" refers to the functional relationship of a nucleic acid with another nucleic acid sequence. Promoters, enhancers, transcriptional and translational stop sites, and other signal sequences are examples of nucleic acid sequences operatively linked to other sequences. For example, operative linkage of DNA to a transcriptional control element refers to the physical and functional relationship between the DNA and promoter such that the transcription of such DNA is initiated from the promoter by an RNA polymerase that specifically recognizes, binds to and transcribes the DNA.

As used herein, the terms "promoter," "promoter element," or "promoter sequence" are equivalents and, as used herein, refer to a DNA sequence that when operatively linked to a nucleotide sequence of interest is capable of controlling the transcription of the nucleotide sequence of interest into mRNA. A promoter is typically, though not necessarily, located 5' (i.e., upstream) of a nucleotide sequence of interest (e.g., proximal to the transcriptional start site of a structural gene) whose transcription into mRNA it controls, and provides a site for specific binding by RNA polymerase and other transcription factors for initiation of transcription.

Suitable promoters can be derived from genes of the host cells where expression should occur or from pathogens for this host cells (e.g., tissue promoters or pathogens like viruses). If a promoter is an inducible promoter, then the rate of transcription increases in response to an inducing agent. In contrast, the rate of transcription is not regulated by an inducing agent if the promoter is a constitutive promoter. Also, the promoter may be regulated in a tissue-specific or tissue preferred manner such that it is only active in transcribing the associated coding region in a specific tissue type(s) such as leaves, roots, or meristem. The term "tissue specific," as it applies to a promoter, refers to a promoter that is capable of directing selective expression of a nucleotide sequence or gene of interest to a specific type of tissue in the relative absence of expression of the same nucleotide sequence or gene of interest in a different type of tissue.

Disclosed herein are vectors comprising any of the nucleic acid constructs described herein. Vectors comprising nucleic acids or polynucleotides as described herein are also provided. As used herein, a "vector" refers a carrier molecule into which another DNA segment can be inserted to initiate replication of the inserted segment. A nucleic acid sequence can be "exogenous," which means that it is foreign to the cell into which the vector is being introduced or that the sequence is homologous to a sequence in the cell but in a position within the host cell nucleic acid in which the sequence is ordinarily not found. Vectors include plasmids, cosmids, and viruses (e.g., bacteriophage, animal viruses, and plant viruses), and artificial chromosomes (e.g., YACs). Vectors can comprise targeting molecules. A targeting molecule is one that directs the desired nucleic acid to a particular organ, tissue, cell, or other location in a subject's body. A vector, generally, brings about replication when it is associated with the proper control elements (e.g., a promoter, a stop codon, and a polyadenylation signal). Examples of vectors that are routinely used in the art include plasmids and viruses. The term "vector" includes expression vectors and refers to a vector containing a nucleic acid sequence coding for at least part of a gene product capable of being transcribed. A variety of ways can be used to introduce an expression vector into cells. In some aspects, the expression vector comprises a virus or an engineered vector derived from a viral genome. As used herein, "expression vector" is a vector that includes a regulatory region. A variety of host/expression vector combinations can be used to express the nucleic acid sequences disclosed herein. Examples of expression vectors include but are not limited to plasmids and viral vectors derived from, for example, bacteriophages, retroviruses (e.g., lentiviruses), and other viruses (e.g., adenoviruses, poxviruses, herpesviruses, and adeno-associated viruses). Vectors and expression systems are commercially available and known to one skilled in the art.

The vectors disclosed herein can also include detectable label or selectable marker. Such detectable labels or selectable marker can include a tag sequence designed for detection (e.g., purification or localization) of an expressed polypeptide or polynucleotide. Tag sequences include, for example, fluorescent fusion protein, glutathione S-transferase, polyhistidine, c-myc, hemagglutinin, or Flag™ tag, and can be fused with a polynucleotide encoding a polypeptide, an encoded polypeptide or can be inserted anywhere within the polypeptide, including at either the carboxyl or amino terminus.

Detection of the tagged molecule can be achieved using a number of different techniques. Examples of such techniques include: immunohistochemistry, immunoprecipitation, flow cytometry, immunofluorescence microscopy, ELISA, immunoblotting ("Western blotting"), and affinity chromatography. Epitope tags add a known epitope (e.g., antibody binding site) on the subject protein, to provide binding of a known and often high-affinity antibody, and thereby allowing one to specifically identify and track the tagged protein that has been added to a living organism or to cultured cells. Examples of epitope tags include, but are not limited to, myc, T7, GST, GFP, HA (hemagglutinin), V5, and FLAG tags.

As used herein, the term "substituted" is contemplated to include all permissible substituents of organic compounds. In a broad aspect, the permissible substituents include acyclic and cyclic, branched and unbranched, carbocyclic and heterocyclic, and aromatic and nonaromatic substituents of organic compounds. Illustrative substituents include, for example, those described below. The permissible substituents can be one or more and the same or different for appropriate organic compounds. For purposes of this disclosure, the heteroatoms, such as nitrogen, can have hydrogen substituents and/or any permissible substituents of organic compounds described herein which satisfy the valences of the heteroatoms. This disclosure is not intended to be limited in any manner by the permissible substituents of organic compounds. Also, the terms "substitution" or "substituted with" include the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc. It is also contemplated that, in certain aspects, unless expressly indicated to the contrary, individual substituents can be further optionally substituted (i.e., further substituted or unsubstituted).

In defining various terms, "$A^1$," "$A^2$," "$A^3$," and "$A^4$" are used herein as generic symbols to represent various specific substituents. These symbols can be any substituent, not limited to those disclosed herein, and when they are defined to be certain substituents in one instance, they can, in another instance, be defined as some other substituents.

The term "aliphatic" or "aliphatic group," as used herein, denotes a hydrocarbon moiety that may be straight-chain (i.e., unbranched), branched, or cyclic (including fused, bridging, and spirofused polycyclic) and may be completely saturated or may contain one or more units of unsaturation, but which is not aromatic. Unless otherwise specified, aliphatic groups contain 1-20 carbon atoms. Aliphatic groups include, but are not limited to, linear or branched, alkyl, alkenyl, and alkynyl groups, and hybrids thereof such as (cycloalkyl)alkyl, (cycloalkenyl)alkyl or (cycloalkyl)alkenyl.

The term "alkyl" as used herein is a branched or unbranched saturated hydrocarbon group of 1 to 24 carbon atoms, such as methyl, ethyl, n-propyl, isopropyl, n-butyl, isobutyl, s-butyl, t-butyl, n-pentyl, isopentyl, s-pentyl, neopentyl, hexyl, heptyl, octyl, nonyl, decyl, dodecyl, tetradecyl, hexadecyl, eicosyl, tetracosyl, and the like. The alkyl group can be cyclic or acyclic. The alkyl group can be branched or unbranched. The alkyl group can also be substituted or unsubstituted. For example, the alkyl group can be substituted with one or more groups including, but not limited to, alkyl, cycloalkyl, alkoxy, amino, ether, halide, hydroxy, nitro, silyl, sulfo-oxo, or thiol, as described herein. A "lower alkyl" group is an alkyl group containing from one to six (e.g., from one to four) carbon atoms. The term alkyl group can also be a C1 alkyl, C1-C2 alkyl, C1-C3 alkyl, C1-C4 alkyl, C1-C5 alkyl, C1-C6 alkyl, C1-C7 alkyl, C1-C8 alkyl, C1-C9 alkyl, C1-C10 alkyl, and the like up to and including a C1-C24 alkyl.

Throughout the specification "alkyl" is generally used to refer to both unsubstituted alkyl groups and substituted alkyl groups; however, substituted alkyl groups are also specifically referred to herein by identifying the specific substituent(s) on the alkyl group. For example, the term "halogenated alkyl" or "haloalkyl" specifically refers to an alkyl group that is substituted with one or more halide, e.g., fluorine, chlorine, bromine, or iodine. Alternatively, the term "monohaloalkyl" specifically refers to an alkyl group that is substituted with a single halide, e.g. fluorine, chlorine, bromine, or iodine. The term "polyhaloalkyl" specifically refers to an alkyl group that is independently substituted with two or more halides, i.e. each halide substituent need not be the same halide as another halide substituent, nor do the multiple instances of a halide substituent need to be on the same carbon. The term "alkoxyalkyl" specifically refers to an alkyl group that is substituted with one or more alkoxy groups, as described below. The term "aminoalkyl" specifically refers to an alkyl group that is substituted with one or more amino groups. The term "hydroxyalkyl" specifically refers to an alkyl group that is substituted with one or more hydroxy groups. When "alkyl" is used in one instance and a specific term such as "hydroxyalkyl" is used in another, it is not meant to imply that the term "alkyl" does not also refer to specific terms such as "hydroxyalkyl" and the like.

This practice is also used for other groups described herein. That is, while a term such as "cycloalkyl" refers to both unsubstituted and substituted cycloalkyl moieties, the substituted moieties can, in addition, be specifically identified herein; for example, a particular substituted cycloalkyl can be referred to as, e.g., an "alkylcycloalkyl." Similarly, a substituted alkoxy can be specifically referred to as, e.g., a "halogenated alkoxy," a particular substituted alkenyl can be, e.g., an "alkenylalcohol," and the like. Again, the practice of using a general term, such as "cycloalkyl," and a specific term, such as "alkylcycloalkyl," is not meant to imply that the general term does not also include the specific term.

The term "cycloalkyl" as used herein is a non-aromatic carbon-based ring composed of at least three carbon atoms. Examples of cycloalkyl groups include, but are not limited to, cyclopropyl, cyclobutyl, cyclopentyl, cyclohexyl, norbornyl, and the like. The term "heterocycloalkyl" is a type of cycloalkyl group as defined above, and is included within the meaning of the term "cycloalkyl," where at least one of the carbon atoms of the ring is replaced with a heteroatom such as, but not limited to, nitrogen, oxygen, sulfur, or phosphorus. The cycloalkyl group and heterocycloalkyl group can be substituted or unsubstituted. The cycloalkyl group and heterocycloalkyl group can be substituted with one or more groups including, but not limited to, alkyl, cycloalkyl, alkoxy, amino, ether, halide, hydroxy, nitro, silyl, sulfo-oxo, or thiol as described herein.

The term "polyalkylene group" as used herein is a group having two or more CH$_2$ groups linked to one another. The polyalkylene group can be represented by the formula —(CH$_2$)$_a$—, where "a" is an integer of from 2 to 500.

The terms "alkoxy" and "alkoxyl" as used herein to refer to an alkyl or cycloalkyl group bonded through an ether linkage; that is, an "alkoxy" group can be defined as —OA$^1$ where A$^1$ is alkyl or cycloalkyl as defined above. "Alkoxy" also includes polymers of alkoxy groups as just described; that is, an alkoxy can be a polyether such as —OA$^1$-OA$^2$ or —OA$^1$-(OA$^2$)$_a$-OA$^3$, where "a" is an integer of from 1 to 200 and A$^1$, A$^2$, and A$^3$ are alkyl and/or cycloalkyl groups.

The term "alkenyl" as used herein is a hydrocarbon group of from 2 to 24 carbon atoms with a structural formula containing at least one carbon-carbon double bond. Asymmetric structures such as (A$^1$A$^2$)C=C(A$^3$A$^4$) are intended to include both the E and Z isomers. This can be presumed in structural formulae herein wherein an asymmetric alkene is present, or it can be explicitly indicated by the bond symbol C=C. The alkenyl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol, as described herein.

The term "cycloalkenyl" as used herein is a non-aromatic carbon-based ring composed of at least three carbon atoms and containing at least one carbon-carbon double bound, i.e., C=C. Examples of cycloalkenyl groups include, but are not limited to, cyclopropenyl, cyclobutenyl, cyclopentenyl, cyclopentadienyl, cyclohexenyl, cyclohexadienyl, norbornenyl, and the like. The term "heterocycloalkenyl" is a type of cycloalkenyl group as defined above, and is included within the meaning of the term "cycloalkenyl," where at least one of the carbon atoms of the ring is replaced with a heteroatom such as, but not limited to, nitrogen, oxygen, sulfur, or phosphorus. The cycloalkenyl group and heterocycloalkenyl group can be substituted or unsubstituted. The cycloalkenyl group and heterocycloalkenyl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein.

The term "alkynyl" as used herein is a hydrocarbon group of 2 to 24 carbon atoms with a structural formula containing at least one carbon-carbon triple bond. The alkynyl group can be unsubstituted or substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol, as described herein.

The term "cycloalkynyl" as used herein is a non-aromatic carbon-based ring composed of at least seven carbon atoms and containing at least one carbon-carbon triple bound. Examples of cycloalkynyl groups include, but are not limited to, cycloheptynyl, cyclooctynyl, cyclononynyl, and the like. The term "heterocycloalkynyl" is a type of cycloalkenyl group as defined above, and is included within the meaning of the term "cycloalkynyl," where at least one of the carbon atoms of the ring is replaced with a heteroatom such as, but not limited to, nitrogen, oxygen, sulfur, or phosphorus. The cycloalkynyl group and heterocycloalkynyl group can be substituted or unsubstituted. The cycloalkynyl group and heterocycloalkynyl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein.

The term "aromatic group" as used herein refers to a ring structure having cyclic clouds of delocalized π electrons above and below the plane of the molecule, where the π clouds contain (4n+2) π electrons. A further discussion of aromaticity is found in Morrison and Boyd, Organic Chemistry, (5th Ed., 1987), Chapter 13, entitled "Aromaticity," pages 477-497, incorporated herein by reference. The term "aromatic group" is inclusive of both aryl and heteroaryl groups.

The term "aryl" as used herein is a group that contains any carbon-based aromatic group including, but not limited to, benzene, naphthalene, phenyl, biphenyl, anthracene, and the like. The aryl group can be substituted or unsubstituted. The aryl group can be substituted with one or more groups including, but not limited to, alkyl, cycloalkyl, alkoxy, alkenyl, cycloalkenyl, alkynyl, cycloalkynyl, aryl, heteroaryl, aldehyde, —NH$_2$, carboxylic acid, ester, ether, halide, hydroxy, ketone, azide, nitro, silyl, sulfo-oxo, or thiol as described herein. The term "biaryl" is a specific type of aryl group and is included in the definition of "aryl." In addition, the aryl group can be a single ring structure or comprise multiple ring structures that are either fused ring structures or attached via one or more bridging groups such as a carbon-carbon bond. For example, biaryl can be two aryl groups that are bound together via a fused ring structure, as in naphthalene, or are attached via one or more carbon-carbon bonds, as in biphenyl.

The term "aldehyde" as used herein is represented by the formula —C(O)H. Throughout this specification "C(O)" is a short hand notation for a carbonyl group, i.e., C=O.

The terms "amine" or "amino" as used herein are represented by the formula —NA$^1$A$^2$, where A$^1$ and A$^2$ can be, independently, hydrogen or alkyl, cycloalkyl, alkenyl, cycloalkenyl, alkynyl, cycloalkynyl, aryl, or heteroaryl group as described herein. A specific example of amino is —NH$_2$.

The term "alkylamino" as used herein is represented by the formula —NH(-alkyl) where alkyl is a described herein. Representative examples include, but are not limited to, methylamino group, ethylamino group, propylamino group, isopropylamino group, butylamino group, isobutylamino group, (sec-butyl)amino group, (tert-butyl)amino group, pentylamino group, isopentylamino group, (tert-pentyl)amino group, hexylamino group, and the like.

The term "dialkylamino" as used herein is represented by the formula —N(-alkyl)$_2$ where alkyl is a described herein. Representative examples include, but are not limited to, dimethylamino group, diethylamino group, dipropylamino group, diisopropylamino group, dibutylamino group, diisobutylamino group, di(sec-butyl)amino group, di(tert-butyl)amino group, dipentylamino group, diisopentylamino group, di(tert-pentyl)amino group, dihexylamino group, N-ethyl-N-methylamino group, N-methyl-N-propylamino group, N-ethyl-N-propylamino group and the like.

The term "carboxylic acid" as used herein is represented by the formula —C(O)OH.

The term "ester" as used herein is represented by the formula —OC(O)A$^1$ or —C(O)OA$^1$, where A$^1$ can be alkyl, cycloalkyl, alkenyl, cycloalkenyl, alkynyl, cycloalkynyl, aryl, or heteroaryl group as described herein. The term "polyester" as used herein is represented by the formula -(AO(O)C-A$^2$-C(O)O)$_a$— or -(AO(O)C-A$^2$-OC(O))$_a$—, where A$^1$ and A$^2$ can be, independently, an alkyl, cycloalkyl, alkenyl, cycloalkenyl, alkynyl, cycloalkynyl, aryl, or heteroaryl group described herein and "a" is an integer from 1 to 500. "Polyester" is as the term used to describe a group that is produced by the reaction between a compound having at least two carboxylic acid groups with a compound having at least two hydroxyl groups.

The term "ether" as used herein is represented by the formula $A^1OA^2$, where $A^1$ and $A^2$ can be, independently, an alkyl, cycloalkyl, alkenyl, cycloalkenyl, alkynyl, cycloalkynyl, aryl, or heteroaryl group described herein. The term "polyether" as used herein is represented by the formula $-(A^1O-A^2O)_a-$, where $A^1$ and $A^2$ can be, independently, an alkyl, cycloalkyl, alkenyl, cycloalkenyl, alkynyl, cycloalkynyl, aryl, or heteroaryl group described herein and "a" is an integer of from 1 to 500. Examples of polyether groups include polyethylene oxide, polypropylene oxide, and polybutylene oxide.

The terms "halo," "halogen," or "halide" as used herein can be used interchangeably and refer to F, Cl, Br, or I.

The terms "pseudohalide," "pseudohalogen," or "pseudohalo" as used herein can be used interchangeably and refer to functional groups that behave substantially similar to halides. Such functional groups include, by way of example, cyano, thiocyanato, azido, trifluoromethyl, trifluoromethoxy, perfluoroalkyl, and perfluoroalkoxy groups.

The term "heteroalkyl," as used herein refers to an alkyl group containing at least one heteroatom. Suitable heteroatoms include, but are not limited to, O, N, Si, P and S, wherein the nitrogen, phosphorous and sulfur atoms are optionally oxidized, and the nitrogen heteroatom is optionally quaternized. Heteroalkyls can be substituted as defined above for alkyl groups.

The term "heteroaryl," as used herein refers to an aromatic group that has at least one heteroatom incorporated within the ring of the aromatic group. Examples of heteroatoms include, but are not limited to, nitrogen, oxygen, sulfur, and phosphorus, where N-oxides, sulfur oxides, and dioxides are permissible heteroatom substitutions. The heteroaryl group can be substituted or unsubstituted. The heteroaryl group can be substituted with one or more groups including, but not limited to, alkyl, cycloalkyl, alkoxy, amino, ether, halide, hydroxy, nitro, silyl, sulfo-oxo, or thiol as described herein. Heteroaryl groups can be monocyclic, or alternatively fused ring systems. Heteroaryl groups include, but are not limited to, furyl, imidazolyl, pyrimidinyl, tetrazolyl, thienyl, pyridinyl, pyrrolyl, N-methylpyrrolyl, quinolinyl, isoquinolinyl, pyrazolyl, triazolyl, thiazolyl, oxazolyl, isoxazolyl, oxadiazolyl, thiadiazolyl, isothiazolyl, pyridazinyl, pyrazinyl, benzofuranyl, benzodioxolyl, benzothiophenyl, indolyl, indazolyl, benzimidazolyl, imidazopyridinyl, pyrazolopyridinyl, and pyrazolopyrimidinyl. Further not limiting examples of heteroaryl groups include, but are not limited to, pyridinyl, pyridazinyl, pyrimidinyl, pyrazinyl, thiophenyl, pyrazolyl, imidazolyl, benzo[d]oxazolyl, benzo[d]thiazolyl, quinolinyl, quinazolinyl, indazolyl, imidazo[1,2-b]pyridazinyl, imidazo[1,2-a]pyrazinyl, benzo[c][1,2,5]thiadiazolyl, benzo[c][1,2,5]oxadiazolyl, and pyrido[2,3-b]pyrazinyl.

The terms "heterocycle" or "heterocyclyl," as used herein can be used interchangeably and refer to single and multi-cyclic aromatic or non-aromatic ring systems in which at least one of the ring members is other than carbon. Thus, the term is inclusive of, but not limited to, "heterocycloalkyl", "heteroaryl", "bicyclic heterocycle" and "polycyclic heterocycle." Heterocycle includes pyridine, pyrimidine, furan, thiophene, pyrrole, isoxazole, isothiazole, pyrazole, oxazole, thiazole, imidazole, oxazole, including, 1,2,3-oxadiazole, 1,2,5-oxadiazole and 1,3,4-oxadiazole, thiadiazole, including, 1,2,3-thiadiazole, 1,2,5-thiadiazole, and 1,3,4-thiadiazole, triazole, including, 1,2,3-triazole, 1,3,4-triazole, tetrazole, including 1,2,3,4-tetrazole and 1,2,4,5-tetrazole, pyridazine, pyrazine, triazine, including 1,2,4-triazine and 1,3,5-triazine, tetrazine, including 1,2,4,5-tetrazine, pyrrolidine, piperidine, piperazine, morpholine, azetidine, tetrahydropyran, tetrahydrofuran, dioxane, and the like. The term heterocyclyl group can also be a C2 heterocyclyl, C2-C3 heterocyclyl, C2-C4 heterocyclyl, C2-C5 heterocyclyl, C2-C6 heterocyclyl, C2-C7 heterocyclyl, C2-C8 heterocyclyl, C2-C9 heterocyclyl, C2-C10 heterocyclyl, C2-C11 heterocyclyl, and the like up to and including a C2-C18 heterocyclyl. For example, a C2 heterocyclyl comprises a group which has two carbon atoms and at least one heteroatom, including, but not limited to, aziridinyl, diazetidinyl, dihydrodiazetyl, oxiranyl, thiiranyl, and the like. Alternatively, for example, a C5 heterocyclyl comprises a group which has five carbon atoms and at least one heteroatom, including, but not limited to, piperidinyl, tetrahydropyranyl, tetrahydrothiopyranyl, diazepanyl, pyridinyl, and the like. It is understood that a heterocyclyl group may be bound either through a heteroatom in the ring, where chemically possible, or one of carbons comprising the heterocyclyl ring.

The term "bicyclic heterocycle" or "bicyclic heterocyclyl," as used herein refers to a ring system in which at least one of the ring members is other than carbon. Bicyclic heterocyclyl encompasses ring systems wherein an aromatic ring is fused with another aromatic ring, or wherein an aromatic ring is fused with a non-aromatic ring. Bicyclic heterocyclyl encompasses ring systems wherein a benzene ring is fused to a 5- or a 6-membered ring containing 1, 2 or 3 ring heteroatoms or wherein a pyridine ring is fused to a 5- or a 6-membered ring containing 1, 2 or 3 ring heteroatoms. Bicyclic heterocyclic groups include, but are not limited to, indolyl, indazolyl, pyrazolo[1,5-a]pyridinyl, benzofuranyl, quinolinyl, quinoxalinyl, 1,3-benzodioxolyl, 2,3-dihydro-1,4-benzodioxinyl, 3,4-dihydro-2H-chromenyl, 1H-pyrazolo[4,3-c]pyridin-3-yl; 1H-pyrrolo[3,2-b]pyridin-3-yl; and 1H-pyrazolo[3,2-b]pyridin-3-yl.

The term "heterocycloalkyl" as used herein refers to an aliphatic, partially unsaturated or fully saturated, 3- to 14-membered ring system, including single rings of 3 to 8 atoms and bi- and tricyclic ring systems. The heterocycloalkyl ring-systems include one to four heteroatoms independently selected from oxygen, nitrogen, and sulfur, wherein a nitrogen and sulfur heteroatom optionally can be oxidized and a nitrogen heteroatom optionally can be substituted. Representative heterocycloalkyl groups include, but are not limited to, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, and tetrahydrofuryl.

The term "hydroxyl" or "hydroxyl" as used herein is represented by the formula —OH.

The term "ketone" as used herein is represented by the formula $A^1C(O)A^2$, where $A^1$ and $A^2$ can be, independently, an alkyl, cycloalkyl, alkenyl, cycloalkenyl, alkynyl, cycloalkynyl, aryl, or heteroaryl group as described herein.

The term "azide" or "azido" as used herein is represented by the formula —$N_3$.

The term "nitro" as used herein is represented by the formula —$NO_2$.

The term "nitrile" or "cyano" as used herein is represented by the formula —CN.

The term "silyl" as used herein is represented by the formula —$SiA^1A^2A^3$, where $A^1$, $A^2$, and $A^3$ can be, independently, hydrogen or an alkyl, cycloalkyl, alkoxy, alkenyl, cycloalkenyl, alkynyl, cycloalkynyl, aryl, or heteroaryl group as described herein.

The term "sulfo-oxo" as used herein is represented by the formulas —S(O)A$^1$, —S(O)$_2$A$^1$, —OS(O)$_2$A$^1$, or —OS(O)$_2$OA$^1$, where A$^1$ can be hydrogen or an alkyl, cycloalkyl, alkenyl, cycloalkenyl, alkynyl, cycloalkynyl, aryl, or heteroaryl group as described herein.

Throughout this specification "S(O)" is a short hand notation for S=O. The term "sulfonyl" is used herein to refer to the sulfo-oxo group represented by the formula —S(O)$_2$A$^1$, where A$^1$ can be hydrogen or an alkyl, cycloalkyl, alkenyl, cycloalkenyl, alkynyl, cycloalkynyl, aryl, or heteroaryl group as described herein. The term "sulfone" as used herein is represented by the formula A$^1$S(O)$_2$A$^2$, where A$^1$ and A$^2$ can be, independently, an alkyl, cycloalkyl, alkenyl, cycloalkenyl, alkynyl, cycloalkynyl, aryl, or heteroaryl group as described herein. The term "sulfoxide" as used herein is represented by the formula A$^1$S(O)A$^2$, where A$^1$ and A$^2$ can be, independently, an alkyl, cycloalkyl, alkenyl, cycloalkenyl, alkynyl, cycloalkynyl, aryl, or heteroaryl group as described herein.

The term "thiol" as used herein is represented by the formula —SH.

"R$^1$," "R$^2$," "R$^3$," "R$^n$," where n is an integer, as used herein can, independently, possess one or more of the groups listed above. For example, if R$^1$ is a straight chain alkyl group, one of the hydrogen atoms of the alkyl group can optionally be substituted with a hydroxyl group, an alkoxy group, an alkyl group, a halide, and the like. Depending upon the groups that are selected, a first group can be incorporated within second group or, alternatively, the first group can be pendant (i.e., attached) to the second group. For example, with the phrase "an alkyl group comprising an amino group," the amino group can be incorporated within the backbone of the alkyl group. Alternatively, the amino group can be attached to the backbone of the alkyl group. The nature of the group(s) that is (are) selected will determine if the first group is embedded or attached to the second group.

As described herein, compounds of the invention may contain "optionally substituted" moieties. In general, the term "substituted," whether preceded by the term "optionally" or not, means that one or more hydrogen of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. In is also contemplated that, in certain aspects, unless expressly indicated to the contrary, individual substituents can be further optionally substituted (i.e., further substituted or unsubstituted).

The term "stable," as used herein, refers to compounds that are not substantially altered when subjected to conditions to allow for their production, detection, and, in certain aspects, their recovery, purification, and use for one or more of the purposes disclosed herein.

Suitable monovalent substituents on a substitutable carbon atom of an "optionally substituted" group are independently halogen; —(CH$_2$)$_{0-4}$R$^\circ$; —(CH$_2$)$_{0-4}$OR$^\circ$; —O(CH$_2$)$_{0-4}$R$^\circ$, —O—(CH$_2$)$_{0-4}$C(O)OR$^\circ$; —(CH$_2$)$_{0-4}$CH(OR$^\circ$)$_2$; —(CH$_2$)$_{0-4}$SR$^\circ$; —(CH$_2$)$_{0-4}$Ph, which may be substituted with R$^\circ$; —(CH$_2$)$_{0-4}$O(CH$_2$)$_{0-1}$Ph which may be substituted with R$^\circ$; —CH=CHPh, which may be substituted with R$^\circ$; —(CH$_2$)$_{0-4}$O(CH$_2$)$_{0-1}$-pyridyl which may be substituted with R$^\circ$; —NO$_2$; —CN; —N$_3$; —(CH$_2$)$_{0-4}$N(R$^\circ$)$_2$; —(CH$_2$)$_{0-4}$N(R$^\circ$)C(O)R$^\circ$; —N(R$^\circ$)C(S)R$^\circ$; —(CH$_2$)$_{0-4}$N(R$^\circ$)C(O)NR$^\circ$$_2$; —N(R$^\circ$)C(S)NR$^\circ$$_2$; —(CH$_2$)$_{0-4}$N(R$^\circ$)C(O)OR$^\circ$; —N(R$^\circ$)N(R$^\circ$)C(O)R$^\circ$; —N(R$^\circ$)N(R$^\circ$)C(O)NR$^\circ$$_2$; —N(R$^\circ$)N(R$^\circ$)C(O)OR$^\circ$; —(CH$_2$)$_{0-4}$C(O)R$^\circ$; —C(S)R$^\circ$; —(CH$_2$)$_{0-4}$C(O)OR$^\circ$; —(CH$_2$)$_{0-4}$C(O)SR$^\circ$; —(CH$_2$)$_{0-4}$C(O)OSiR$^\circ$$_3$; —(CH$_2$)$_{0-4}$OC(O)R$^\circ$; —OC(O)(CH$_2$)$_{0-4}$SR—, SC(S)SR$^\circ$; —(CH$_2$)$_{0-4}$SC(O)R$^\circ$; —(CH$_2$)$_{0-4}$C(O)NR$^\circ$$_2$; —C(S)NR$^\circ$$_2$; —C(S)SR$^\circ$; —(CH$_2$)$_{0-4}$OC(O)NR$^\circ$$_2$; —C(O)N(OR$^\circ$)R$^\circ$; —C(O)C(O)R$^\circ$; —C(O)CH$_2$C(O)R$^\circ$; —C(NOR$^\circ$)R$^\circ$; —(CH$_2$)$_{0-4}$SSR$^\circ$; —(CH$_2$)$_{0-4}$S(O)$_2$R$^\circ$; —(CH$_2$)$_{0-4}$S(O)$_2$OR$^\circ$; —(CH$_2$)$_{0-4}$OS(O)$_2$R$^\circ$; —S(O)$_2$NR$^\circ$$_2$; —(CH$_2$)$_{0-4}$S(O)R$^\circ$; —N(R$^\circ$)S(O)$_2$NR$^\circ$$_2$; —N(R$^\circ$)S(O)$_2$R$^\circ$; —N(OR$^\circ$)R$^\circ$; —C(NH)NR$^\circ$$_2$; —P(O)$_2$R$^\circ$; —P(O)R$^\circ$$_2$; —OP(O)R$^\circ$$_2$; —OP(O)(OR$^\circ$)$_2$; SiR$^\circ$$_3$; —(C$_{1-4}$ straight or branched alkylene)O—N(R$^\circ$)$_2$; or —(C$_{1-4}$ straight or branched alkylene)C(O)O—N(R$^\circ$)$_2$, wherein each R$^\circ$ may be substituted as defined below and is independently hydrogen, C$_{1-6}$ aliphatic, —CH$_2$Ph, —O(CH$_2$)$_{0-1}$Ph, —CH$_2$-(5-6 membered heteroaryl ring), or a 5-6-membered saturated, partially unsaturated, or aryl ring having 0-4 heteroatoms independently selected from nitrogen, oxygen, or sulfur, or, notwithstanding the definition above, two independent occurrences of R$^\circ$, taken together with their intervening atom(s), form a 3-12-membered saturated, partially unsaturated, or aryl mono- or bicyclic ring having 0-4 heteroatoms independently selected from nitrogen, oxygen, or sulfur, which may be substituted as defined below.

Suitable monovalent substituents on R$^\circ$ (or the ring formed by taking two independent occurrences of R$^\circ$ together with their intervening atoms), are independently halogen, —(CH$_2$)$_{0-2}$R$^\bullet$, -(haloR$^\bullet$), —(CH$_2$)$_{0-2}$OH, —(CH$_2$)$_{0-2}$OR$^\bullet$, —(CH$_2$)$_{0-2}$CH(OR$^\bullet$)$_2$; —O(haloR$^\bullet$), —CN, —N$_3$, —(CH$_2$)$_{0-2}$C(O)R$^\bullet$, —(CH$_2$)$_{0-2}$C(O)OH, —(CH$_2$)$_{0-2}$C(O)OR$^\bullet$, —(CH$_2$)$_{0-2}$SR$^\bullet$, —(CH$_2$)$_{0-2}$SH, —(CH$_2$)$_{0-2}$NH$_2$, —(CH$_2$)$_{0-2}$NHR$^\bullet$, —(CH$_2$)$_{0-2}$NR$^\bullet$$_2$, —NO$_2$, —SiR$^\bullet$$_3$, —OSiR$^\bullet$$_3$, —C(O)SR$^\bullet$, —(C$_{1-4}$ straight or branched alkylene)C(O)OR$^\bullet$, or —SSR$^\bullet$ wherein each R$^\bullet$ is unsubstituted or where preceded by "halo" is substituted only with one or more halogens, and is independently selected from C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur. Suitable divalent substituents on a saturated carbon atom of R$^\circ$ include =O and =S.

Suitable divalent substituents on a saturated carbon atom of an "optionally substituted" group include the following: =O, =S, =NNR*$_2$, =NNHC(O)R*, =NNHC(O)OR*, =NNHS(O)$_2$R*, =NR*, =NOR*, —O(C(R*$_2$))$_{2-3}$O—, or —S(C(R*$_2$))$_{2-3}$S—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: —O(CR*$_2$)$_{2-3}$O—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of R* include halogen, —R*,-(haloR*), —OH, —OR*, —O(haloR*), —CN, —C(O)OH, —C(O)OR*, —NH$_2$, —NHR*, —NR*$_2$, or —NO$_2$, wherein each R* is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

Suitable substituents on a substitutable nitrogen of an "optionally substituted" group include —R$^\dagger$, —NR$^\dagger$$_2$, —C(O)R$^\dagger$, —C(O)OR$^\dagger$, —C(O)C(O)R$^\dagger$, —C(O)CH$_2$C(O)R$^\dagger$, —S(O)$_2$R$^\dagger$, —S(O)$_2$NR$^\dagger$$_2$, —C(S)NR$^\dagger$$_2$, —C(NH)NR$^\dagger$$_2$, or —N(R$^\dagger$)S(O)$_2$R$^\dagger$; wherein each R$^\dagger$ is independently hydrogen, C$_{1-6}$ aliphatic which may be substituted as defined below, unsubstituted —OPh, or an unsubstituted 5-6-membered saturated, partially unsaturated, or aryl ring having 0-4 heteroatoms independently selected from nitrogen, oxygen, or sulfur, or, notwithstanding the definition above, two independent occurrences of R$^\dagger$, taken together with their intervening atom(s) form an unsubstituted 3-12-membered saturated, partially unsaturated, or aryl mono- or bicyclic ring having 0-4 heteroatoms independently selected from nitrogen, oxygen, or sulfur.

Suitable substituents on the aliphatic group of R$^\dagger$ are independently halogen, —R*, -(haloR*), —OH, —OR*, —O(haloR*), —CN, —C(O)OH, —C(O)OR*, —NH$_2$, —NHR*, —NR*$_2$, or —NO$_2$, wherein each R* is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

The term "leaving group" refers to an atom (or a group of atoms) with electron withdrawing ability that can be displaced as a stable species, taking with it the bonding electrons. Examples of suitable leaving groups include halides and sulfonate esters, including, but not limited to, triflate, mesylate, tosylate, and brosylate.

The terms "hydrolysable group" and "hydrolysable moiety" refer to a functional group capable of undergoing hydrolysis, e.g., under basic or acidic conditions. Examples of hydrolysable residues include, without limitation, acid halides, activated carboxylic acids, and various protecting groups known in the art (see, for example, "Protective Groups in Organic Synthesis," T. W. Greene, P. G. M. Wuts, Wiley-Interscience, 1999).

The term "organic residue" defines a carbon-containing residue, i.e., a residue comprising at least one carbon atom, and includes but is not limited to the carbon-containing groups, residues, or radicals defined hereinabove. Organic residues can contain various heteroatoms, or be bonded to another molecule through a heteroatom, including oxygen, nitrogen, sulfur, phosphorus, or the like. Examples of organic residues include but are not limited alkyl or substituted alkyls, alkoxy or substituted alkoxy, mono or di-substituted amino, amide groups, etc. Organic residues can preferably comprise 1 to 18 carbon atoms, 1 to 15, carbon atoms, 1 to 12 carbon atoms, 1 to 8 carbon atoms, 1 to 6 carbon atoms, or 1 to 4 carbon atoms. In a further aspect, an organic residue can comprise 2 to 18 carbon atoms, 2 to 15, carbon atoms, 2 to 12 carbon atoms, 2 to 8 carbon atoms, 2 to 4 carbon atoms, or 2 to 4 carbon atoms.

A very close synonym of the term "residue" is the term "radical," which as used in the specification and concluding claims, refers to a fragment, group, or substructure of a molecule described herein, regardless of how the molecule is prepared. For example, a 2,4-thiazolidinedione radical in a particular compound has the structure:

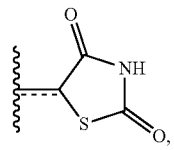

regardless of whether thiazolidinedione is used to prepare the compound. In some embodiments the radical (for example an alkyl) can be further modified (i.e., substituted alkyl) by having bonded thereto one or more "substituent radicals." The number of atoms in a given radical is not critical to the present invention unless it is indicated to the contrary elsewhere herein.

"Organic radicals," as the term is defined and used herein, contain one or more carbon atoms. An organic radical can have, for example, 1-26 carbon atoms, 1-18 carbon atoms, 1-12 carbon atoms, 1-8 carbon atoms, 1-6 carbon atoms, or 1-4 carbon atoms. In a further aspect, an organic radical can have 2-26 carbon atoms, 2-18 carbon atoms, 2-12 carbon atoms, 2-8 carbon atoms, 2-6 carbon atoms, or 2-4 carbon atoms. Organic radicals often have hydrogen bound to at least some of the carbon atoms of the organic radical. One example, of an organic radical that comprises no inorganic atoms is a 5, 6, 7, 8-tetrahydro-2-naphthyl radical. In some embodiments, an organic radical can contain 1-10 inorganic heteroatoms bound thereto or therein, including halogens, oxygen, sulfur, nitrogen, phosphorus, and the like. Examples of organic radicals include but are not limited to an alkyl, substituted alkyl, cycloalkyl, substituted cycloalkyl, mono-substituted amino, di-substituted amino, acyloxy, cyano, carboxy, carboalkoxy, alkylcarboxamide, substituted alkylcarboxamide, dialkylcarboxamide, substituted dialkylcarboxamide, alkylsulfonyl, alkylsulfinyl, thioalkyl, thiohaloalkyl, alkoxy, substituted alkoxy, haloalkyl, haloalkoxy, aryl, substituted aryl, heteroaryl, heterocyclic, or substituted heterocyclic radicals, wherein the terms are defined elsewhere herein. A few non-limiting examples of organic radicals that include heteroatoms include alkoxy radicals, trifluoromethoxy radicals, acetoxy radicals, dimethylamino radicals and the like.

Compounds described herein can contain one or more double bonds and, thus, potentially give rise to cis/trans (E/Z) isomers, as well as other conformational isomers. Unless stated to the contrary, the invention includes all such possible isomers, as well as mixtures of such isomers.

Unless stated to the contrary, a formula with chemical bonds shown only as solid lines and not as wedges or dashed lines contemplates each possible isomer, e.g., each enantiomer and diastereomer, and a mixture of isomers, such as a racemic or scalemic mixture. Compounds described herein can contain one or more asymmetric centers and, thus, potentially give rise to diastereomers and optical isomers. Unless stated to the contrary, the present invention includes all such possible diastereomers as well as their racemic mixtures, their substantially pure resolved enantiomers, all possible geometric isomers, and pharmaceutically acceptable salts thereof. Mixtures of stereoisomers, as well as isolated specific stereoisomers, are also included. During the course of the synthetic procedures used to prepare such compounds, or in using racemization or epimerization procedures known to those skilled in the art, the products of such procedures can be a mixture of stereoisomers.

Many organic compounds exist in optically active forms having the ability to rotate the plane of plane-polarized light. In describing an optically active compound, the prefixes D and L or R and S are used to denote the absolute configuration of the molecule about its chiral center(s). The prefixes d and l or (+) and (−) are employed to designate the sign of rotation of plane-polarized light by the compound, with (−) or meaning that the compound is levorotatory. A compound prefixed with (+) or d is dextrorotatory. For a given chemical structure, these compounds, called stereoisomers, are identical except that they are non-superimposable mirror images of one another. A specific stereoisomer can also be referred to as an enantiomer, and a mixture of such isomers is often called an enantiomeric mixture. A 50:50 mixture of enantiomers is referred to as a racemic mixture. Many of the compounds described herein can have one or more chiral centers and therefore can exist in different enantiomeric forms. If desired, a chiral carbon can be designated with an asterisk (*). When bonds to the chiral carbon are depicted as straight lines in the disclosed formulas, it is understood that both the (R) and (S) configurations of the chiral carbon, and hence both enantiomers and mixtures thereof, are embraced within the formula. As is used in the art, when it is desired to specify the absolute configuration about a chiral carbon, one of the bonds to the chiral carbon can be depicted as a wedge (bonds to atoms above the plane) and the other can be depicted as a series or wedge of short parallel lines is (bonds to atoms below the plane). The Cahn-Ingold-Prelog system can be used to assign the (R) or (S) configuration to a chiral carbon.

When the disclosed compounds contain one chiral center, the compounds exist in two enantiomeric forms. Unless specifically stated to the contrary, a disclosed compound includes both enantiomers and mixtures of enantiomers, such as the specific 50:50 mixture referred to as a racemic mixture. The enantiomers can be resolved by methods known to those skilled in the art, such as formation of diastereoisomeric salts which may be separated, for example, by crystallization (see, CRC Handbook of Optical Resolutions via Diastereomeric Salt Formation by David Kozma (CRC Press, 2001)); formation of diastereoisomeric derivatives or complexes which may be separated, for example, by crystallization, gas-liquid or liquid chromatography; selective reaction of one enantiomer with an enantiomer-specific reagent, for example enzymatic esterification; or gas-liquid or liquid chromatography in a chiral environment, for example on a chiral support for example silica with a bound chiral ligand or in the presence of a chiral solvent. It will be appreciated that where the desired enantiomer is converted into another chemical entity by one of the separation procedures described above, a further step can liberate the desired enantiomeric form. Alternatively, specific enantiomers can be synthesized by asymmetric synthesis using optically active reagents, substrates, catalysts or solvents, or by converting one enantiomer into the other by asymmetric transformation.

Designation of a specific absolute configuration at a chiral carbon in a disclosed compound is understood to mean that the designated enantiomeric form of the compounds can be provided in enantiomeric excess (e.e.). Enantiomeric excess, as used herein, is the presence of a particular enantiomer at greater than 50%, for example, greater than 60%, greater than 70%, greater than 75%, greater than 80%, greater than 85%, greater than 90%, greater than 95%, greater than 98%, or greater than 99%. In one aspect, the designated enantiomer is substantially free from the other enantiomer. For example, the "R" forms of the compounds can be substantially free from the "S" forms of the compounds and are, thus, in enantiomeric excess of the "S" forms. Conversely, "S" forms of the compounds can be substantially free of "R" forms of the compounds and are, thus, in enantiomeric excess of the "R" forms.

When a disclosed compound has two or more chiral carbons, it can have more than two optical isomers and can exist in diastereoisomeric forms. For example, when there are two chiral carbons, the compound can have up to four optical isomers and two pairs of enantiomers ((S,S)/(R,R) and (R,S)/(S,R)). The pairs of enantiomers (e.g., (S,S)/(R,R)) are mirror image stereoisomers of one another. The stereoisomers that are not mirror-images (e.g., (S,S) and (R,S)) are diastereomers. The diastereoisomeric pairs can be separated by methods known to those skilled in the art, for example chromatography or crystallization and the individual enantiomers within each pair may be separated as described above. Unless otherwise specifically excluded, a disclosed compound includes each diastereoisomer of such compounds and mixtures thereof.

The compounds according to this disclosure may form prodrugs at hydroxyl or amino functionalities using alkoxy, amino acids, etc., groups as the prodrug forming moieties. For instance, the hydroxymethyl position may form mono-, di-, or triphosphates and again these phosphates can form prodrugs. Preparations of such prodrug derivatives are discussed in various literature sources (examples are: Alexander et al., J. Med. Chem. 1988, 31, 318; Aligas-Martin et al., PCT WO 2000/041531, p. 30). The nitrogen function converted in preparing these derivatives is one (or more) of the nitrogen atoms of a compound of the disclosure.

"Derivatives" of the compounds disclosed herein are pharmaceutically acceptable salts, prodrugs, deuterated forms, radio-actively labeled forms, isomers, solvates and combinations thereof. The "combinations" mentioned in this context refer to derivatives falling within at least two of the groups: pharmaceutically acceptable salts, prodrugs, deuterated forms, radio-actively labeled forms, isomers, and solvates. Examples of radio-actively labeled forms include compounds labeled with tritium, phosphorous-32, iodine-129, carbon-11, fluorine-18, and the like.

Compounds described herein comprise atoms in both their natural isotopic abundance and in non-natural abundance. The disclosed compounds can be isotopically-labeled or isotopically-substituted compounds identical to those described, but for the fact that one or more atoms are replaced by an atom having an atomic mass or mass number different from the atomic mass or mass number typically found in nature. Examples of isotopes that can be incorporated into compounds of the invention include isotopes of hydrogen, carbon, nitrogen, oxygen, phosphorous, fluorine and chlorine, such as $^2H$, $^3H$, $^{13}C$, $^{14}C$, $^{15}N$, $^{18}O$, $^{17}O$, $^{35}S$, $^{18}F$ and $^{36}Cl$, respectively. Compounds further comprise prodrugs thereof, and pharmaceutically acceptable salts of said compounds or of said prodrugs which contain the aforementioned isotopes and/or other isotopes of other atoms are within the scope of this invention. Certain isotopically-labeled compounds of the present invention, for example those into which radioactive isotopes such as $^3H$ and $^{14}C$ are incorporated, are useful in drug and/or substrate tissue distribution assays. Tritiated, i.e., $^3H$, and carbon-14, i.e., $^{14}C$, isotopes are particularly preferred for their ease of preparation and detectability. Further, substitution with heavier isotopes such as deuterium, i.e., $^2H$, can afford certain therapeutic advantages resulting from greater metabolic stability, for example increased in vivo half-life or reduced dosage requirements and, hence, may be preferred in some circumstances. Isotopically labeled compounds of the present invention and prodrugs thereof can generally be prepared by carrying out the procedures below, by substituting a readily available isotopically labeled reagent for a non-isotopically labeled reagent.

The compounds described in the invention can be present as a solvate. In some cases, the solvent used to prepare the solvate is an aqueous solution, and the solvate is then often referred to as a hydrate. The compounds can be present as a hydrate, which can be obtained, for example, by crystallization from a solvent or from aqueous solution. In this connection, one, two, three or any arbitrary number of solvent or water molecules can combine with the compounds according to the invention to form solvates and hydrates. Unless stated to the contrary, the invention includes all such possible solvates.

The term "co-crystal" means a physical association of two or more molecules which owe their stability through non-covalent interaction. One or more components of this molecular complex provide a stable framework in the crystalline lattice. In certain instances, the guest molecules are incorporated in the crystalline lattice as anhydrates or solvates, see e.g. "Crystal Engineering of the Composition of Pharmaceutical Phases. Do Pharmaceutical Co-crystals Represent a New Path to Improved Medicines?" Almarasson, O., et. al., The Royal Society of Chemistry, 1889-1896, 2004. Examples of co-crystals include p-toluenesulfonic acid and benzenesulfonic acid.

It is also appreciated that certain compounds described herein can be present as an equilibrium of tautomers. For example, ketones with an α-hydrogen can exist in an equilibrium of the keto form and the enol form.

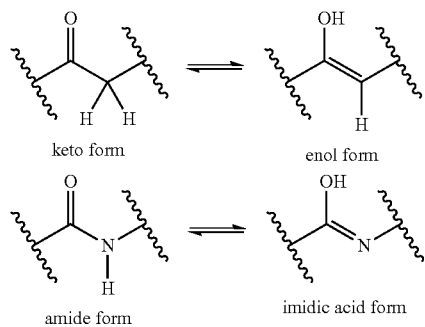

keto form    enol form
amide form    imidic acid form

Likewise, amides with an N-hydrogen can exist in an equilibrium of the amide form and the imidic acid form. As another example, pyrazoles can exist in two tautomeric forms, $N^1$-unsubstituted, $3-A^3$ and $N^1$-unsubstituted, $5-A^3$ as shown below.

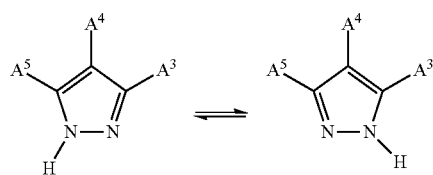

Unless stated to the contrary, the invention includes all such possible tautomers.

It is known that chemical substances form solids, which are present in different states of order which are termed polymorphic forms or modifications. The different modifications of a polymorphic substance can differ greatly in their physical properties. The compounds according to the invention can be present in different polymorphic forms, with it being possible for particular modifications to be metastable. Unless stated to the contrary, the invention includes all such possible polymorphic forms.

In some aspects, a structure of a compound can be represented by a formula:

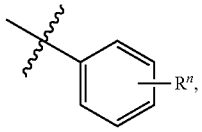

which is understood to be equivalent to a formula:

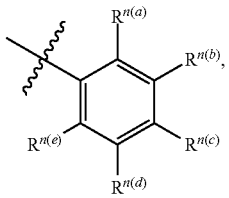

wherein n is typically an integer. That is, R is understood to represent five independent substituents, $R^{n(a)}$, $R^{n(b)}$, $R^{n(c)}$, $R^{n(d)}$, $R^{n(e)}$. By "independent substituents," it is meant that each R substituent can be independently defined. For example, if in one instance $R^{n(a)}$ is halogen, then $R^{n(b)}$ is not necessarily halogen in that instance.

Certain materials, compounds, compositions, and components disclosed herein can be obtained commercially or readily synthesized using techniques generally known to those of skill in the art. For example, the starting materials and reagents used in preparing the disclosed compounds and compositions are either available from commercial suppliers such as Aldrich Chemical Co., (Milwaukee, Wis.), Acros Organics (Morris Plains, N.J.), Strem Chemicals (Newburyport, Mass.), Fisher Scientific (Pittsburgh, Pa.), or Sigma (St. Louis, Mo.) or are prepared by methods known to those skilled in the art following procedures set forth in references such as Fieser and Fieser's Reagents for Organic Synthesis, Volumes 1-17 (John Wiley and Sons, 1991); Rodd's Chemistry of Carbon Compounds, Volumes 1-5 and supplemental volumes (Elsevier Science Publishers, 1989); Organic Reactions, Volumes 1-40 (John Wiley and Sons, 1991); March's Advanced Organic Chemistry, (John Wiley and Sons, 4th Edition); and Larock's Comprehensive Organic Transformations (VCH Publishers Inc., 1989).

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that an order be inferred, in any respect. This holds for any possible non-express basis for interpretation, including: matters of logic with respect to arrangement of steps or operational flow; plain meaning derived from grammatical organization or punctuation; and the number or type of embodiments described in the specification.

Disclosed are the components to be used to prepare the compositions of the invention as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds cannot be explicitly disclosed, each is specifically contemplated and described herein. For example, if a particular compound is disclosed and discussed and a number of modifications that can be made to a number of molecules including the compounds are discussed, specifically contemplated is each and every combination and permutation of the compound and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the compositions of the invention. Thus, if there are a variety of additional steps that can be performed it is understood that each of these additional steps can be performed with any specific embodiment or combination of embodiments of the methods of the invention.

It is understood that the compounds and compositions disclosed herein have certain functions. Disclosed herein are certain structural requirements for performing the disclosed functions, and it is understood that there are a variety of structures that can perform the same function that are related to the disclosed structures, and that these structures will typically achieve the same result.

B. Thioquinolinones

In one aspect, the invention relates to thioquinolinones useful in preventing and treating disorders associated with heme oxygenase-1 (HO-1) signaling such as, for example, kidney diseases including, but not limited to, chronic kidney disease and acute kidney injury.

In one aspect, the compounds of the invention are useful in the treatment of kidney diseases, as further described herein.

It is contemplated that each disclosed derivative can be optionally further substituted. It is also contemplated that any one or more derivative can be optionally omitted from the invention. It is understood that a disclosed compound can be provided by the disclosed methods. It is also understood that the disclosed compounds can be employed in the disclosed methods of using.

1. Structure

In one aspect, disclosed are compounds having a structure represented by a formula:

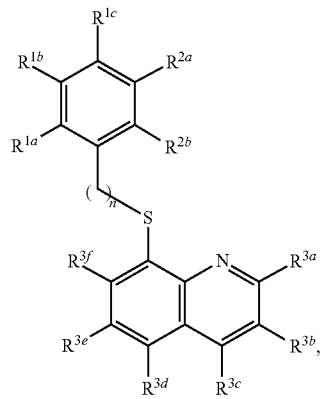

wherein n is 1 or 2; wherein each of $R^{1a}$, $R^{1b}$, and $R^{1c}$ is independently selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl, provided that at least one of $R^{1a}$, $R^{1b}$, and $R^{1c}$ is —OH, C1-C4 alkoxy, or C1-C4 alkylamino; wherein each of $R^{2a}$ and $R^{2b}$ is independently selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; and wherein each of $R^{3a}$, $R^{3b}$, $R^{3c}$, $R^{3d}$, $R^{3e}$, and $R^{3f}$ is independently selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl, provided that at least two of $R^{1a}$, $R^{1b}$, $R^{1c}$, $R^{2a}$, and $R^{2b}$ are non-hydrogen groups, and provided that when n is 1, Z is —S—, and $R^{1a}$ is —OH or C1-C4 alkoxy, then exactly two of $R^{1a}$, $R^{1b}$, $R^{1c}$, $R^{2a}$, and $R^{2b}$ are non-hydrogen groups, or a pharmaceutically acceptable salt thereof.

In one aspect, disclosed are compounds having a structure represented by a formula:

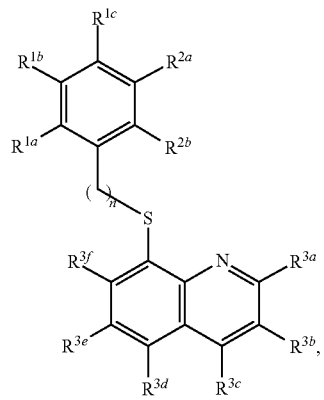

wherein n is 1 or 2; wherein each of $R^{1a}$, $R^{1b}$, and $R^{1c}$ is independently selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl, provided that at least one of $R^{1a}$, $R^{1b}$, and $R^{1c}$ is —OH, C1-C4 alkoxy, or C1-C4 alkylamino; wherein each of $R^{2a}$ and $R^{2b}$ is independently selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; and wherein each of $R^{3a}$, $R^{3b}$, $R^{3c}$, $R^{3d}$, $R^{3e}$, and $R^{3f}$ is independently selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl, provided that at least two of $R^{1a}$, $R^{1b}$, $R^{1c}$, $R^{2a}$, and $R^{2b}$ are non-hydrogen groups, and provided that when n is 1, Z is —S—, and $R^{1a}$ is —OH or C1-C4 alkoxy, then exactly two of $R^{1a}$, $R^{1b}$, $R^{1c}$, $R^{2a}$, and $R^{2b}$ are non-hydrogen groups, or a pharmaceutically acceptable salt thereof.

In one aspect, disclosed are compounds having a structure selected from:

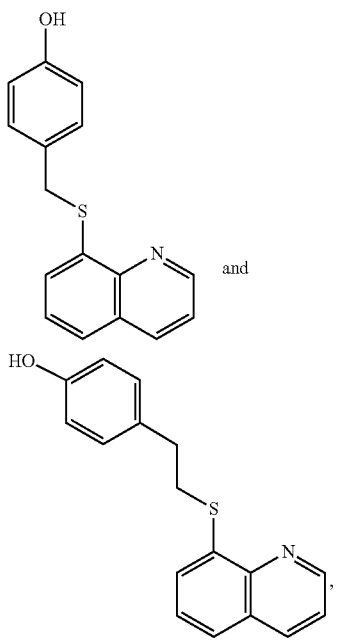

or a pharmaceutically acceptable salt thereof.

In various aspects, the compound has a structure represented by a formula:

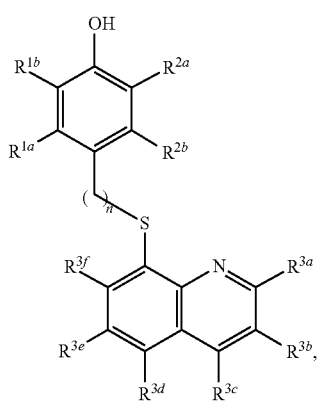

In various aspects, the compound has a structure represented by a formula:

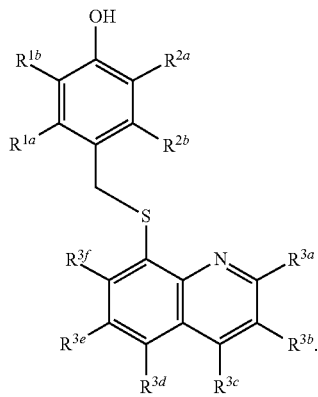

In various aspects, the compound has a structure represented by a formula:

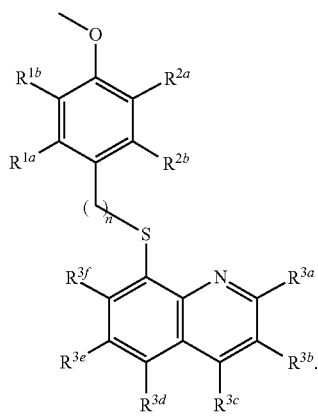

In various aspects, the compound has a structure represented by a formula:

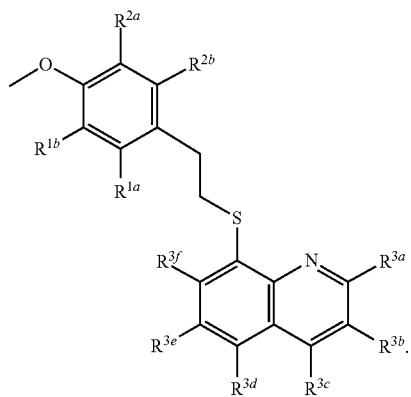

In various aspects, the compound has a structure represented by a formula:

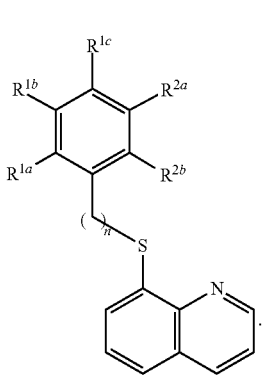

In various aspects, the compound has a structure represented by a formula:

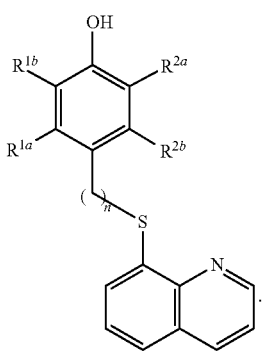

In various aspects, the compound has a structure represented by a formula:

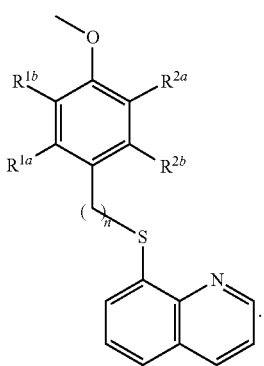

In various aspects, at least two of $R^{1a}$, $R^{1b}$, $R^{1c}$, $R^{2a}$, and $R^{2b}$ are non-hydrogen groups.

In various aspects, when n is 1, Z is —S—, and $R^{1a}$ is —OH or C1-C4 alkoxy, then exactly two of $R^{1a}$, $R^{1b}$, $R^{1c}$, $R^{2a}$, and $R^{2b}$ are non-hydrogen groups, In various aspects, the compound is not:

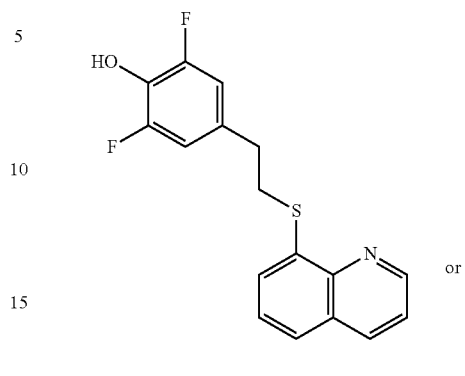

or

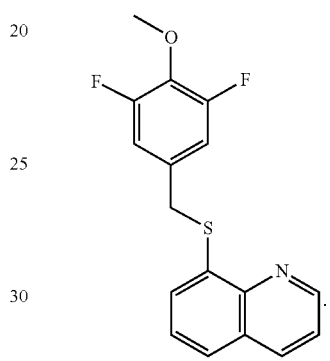

In various aspects, the compound is selected from:

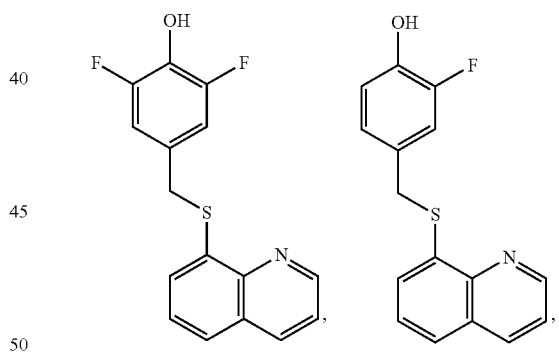

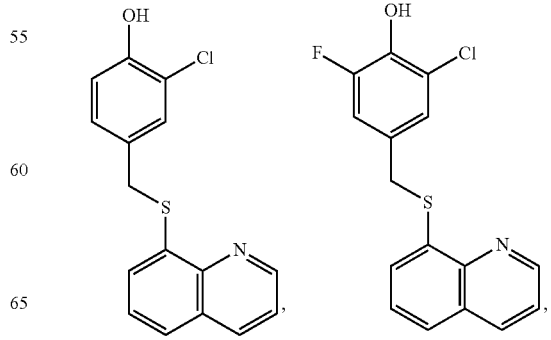

-continued

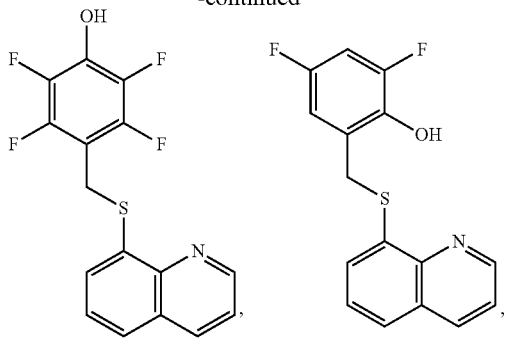

and

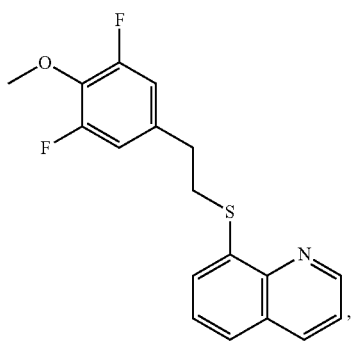

or a pharmaceutically acceptable salt thereof.

In various aspects, n is 1 or 2. In a still further aspect, n is 1. In yet a further aspect, n is 2.

a. $R^{1a}$, $R^{1b}$, AND $R^{1c}$ Groups

In one aspect, each of $R^{1a}$, $R^{1b}$, and $R^{1c}$ is independently selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl, provided that at least one of $R^{1a}$, $R^{1b}$, and $R^{1c}$ is —OH, C1-C4 alkoxy, or C1-C4 alkylamino. In a further aspect, each of $R^{1a}$, $R^{1b}$, and $R^{1c}$ is independently selected from hydrogen, —F, —Cl, —CN, —NH$_2$, —OH, —NO$_2$, methyl, ethyl, n-propyl, isopropyl, ethenyl, propenyl, —CCl$_3$, —CF$_3$, —CHCl$_2$, —CHF$_2$, —CH$_2$Cl, —CH$_2$F, —CH$_2$CH$_2$Cl, —CH$_2$CH$_2$F, —CH$_2$CH$_2$CH$_2$Cl, —CH$_2$CH$_2$CH$_2$F, —CH(CH$_3$)CH$_2$Cl, —CH(CH$_3$)CH$_2$F, —CH$_2$CN, —CH$_2$CH$_2$CN, —CH$_2$CH$_2$CH$_2$CN, —CH(CH$_3$)CH$_2$CN, —CH$_2$OH, —CH$_2$CH$_2$OH, —CH$_2$CH$_2$CH$_2$OH, —CH(CH$_3$)CH$_2$OH, —OCCl$_3$, —OCF$_3$, —OCHCl$_2$, —OCHF$_2$, —OCH$_2$Cl, —OCH$_2$F, —OCH$_2$CH$_2$Cl, —OCH$_2$CH$_2$F, —OCH$_2$CH$_2$CH$_2$Cl, —OCH$_2$CH$_2$CH$_2$F, —OCH(CH$_3$)CH$_2$Cl, —OCH(CH$_3$)CH$_2$F, —OCH$_3$, —OCH$_2$CH$_3$, —OCH$_2$CH$_2$CH$_3$, —OCH(CH$_3$)$_2$, —NHCH$_3$, —NHCH$_2$CH$_3$, —NHCH$_2$CH$_2$CH$_3$, —NHCH(CH$_3$)$_2$, —N(CH$_3$)$_2$, —N(CH$_3$)CH$_2$CH$_3$, —N(CH$_2$CH$_3$)CH$_2$CH$_2$CH$_3$, —N(CH$_3$)CH(CH$_3$)$_2$, —CH$_2$NH$_2$, —CH$_2$CH$_2$NH$_2$, —CH$_2$CH$_2$CH$_2$NH$_2$, and —CH(CH$_3$)CH$_2$NH$_2$. In a still further aspect, each of $R^{1a}$, $R^{1b}$, and $R^{1c}$ is independently selected from hydrogen, —F, —Cl, —CN, —NH$_2$, —OH, methyl, ethyl, ethenyl, —CCl$_3$, —CF$_3$, —CHCl$_2$, —CHF$_2$, —CH$_2$Cl, —CH$_2$F, —CH$_2$CH$_2$Cl, —CH$_2$CH$_2$F, —CH$_2$CN, —CH$_2$CH$_2$CN, —CH$_2$OH, —CH$_2$CH$_2$OH, —OCCl$_3$, —OCF$_3$, —OCHCl$_2$, —OCHF$_2$, —OCH$_2$Cl, —OCH$_2$F, —OCH$_2$CH$_2$Cl, —OCH$_2$CH$_2$F, —OCH$_3$, —OCH$_2$CH$_3$, —NHCH$_3$, —NHCH$_2$CH$_3$, —N(CH$_3$)$_2$, —N(CH$_3$)CH$_2$CH$_3$, —CH$_2$NH$_2$, and —CH$_2$CH$_2$NH$_2$. In yet a further aspect, each of $R^{1a}$, $R^{1b}$, and $R^{1c}$ is independently selected from hydrogen, —F, —Cl, —CN, —NH$_2$, —OH, —NO$_2$, methyl, —CCl$_3$, —CF$_3$, —CHCl$_2$, —CHF$_2$, —CH$_2$Cl, —CH$_2$F, —CH$_2$CN, —CH$_2$OH, —OCCl$_3$, —OCF$_3$, —OCHCl$_2$, —OCHF$_2$, —OCH$_2$Cl, —OCH$_2$F, —OCH$_3$, —NHCH$_3$, —N(CH$_3$)$_2$, and —CH$_2$NH$_2$.

In various aspects, each of $R^{1a}$, $R^{1b}$, and $R^{1c}$ is independently selected from hydrogen, halogen, —CN, —NH$_2$, —OH, —NO$_2$, C1-C4 alkyl, and C2-C4 alkenyl. In a further aspect, each of $R^{1a}$, $R^{1b}$, and $R^{1c}$ is independently selected from hydrogen, —F, —Cl, —CN, —NH$_2$, —OH, —NO$_2$, methyl, ethyl, n-propyl, isopropyl, ethenyl, and propenyl. In a still further aspect, each of $R^{1a}$, $R^{1b}$, and $R^{1c}$ is independently selected from hydrogen, —F, —Cl, —CN, —NH$_2$, —OH, —NO$_2$, methyl, ethyl, and ethenyl. In yet a further aspect, each of $R^{1a}$, $R^{1b}$ and $R^{1c}$ is independently selected from hydrogen, —F, —Cl, —CN, —NH$_2$, —OH, —NO$_2$, and methyl.

In various aspects, each of $R^{1a}$, $R^{1b}$, and $R^{1c}$ is independently selected from hydrogen, C1-C4 alkyl, and C2-C4 alkenyl. In a further aspect, each of $R^{1a}$, $R^{1b}$, and $R^{1c}$ is independently selected from hydrogen, methyl, ethyl, n-propyl, isopropyl, ethenyl, and propenyl. In a still further aspect, each of $R^{1a}$, $R^{1b}$, and $R^{1c}$ is independently selected from hydrogen, methyl, ethyl, and ethenyl. In yet a further aspect, each of $R^{1a}$, $R^{1b}$, and $R^{1c}$ is independently selected from hydrogen and methyl.

In various aspects, each of $R^{1a}$, $R^{1b}$, and $R^{1c}$ is independently selected from hydrogen, halogen, —CN, —NH$_2$, —OH, —NO$_2$, C1-C4 haloalkyl, and C1-C4 cyanoalkyl. In a further aspect, each of $R^{1a}$, $R^{1b}$, and $R^{1c}$ is independently selected from hydrogen, —F, —Cl, —CN, —NH$_2$, —OH, —NO$_2$, —CCl$_3$, —CF$_3$, —CHCl$_2$, —CHF$_2$, —CH$_2$Cl, —CH$_2$F, —CH$_2$CH$_2$Cl, —CH$_2$CH$_2$F, —CH$_2$CH$_2$CH$_2$Cl, —CH$_2$CH$_2$CH$_2$F, —CH(CH$_3$)CH$_2$Cl, —CH(CH$_3$)CH$_2$F, —CH$_2$CN, —CH$_2$CH$_2$CN, —CH$_2$CH$_2$CH$_2$CN, and —CH(CH$_3$)CH$_2$CN. In a still further aspect, each of $R^{1a}$, $R^{1b}$, and $R^{1c}$ is independently selected from hydrogen, —F, —Cl, —CN, —NH$_2$, —OH, —NO$_2$, —CCl$_3$, —CF$_3$, —CHCl$_2$, —CHF$_2$, —CH$_2$Cl, —CH$_2$F, —CH$_2$CH$_2$Cl, —CH$_2$CH$_2$F, —CH$_2$CN, and —CH$_2$CH$_2$CN. In yet a further aspect, each of $R^{1a}$, $R^{1b}$, and $R^{1c}$ is independently selected from hydrogen, —F, —Cl, —CN, —NH$_2$, —OH, —NO$_2$, —CCl$_3$, —CF$_3$, —CHCl$_2$, —CHF$_2$, —CH$_2$Cl, —CH$_2$F, and —CH$_2$CN.

In various aspects, each of $R^{1a}$, $R^{1b}$, and $R^{1c}$ is independently selected from hydrogen, C1-C4 haloalkyl, and C1-C4 cyanoalkyl. In a further aspect, each of $R^{1a}$, $R^{1b}$, and $R^{1c}$ is independently selected from hydrogen, —CCl$_3$, —CF$_3$, —CHCl$_2$, —CHF$_2$, —CH$_2$Cl, —CH$_2$F, —CH$_2$CH$_2$Cl, —CH$_2$CH$_2$F, —CH$_2$CH$_2$CH$_2$Cl, —CH$_2$CH$_2$CH$_2$F, —CH(CH$_3$)CH$_2$Cl, —CH(CH$_3$)CH$_2$F, —CH$_2$CN, —CH$_2$CH$_2$CN, —CH$_2$CH$_2$CH$_2$CN, and —CH(CH$_3$)CH$_2$CN. In a still further aspect, each of $R^{1a}$, $R^{1b}$, and $R^{1c}$ is independently selected from hydrogen, —CCl$_3$, —CF$_3$, —CHCl$_2$, —CHF$_2$, —CH$_2$Cl, —CH$_2$F, —CH$_2$CH$_2$Cl, —CH$_2$CH$_2$F, —CH$_2$CN, and —CH$_2$CH$_2$CN. In yet a further aspect, each of $R^{1a}$, $R^{1b}$, and $R^{1c}$ is independently selected from hydrogen, —CCl$_3$, —CF$_3$, —CHCl$_2$, —CHF$_2$, —CH$_2$Cl, —CH$_2$F, and —CH$_2$CN.

In various aspects, each of $R^{1a}$, $R^{1b}$, and $R^{1c}$ is independently selected from hydrogen, halogen, —CN, —NH$_2$, —OH, —NO$_2$, C1-C4 hydroxyalkyl, C1-C4 haloalkoxy, and C1-C4 alkoxy. In a further aspect, each of $R^{1a}$, $R^{1b}$, and $R^{1c}$ is independently selected from hydrogen, —F, —Cl, —CN, —NH$_2$, —OH, —NO$_2$, —CH$_2$OH, —CH$_2$CH$_2$OH, —CH$_2$CH$_2$CH$_2$OH, —CH(CH$_3$)CH$_2$OH, —OCCl$_3$, —OCF$_3$, —OCHCl$_2$, —OCHF$_2$, —OCH$_2$Cl, —OCH$_2$F, —OCH$_2$CH$_2$Cl, —OCH$_2$CH$_2$F, —OCH$_2$CH$_2$CH$_2$Cl, —OCH$_2$CH$_2$CH$_2$F, —OCH(CH$_3$)CH$_2$Cl, —OCH(CH$_3$)CH$_2$F, —OCH$_3$, —OCH$_2$CH$_3$, —OCH$_2$CH$_2$CH$_3$, and —OCH(CH$_3$)$_2$. In a still further aspect, each of R$^{1a}$, R$^{1b}$, and R$^{1c}$ is independently selected from hydrogen, —F, —Cl, —CN, —NH$_2$, —OH, —NO$_2$, —CH$_2$OH, —CH$_2$CH$_2$OH, —OCCl$_3$, —OCF$_3$, —OCHCl$_2$, —OCHF$_2$, —OCH$_2$Cl, —OCH$_2$F, —OCH$_2$CH$_2$Cl, —OCH$_2$CH$_2$F, —OCH$_3$, and —OCH$_2$CH$_3$. In yet a further aspect, each of R$^{1a}$, R$^{1b}$, and R$^{1c}$ is independently selected from hydrogen, —F, —Cl, —CN, —NH$_2$, —OH, —NO$_2$, —CH$_2$OH, —OCCl$_3$, —OCF$_3$, —OCHCl$_2$, —OCHF$_2$, —OCH$_2$Cl, —OCH$_2$F, and —OCH$_3$.

In various aspects, each of R$^{1a}$, R$^{1b}$, and R$^{1c}$ is independently selected from hydrogen, C1-C4 hydroxyalkyl, C1-C4 haloalkoxy, and C1-C4 alkoxy. In a further aspect, each of R$^{1a}$, R$^{1b}$, and R$^{1c}$ is independently selected from hydrogen, —CH$_2$OH, —CH$_2$CH$_2$OH, —CH$_2$CH$_2$CH$_2$OH, —CH(CH$_3$)CH$_2$OH, —OCCl$_3$, —OCF$_3$, —OCHCl$_2$, —OCHF$_2$, —OCH$_2$Cl, —OCH$_2$F, —OCH$_2$CH$_2$Cl, —OCH$_2$CH$_2$F, —OCH$_2$CH$_2$CH$_2$Cl, —OCH$_2$CH$_2$CH$_2$F, —OCH(CH$_3$)CH$_2$Cl, —OCH(CH$_3$)CH$_2$F, —OCH$_3$, —OCH$_2$CH$_3$, —OCH$_2$CH$_2$CH$_3$, and —OCH(CH$_3$)$_2$. In a still further aspect, each of R$^{1a}$, R$^{1b}$, and R$^{1c}$ is independently selected from hydrogen, —CH$_2$OH, —CH$_2$CH$_2$OH, —OCCl$_3$, —OCF$_3$, —OCHCl$_2$, —OCHF$_2$, —OCH$_2$Cl, —OCH$_2$F, —OCH$_2$CH$_2$Cl, —OCH$_2$CH$_2$F, —OCH$_3$, and —OCH$_2$CH$_3$. In yet a further aspect, each of R$^{1a}$, R$^{1b}$, and R$^{1c}$ is independently selected from hydrogen, —CH$_2$OH, —OCCl$_3$, —OCF$_3$, —OCHCl$_2$, —OCHF$_2$, —OCH$_2$Cl, —OCH$_2$F, and —OCH$_3$.

In various aspects, each of R$^{1a}$, R$^{1b}$, and R$^{1c}$ is independently selected from hydrogen, halogen, —CN, —NH$_2$, —OH, —NO$_2$, C1-C4 alkylamino, (C1-C4)(C1-C4) dialkylamino, and C1-C4 aminoalkyl. In a further aspect, each of R$^{1a}$, R$^{1b}$, and R$^{1c}$ is independently selected from hydrogen, —F, —Cl, —CN, —NH$_2$, —OH, —NO$_2$, —NHCH$_3$, —NHCH$_2$CH$_3$, —NHCH$_2$CH$_2$CH$_3$, —NHCH(CH$_3$)$_2$, —N(CH$_3$)$_2$, —N(CH$_3$)CH$_2$CH$_3$, —N(CH$_2$CH$_3$)CH$_2$CH$_2$CH$_3$, —N(CH$_3$)CH(CH$_3$)$_2$, —CH$_2$NH$_2$, —CH$_2$CH$_2$NH$_2$, —CH$_2$CH$_2$CH$_2$NH$_2$, and —CH(CH$_3$)CH$_2$NH$_2$. In a still further aspect, each of R$^{1a}$, R$^{1b}$, and R$^{1c}$ is independently selected from hydrogen, —F, —Cl, —CN, —NH$_2$, —OH, —NO$_2$, —NHCH$_3$, —NHCH$_2$CH$_3$, —N(CH$_3$)$_2$, —N(CH$_3$)CH$_2$CH$_3$, —CH$_2$NH$_2$, —CH$_2$CH$_2$NH$_2$. In yet a further aspect, each of R$^{1a}$, R$^{1b}$, and R$^{1c}$ is independently selected from hydrogen, —F, —Cl, —CN, —NH$_2$, —OH, —NO$_2$, —NHCH$_3$, —N(CH$_3$)$_2$, and —CH$_2$NH$_2$.

In various aspects, each of R$^{1a}$, R$^{1b}$, and R$^{1c}$ is independently selected from hydrogen, C1-C4 alkylamino, (C1-C4)(C1-C4) dialkylamino, and C1-C4 aminoalkyl. In a further aspect, each of R$^{1a}$, R$^{1b}$, and R$^{1c}$ is independently selected from hydrogen, —NHCH$_3$, —NHCH$_2$CH$_3$, —NHCH$_2$CH$_2$CH$_3$, —NHCH(CH$_3$)$_2$, —N(CH$_3$)$_2$, —N(CH$_3$)CH$_2$CH$_3$, —N(CH$_2$CH$_3$)CH$_2$CH$_2$CH$_3$, —N(CH$_3$)CH(CH$_3$)$_2$, —CH$_2$NH$_2$, —CH$_2$CH$_2$NH$_2$, —CH$_2$CH$_2$CH$_2$NH$_2$, and —CH(CH$_3$)CH$_2$NH$_2$. In a still further aspect, each of R$^{1a}$, R$^{1b}$, and R$^{1c}$ is independently selected from hydrogen, —NHCH$_3$, —NHCH$_2$CH$_3$, —N(CH$_3$)$_2$, —N(CH$_3$)CH$_2$CH$_3$, —CH$_2$NH$_2$, and —CH$_2$CH$_2$NH$_2$. In yet a further aspect, each of R$^{1a}$, R$^{1b}$, and R$^{1c}$ is independently selected from hydrogen, —NHCH$_3$, —N(CH$_3$)$_2$, and —CH$_2$NH$_2$.

In various aspects, each of R$^{1a}$, R$^{1b}$, and R$^{1c}$ is independently selected from hydrogen, halogen, C1-C4 alkyl, C1-C4 haloalkyl, C1-C4 haloalkoxy, and C1-C4 alkoxy. In a further aspect, each of R$^{1a}$, R$^{1b}$, and R$^{1c}$ is independently selected from hydrogen, —F, —Cl, methyl, ethyl, n-propyl, isopropyl, —CCl$_3$, —CF$_3$, —CHCl$_2$, —CHF$_2$, —CH$_2$Cl, —CH$_2$F, —CH$_2$CH$_2$Cl, —CH$_2$CH$_2$F, —CH$_2$CH$_2$CH$_2$Cl, —CH$_2$CH$_2$CH$_2$F, —CH(CH$_3$)CH$_2$Cl, —CH(CH$_3$)CH$_2$F, —OCCl$_3$, —OCF$_3$, —OCHCl$_2$, —OCHF$_2$, —OCH$_2$Cl, —OCH$_2$F, —OCH$_2$CH$_2$Cl, —OCH$_2$CH$_2$F, —OCH$_2$CH$_2$CH$_2$Cl, —OCH$_2$CH$_2$CH$_2$F, —OCH(CH$_3$)CH$_2$Cl, —OCH(CH$_3$)CH$_2$F, —OCH$_3$, —OCH$_2$CH$_3$, —OCH$_2$CH$_2$CH$_3$, and —OCH(CH$_3$)$_2$. In a still further aspect, each of R$^{1a}$, R$^{1b}$, and R$^{1c}$ is independently selected from hydrogen, —F, —Cl, methyl, ethyl, —CCl$_3$, —CF$_3$, —CHCl$_2$, —CHF$_2$, —CH$_2$Cl, —CH$_2$F, —CH$_2$CH$_2$Cl, —CH$_2$CH$_2$F, —OCCl$_3$, —OCF$_3$, —OCHCl$_2$, —OCHF$_2$, —OCH$_2$Cl, —OCH$_2$F, —OCH$_2$CH$_2$Cl, —OCH$_2$CH$_2$F, —OCH$_3$, and —OCH$_2$CH$_3$. In yet a further aspect, each of R$^{1a}$, R$^{1b}$, and R$^{1c}$ is independently selected from hydrogen, —F, —Cl, methyl, —CCl$_3$, —CF$_3$, —CHCl$_2$, —CHF$_2$, —CH$_2$Cl, —CH$_2$F, —OCCl$_3$, —OCF$_3$, —OCHCl$_2$, —OCHF$_2$, —OCH$_2$Cl, —OCH$_2$F, and —OCH$_3$.

In various aspects, each of R$^{1a}$, R$^{1b}$, and R$^{1c}$ is independently selected from hydrogen and halogen. In a further aspect, each of R$^{1a}$, R$^{1b}$, and R$^{1c}$ is independently selected from hydrogen, —F, —Cl, and —Br. In a still further aspect, each of R$^{1a}$, R$^{1b}$, and R$^{1c}$ is independently selected from hydrogen, —F, and —Cl. In yet a further aspect, each of R$^{1a}$, R$^{1b}$, and R$^{1c}$ is independently selected from hydrogen and —F. In an even further aspect, each of R$^{1a}$, R$^{1b}$, and R$^{1c}$ is independently selected from hydrogen and —Cl.

In various aspects, each of R$^{1a}$, R$^{1b}$, and R$^{1c}$ is hydrogen. In a further aspect, at least one of R$^{1a}$, R$^{1b}$, and R$^{1c}$ is hydrogen. In a still further aspect, two of R$^{1a}$, R$^{1b}$, and R$^{1c}$ is hydrogen.

In various aspects, one of R$^{1a}$, R$^{1b}$, and R$^{1c}$ is —OH or C1-C4 alkoxy. In a further aspect, one of R$^{1a}$, R$^{1b}$, and R$^{1c}$ is —OH, —OCH$_3$, —OCH$_2$CH$_3$, —OCH$_2$CH$_2$CH$_3$, or —OCH(CH$_3$)$_2$. In a still further aspect, one of R$^{1a}$, R$^{1b}$, and R$^{1c}$ is —OH, —OCH$_3$, or —OCH$_2$CH$_3$. In yet a further aspect, one of R$^{1a}$, R$^{1b}$, and R$^{1c}$ is —OH or —OCH$_3$.

In various aspects, one of R$^{1a}$, R$^{1b}$, and R$^{1c}$ is —OH or C1-C4 alkoxy, and two of R$^{1a}$, R$^{1b}$, and R$^{1c}$ are independently selected from hydrogen and halogen. In a further aspect, one of R$^{1a}$, R$^{1b}$, and R$^{1c}$ is —OH, —OCH$_3$, —OCH$_2$CH$_3$, —OCH$_2$CH$_2$CH$_3$, or —OCH(CH$_3$)$_2$, and two of R$^{1a}$, R$^{1b}$, and R$^{1c}$ are independently selected from hydrogen, —F, —Cl, and —Br. In a still further aspect, one of R$^{1a}$, R$^{1b}$, and R$^{1c}$ is —OH, —OCH$_3$, or —OCH$_2$CH$_3$, and two of R$^{1a}$, R$^{1b}$, and R$^{1c}$ are independently selected from hydrogen, —F, and —Cl. In yet a further aspect, one of R$^{1a}$, R$^{1b}$, and R$^{1c}$ is —OH or —OCH$_3$, and two of R$^{1a}$, R$^{1b}$, and R$^{1c}$ are independently selected from hydrogen and —F.

In various aspects, one of R$^{1a}$, R$^{1b}$, and R$^{1c}$ is —OH or —OCH$_3$, and two of R$^{1a}$, R$^{1b}$, and R$^{1c}$ are independently selected from hydrogen and halogen. In a further aspect, one of R$^{1a}$, R$^{1b}$, and R$^{1c}$ is —OH or —OCH$_3$, and two of R$^{1a}$, R$^{1b}$, and R$^{1c}$ are independently selected from hydrogen, —F, —Cl, and —Br. In a still further aspect, one of R$^{1a}$, R$^{1b}$, and R$^{1c}$ is —OH or —OCH$_3$, and two of R$^{1a}$, R$^{1b}$, and R$^{1c}$ are independently selected from hydrogen, —F, and —Cl. In yet a further aspect, one of R$^{1a}$, R$^{1b}$, and R$^{1c}$ is —OH or —OCH$_3$, and two of R$^{1a}$, R$^{1b}$, and R$^{1c}$ are independently selected from hydrogen and —F.

b. $R^{2a}$ and $R^{2b}$ Groups

In one aspect, each of $R^{2a}$ and $R^{2b}$ is independently selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In a further aspect, each of $R^{2a}$ and $R^{2b}$ is independently selected from hydrogen, —F, —Cl, —CN, —NH$_2$, —OH, —NO$_2$, methyl, ethyl, n-propyl, isopropyl, ethenyl, propenyl, —CCl$_3$, —CF$_3$, —CHCl$_2$, —CHF$_2$, —CH$_2$Cl, —CH$_2$F, —CH$_2$CH$_2$Cl, —CH$_2$CH$_2$F, —CH$_2$CH$_2$CH$_2$Cl, —CH$_2$CH$_2$CH$_2$F, —CH(CH$_3$)CH$_2$Cl, —CH(CH$_3$)CH$_2$F, —CH$_2$CN, —CH$_2$CH$_2$CN, —CH$_2$CH$_2$CH$_2$CN, —CH(CH$_3$)CH$_2$CN, —CH$_2$OH, —CH$_2$CH$_2$OH, —CH$_2$CH$_2$CH$_2$OH, —CH(CH$_3$)CH$_2$OH, —OCCl$_3$, —OCF$_3$, —OCHCl$_2$, —OCHF$_2$, —OCH$_2$Cl, —OCH$_2$F, —OCH$_2$CH$_2$Cl, —OCH$_2$CH$_2$F, —OCH$_2$CH$_2$CH$_2$Cl, —OCH$_2$CH$_2$CH$_2$F, —OCH(CH$_3$)CH$_2$Cl, —OCH(CH$_3$)CH$_2$F, —OCH$_3$, —OCH$_2$CH$_3$, —OCH$_2$CH$_2$CH$_3$, —OCH(CH$_3$)$_2$, —NHCH$_3$, —NHCH$_2$CH$_3$, —NHCH$_2$CH$_2$CH$_3$, —NHCH(CH$_3$)$_2$, —N(CH$_3$)$_2$, —N(CH$_3$)CH$_2$CH$_3$, —N(CH$_2$CH$_3$)CH$_2$CH$_2$CH$_3$, —N(CH$_3$)CH(CH$_3$)$_2$, —CH$_2$NH$_2$, —CH$_2$CH$_2$NH$_2$, —CH$_2$CH$_2$CH$_2$NH$_2$, and —CH(CH$_3$)CH$_2$NH$_2$. In a still further aspect, each of $R^{2a}$ and $R^{2b}$ is independently selected from hydrogen, —F, —Cl, —CN, —NH$_2$, —OH, —NO$_2$, methyl, ethyl, ethenyl, —CCl$_3$, —CF$_3$, —CHCl$_2$, —CHF$_2$, —CH$_2$Cl, —CH$_2$F, —CH$_2$CH$_2$Cl, —CH$_2$CH$_2$F, —CH$_2$CN, —CH$_2$CH$_2$CN, —CH$_2$OH, —CH$_2$CH$_2$OH, —OCCl$_3$, —OCF$_3$, —OCHCl$_2$, —OCHF$_2$, —OCH$_2$Cl, —OCH$_2$F, —OCH$_2$CH$_2$Cl, —OCH$_2$CH$_2$F, —OCH$_3$, —OCH$_2$CH$_3$, —NHCH$_3$, —NHCH$_2$CH$_3$, —N(CH$_3$)$_2$, —N(CH$_3$)CH$_2$CH$_3$, —CH$_2$NH$_2$, and —CH$_2$CH$_2$NH$_2$. In yet a further aspect, each of $R^{2a}$ and $R^{2b}$ is independently selected from hydrogen, —F, —Cl, —CN, —NH$_2$, —OH, —NO$_2$, methyl, —CCl$_3$, —CF$_3$, —CHCl$_2$, —CHF$_2$, —CH$_2$Cl, —CH$_2$F, —CH$_2$CN, —CH$_2$OH, —OCCl$_3$, —OCF$_3$, —OCHCl$_2$, —OCHF$_2$, —OCH$_2$Cl, —OCH$_2$F, —OCH$_3$, —NHCH$_3$, —N(CH$_3$)$_2$, and —CH$_2$NH$_2$.

In various aspects, each of $R^{2a}$ and $R^{2b}$ is independently selected from hydrogen, halogen, —CN, —NH$_2$, —OH, —NO$_2$, C1-C4 alkyl, and C2-C4 alkenyl. In a further aspect, each of $R^{2a}$ and $R^{2b}$ is independently selected from hydrogen, —F, —Cl, —CN, —NH$_2$, —OH, —NO$_2$, methyl, ethyl, n-propyl, isopropyl, ethenyl, and propenyl. In a still further aspect, each of $R^{2a}$ and $R^{2b}$ is independently selected from hydrogen, —F, —Cl, —CN, —NH$_2$, —OH, —NO$_2$, methyl, ethyl, and ethenyl. In yet a further aspect, each of $R^{2a}$ and $R^{2b}$ is independently selected from hydrogen, —F, —Cl, —CN, —NH$_2$, —OH, —NO$_2$, and methyl.

In various aspects, each of $R^{2a}$ and $R^{2b}$ is independently selected from hydrogen, C1-C4 alkyl, and C2-C4 alkenyl. In a further aspect, each of $R^{2a}$ and $R^{2b}$ is independently selected from hydrogen, methyl, ethyl, n-propyl, isopropyl, ethenyl, and propenyl. In a still further aspect, each of $R^{2a}$ and $R^{2b}$ is independently selected from hydrogen, methyl, ethyl, and ethenyl. In yet a further aspect, each of $R^{2a}$ and $R^{2b}$ is independently selected from hydrogen and methyl.

In various aspects, each of $R^{2a}$ and $R^{2b}$ is independently selected from hydrogen, halogen, —CN, —NH$_2$, —OH, —NO$_2$, C1-C4 haloalkyl, and C1-C4 cyanoalkyl. In a further aspect, each of $R^{2a}$ and $R^{2b}$ is independently selected from hydrogen, —F, —Cl, —CN, —NH$_2$, —OH, —NO$_2$, —CCl$_3$, —CF$_3$, —CHCl$_2$, —CHF$_2$, —CH$_2$Cl, —CH$_2$F, —CH$_2$CH$_2$Cl, —CH$_2$CH$_2$F, —CH$_2$CH$_2$CH$_2$Cl, —CH$_2$CH$_2$CH$_2$F, —CH(CH$_3$)CH$_2$Cl, —CH(CH$_3$)CH$_2$F, —CH$_2$CN, —CH$_2$CH$_2$CN, —CH$_2$CH$_2$CH$_2$CN, and —CH(CH$_3$)CH$_2$CN. In a still further aspect, each of $R^{2a}$ and $R^{2b}$ is independently selected from hydrogen, —F, —Cl, —CN, —NH$_2$, —OH, —NO$_2$, —CCl$_3$, —CF$_3$, —CHCl$_2$, —CHF$_2$, —CH$_2$Cl, —CH$_2$F, —CH$_2$CH$_2$Cl, —CH$_2$CH$_2$F, —CH$_2$CN, and —CH$_2$CH$_2$CN. In yet a further aspect, each of $R^{2a}$ and $R^{2b}$ is independently selected from hydrogen, —F, —Cl, —CN, —NH$_2$, —OH, —NO$_2$, —CCl$_3$, —CF$_3$, —CHCl$_2$, —CHF$_2$, —CH$_2$Cl, —CH$_2$F, and —CH$_2$CN.

In various aspects, each of $R^{2a}$ and $R^{2b}$ is independently selected from hydrogen, C1-C4 haloalkyl, and C1-C4 cyanoalkyl. In a further aspect, each of $R^{2a}$ and $R^{2b}$ is independently selected from hydrogen, —CCl$_3$, —CF$_3$, —CHCl$_2$, —CHF$_2$, —CH$_2$Cl, —CH$_2$F, —CH$_2$CH$_2$Cl, —CH$_2$CH$_2$F, —CH$_2$CH$_2$CH$_2$Cl, —CH$_2$CH$_2$CH$_2$F, —CH(CH$_3$)CH$_2$Cl, —CH(CH$_3$)CH$_2$F, —CH$_2$CN, —CH$_2$CH$_2$CN, —CH$_2$CH$_2$CH$_2$CN, and —CH(CH$_3$)CH$_2$CN. In a still further aspect, each of $R^{2a}$ and $R^{2b}$ is independently selected from hydrogen, —CCl$_3$, —CF$_3$, —CHCl$_2$, —CHF$_2$, —CH$_2$Cl, —CH$_2$F, —CH$_2$CH$_2$Cl, —CH$_2$CH$_2$F, —CH$_2$CN, and —CH$_2$CH$_2$CN. In yet a further aspect, each of $R^{2a}$ and $R^{2b}$ is independently selected from hydrogen, —CCl$_3$, —CF$_3$, —CHCl$_2$, —CHF$_2$, —CH$_2$Cl, —CH$_2$F, and —CH$_2$CN.

In various aspects, each of $R^{2a}$ and $R^{2b}$ is independently selected from hydrogen, halogen, —CN, —NH$_2$, —OH, —NO$_2$, C1-C4 hydroxyalkyl, C1-C4 haloalkoxy, and C1-C4 alkoxy. In a further aspect, each of $R^{2a}$ and $R^{2b}$ is independently selected from hydrogen, —F, —Cl, —CN, —NH$_2$, —OH, —NO$_2$, —CH$_2$OH, —CH$_2$CH$_2$OH, —CH$_2$CH$_2$CH$_2$OH, —CH(CH$_3$)CH$_2$OH, —OCCl$_3$, —OCF$_3$, —OCHCl$_2$, —OCHF$_2$, —OCH$_2$Cl, —OCH$_2$F, —OCH$_2$CH$_2$Cl, —OCH$_2$CH$_2$F, —OCH$_2$CH$_2$CH$_2$Cl, —OCH$_2$CH$_2$CH$_2$F, —OCH(CH$_3$)CH$_2$Cl, —OCH(CH$_3$)CH$_2$F, —OCH$_3$, —OCH$_2$CH$_3$, —OCH$_2$CH$_2$CH$_3$, and —OCH(CH$_3$)$_2$. In a still further aspect, each of $R^{2a}$ and $R^{2b}$ is independently selected from hydrogen, —F, —Cl, —CN, —NH$_2$, —OH, —NO$_2$, —CH$_2$OH, —CH$_2$CH$_2$OH, —OCCl$_3$, —OCF$_3$, —OCHCl$_2$, —OCHF$_2$, —OCH$_2$Cl, —OCH$_2$F, —OCH$_2$CH$_2$Cl, —OCH$_2$CH$_2$F, —OCH$_3$, and —OCH$_2$CH$_3$. In yet a further aspect, each of $R^{2a}$ and $R^{2b}$ is independently selected from hydrogen, —F, —Cl, —CN, —NH$_2$, —OH, —NO$_2$, —CH$_2$OH, —OCCl$_3$, —OCF$_3$, —OCHCl$_2$, —OCHF$_2$, —OCH$_2$Cl, —OCH$_2$F, and —OCH$_3$.

In various aspects, each of $R^{2a}$ and $R^{2b}$ is independently selected from hydrogen, C1-C4 hydroxyalkyl, C1-C4 haloalkoxy, and C1-C4 alkoxy. In a further aspect, each of $R^{2a}$ and $R^{2b}$ is independently selected from hydrogen, —CH$_2$OH, —CH$_2$CH$_2$OH, —CH$_2$CH$_2$CH$_2$OH, —CH(CH$_3$)CH$_2$OH, —OCCl$_3$, —OCF$_3$, —OCHCl$_2$, —OCHF$_2$, —OCH$_2$Cl, —OCH$_2$F, —OCH$_2$CH$_2$Cl, —OCH$_2$CH$_2$F, —OCH$_2$CH$_2$CH$_2$Cl, —OCH$_2$CH$_2$CH$_2$F, —OCH(CH$_3$)CH$_2$Cl, —OCH(CH$_3$)CH$_2$F, —OCH$_3$, —OCH$_2$CH$_3$, —OCH$_2$CH$_2$CH$_3$, and —OCH(CH$_3$)$_2$. In a still further aspect, each of $R^{2a}$ and $R^{2b}$ is independently selected from hydrogen, —CH$_2$OH, —CH$_2$CH$_2$OH, —OCCl$_3$, —OCF$_3$, —OCHCl$_2$, —OCHF$_2$, —OCH$_2$Cl, —OCH$_2$F, —OCH$_2$CH$_2$Cl, —OCH$_2$CH$_2$F, —OCH$_3$, and —OCH$_2$CH$_3$. In yet a further aspect, each of $R^{2a}$ and $R^{2b}$ is independently selected from hydrogen, —CH$_2$OH, —OCCl$_3$, —OCF$_3$, —OCHCl$_2$, —OCHF$_2$, —OCH$_2$Cl, —OCH$_2$F, and —OCH$_3$.

In various aspects, each of $R^{2a}$ and $R^{2b}$ is independently selected from hydrogen, halogen, —CN, —NH$_2$, —OH, —NO$_2$, C1-C4 alkylamino, (C1-C4)(C1-C4) dialkylamino, and C1-C4 aminoalkyl. In a further aspect, each of $R^{2a}$ and $R^{2b}$ is independently selected from hydrogen, —F, —Cl, —CN, —NH$_2$, —OH, —NO$_2$, —NHCH$_3$, —NHCH$_2$CH$_3$, —NHCH$_2$CH$_2$CH$_3$, —NHCH(CH$_3$)$_2$, —N(CH$_3$)$_2$, —N(CH$_3$)CH$_2$CH$_3$, —N(CH$_2$CH$_3$)CH$_2$CH$_3$, —N(CH$_3$)CH(CH$_3$)$_2$, —CH$_2$NH$_2$, —CH$_2$CH$_2$NH$_2$, —CH$_2$CH$_2$CH$_2$NH$_2$, and —CH(CH$_3$)CH$_2$NH$_2$. In a still further aspect, each of $R^{2a}$ and $R^{2b}$ is independently selected from hydrogen, —F, —Cl, —CN, —NH$_2$, —OH, —NO$_2$, —NHCH$_3$, —NHCH$_2$CH$_3$, —N(CH$_3$)$_2$, —N(CH$_3$)CH$_2$CH$_3$, —CH$_2$NH$_2$, —CH$_2$CH$_2$NH$_2$. In yet a further aspect, each of $R^{2a}$ and $R^{2b}$ is independently selected from hydrogen, —F, —Cl, —CN, —NH$_2$, —OH, —NO$_2$, —NHCH$_3$, —N(CH$_3$)$_2$, and —CH$_2$NH$_2$.

In various aspects, each of $R^{2a}$ and $R^{2b}$ is independently selected from hydrogen, C1-C4 alkylamino, (C1-C4)(C1-C4) dialkylamino, and C1-C4 aminoalkyl. In a further aspect, each of $R^{2a}$ and $R^{2b}$ is independently selected from hydrogen, —NHCH$_3$, —NHCH$_2$CH$_3$, —NHCH$_2$CH$_2$CH$_3$, —NHCH(CH$_3$)$_2$, —N(CH$_3$)$_2$, —N(CH$_3$)CH$_2$CH$_3$, —N(CH$_2$CH$_3$)CH$_2$CH$_3$, —N(CH$_3$)CH(CH$_3$)$_2$, —CH$_2$NH$_2$, —CH$_2$CH$_2$NH$_2$, —CH$_2$CH$_2$CH$_2$NH$_2$, and —CH(CH$_3$)CH$_2$NH$_2$. In a still further aspect, each of $R^{2a}$ and $R^{2b}$ is independently selected from hydrogen, —NHCH$_3$, —NHCH$_2$CH$_3$, —N(CH$_3$)$_2$, —N(CH$_3$)CH$_2$CH$_3$, —CH$_2$NH$_2$, and —CH$_2$CH$_2$NH$_2$. In yet a further aspect, each of $R^{2a}$ and $R^{2b}$ is independently selected from hydrogen, —NHCH$_3$, —N(CH$_3$)$_2$, and —CH$_2$NH$_2$.

In various aspects, each of $R^{2a}$ and $R^{2b}$ is independently selected from hydrogen, halogen, C1-C4 alkyl, C1-C4 haloalkyl, C1-C4 haloalkoxy, and C1-C4 alkoxy. In a further aspect, each of $R^{2a}$ and $R^{2b}$ is independently selected from hydrogen, —F, —Cl, methyl, ethyl, n-propyl, isopropyl, —CCl$_3$, —CF$_3$, —CHCl$_2$, —CHF$_2$, —CH$_2$Cl, —CH$_2$F, —CH$_2$CH$_2$Cl, —CH$_2$CH$_2$F, —CH$_2$CH$_2$CH$_2$Cl, —CH$_2$CH$_2$CH$_2$F, —CH(CH$_3$)CH$_2$Cl, —CH(CH$_3$)CH$_2$F, —OCCl$_3$, —OCF$_3$, —OCHCl$_2$, —OCHF$_2$, —OCH$_2$Cl, —OCH$_2$F, —OCH$_2$CH$_2$Cl, —OCH$_2$CH$_2$F, —OCH$_2$CH$_2$CH$_2$Cl, —OCH$_2$CH$_2$CH$_2$F, —OCH(CH$_3$)CH$_2$Cl, —OCH(CH$_3$)CH$_2$F, —OCH$_3$, —OCH$_2$CH$_3$, —OCH$_2$CH$_2$CH$_3$, and —OCH(CH$_3$)$_2$. In a still further aspect, each of $R^{2a}$ and $R^{2b}$ is independently selected from hydrogen, —F, —Cl, methyl, ethyl, —CCl$_3$, —CF$_3$, —CHCl$_2$, —CHF$_2$, —CH$_2$Cl, —CH$_2$F, —CH$_2$CH$_2$Cl, —CH$_2$CH$_2$F, —OCCl$_3$, —OCF$_3$, —OCHCl$_2$, —OCHF$_2$, —OCH$_2$Cl, —OCH$_2$F, —OCH$_2$CH$_2$Cl, —OCH$_2$CH$_2$F, —OCH$_3$, and —OCH$_2$CH$_3$. In yet a further aspect, each of $R^{2a}$ and $R^{2b}$ is independently selected from hydrogen, —F, —Cl, methyl, —CCl$_3$, —CF$_3$, —CHCl$_2$, —CHF$_2$, —CH$_2$Cl, —CH$_2$F, —OCCl$_3$, —OCF$_3$, —OCHCl$_2$, —OCHF$_2$, —OCH$_2$Cl, —OCH$_2$F, and —OCH$_3$.

In various aspects, each of $R^{2a}$ and $R^{2b}$ is independently selected from hydrogen and halogen. In a further aspect, each of $R^{2a}$ and $R^{2b}$ is independently selected from hydrogen, —F, —Cl, and —Br. In a still further aspect, each of $R^{2a}$ and $R^{2b}$ is independently selected from hydrogen, —F, and —Cl. In yet a further aspect, each of $R^{2a}$ and $R^{2b}$ is independently selected from hydrogen and —F. In an even further aspect, each of $R^{2a}$ and $R^{2b}$ is independently selected from hydrogen and —Cl.

In various aspects, each of $R^{2a}$ and $R^{2b}$ is hydrogen.

c. $R^{3a}$, $R^{3b}$, $R^{3c}$, $R^{3d}$, $R^{3e}$, and $R^{3f}$ Groups

In one aspect, each of $R^{3a}$, $R^{3b}$, $R^{3c}$, $R^{3d}$, $R^{3e}$, and $R^{3f}$ is independently selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In a further aspect, each of $R^{3a}$, $R^{3b}$, $R^{3c}$, $R^{3d}$, $R^{3e}$, and $R^{3f}$ is independently selected from hydrogen, —F, —Cl, —CN, —NH$_2$, —OH, —NO$_2$, methyl, ethyl, n-propyl, isopropyl, ethenyl, propenyl, —CCl$_3$, —CF$_3$, —CHCl$_2$, —CHF$_2$, —CH$_2$Cl, —CH$_2$F, —CH$_2$CH$_2$Cl, —CH$_2$CH$_2$F, —CH$_2$CH$_2$CH$_2$Cl, —CH$_2$CH$_2$CH$_2$F, —CH(CH$_3$)CH$_2$Cl, —CH(CH$_3$)CH$_2$F, —CH$_2$CN, —CH$_2$CH$_2$CN, —CH$_2$CH$_2$CH$_2$CN, —CH(CH$_3$)CH$_2$CN, —CH$_2$OH, —CH$_2$CH$_2$OH, —CH$_2$CH$_2$CH$_2$OH, —CH(CH$_3$)CH$_2$OH, —OCCl$_3$, —OCF$_3$, —OCHCl$_2$, —OCHF$_2$, —OCH$_2$Cl, —OCH$_2$F, —OCH$_2$CH$_2$Cl, —OCH$_2$CH$_2$F, —OCH$_2$CH$_2$CH$_2$Cl, —OCH$_2$CH$_2$CH$_2$F, —OCH(CH$_3$)CH$_2$Cl, —OCH(CH$_3$)CH$_2$F, —OCH$_3$, —OCH$_2$CH$_3$, —OCH$_2$CH$_2$CH$_3$, —OCH(CH$_3$)$_2$, —NHCH$_3$, —NHCH$_2$CH$_3$, —NHCH$_2$CH$_2$CH$_3$, —NHCH(CH$_3$)$_2$, —N(CH$_3$)$_2$, —N(CH$_3$)CH$_2$CH$_3$, —N(CH$_2$CH$_3$)CH$_2$CH$_3$, —N(CH$_3$)CH(CH$_3$)$_2$, —CH$_2$NH$_2$, —CH$_2$CH$_2$NH$_2$, —CH$_2$CH$_2$CH$_2$NH$_2$, and —CH(CH$_3$)CH$_2$NH$_2$.

In a still further aspect, each of $R^{3a}$, $R^{3b}$, $R^{3c}$, $R^{3d}$, $R^{3e}$, and $R^{3f}$ is independently selected from hydrogen, —F, —Cl, —CN, —NH$_2$, —OH, —NO$_2$, methyl, ethyl, ethenyl, —CCl$_3$, —CF$_3$, —CHCl$_2$, —CHF$_2$, —CH$_2$Cl, —CH$_2$F, —CH$_2$CH$_2$Cl, —CH$_2$CH$_2$F, —CH$_2$CN, —CH$_2$CH$_2$CN, —CH$_2$OH, —CH$_2$CH$_2$OH, —OCCl$_3$, —OCF$_3$, —OCHCl$_2$, —OCHF$_2$, —OCH$_2$Cl, —OCH$_2$F, —OCH$_2$CH$_2$Cl, —OCH$_2$CH$_2$F, —OCH$_3$, —OCH$_2$CH$_3$, —NHCH$_3$, —NHCH$_2$CH$_3$, —N(CH$_3$)$_2$, —N(CH$_3$)CH$_2$CH$_3$, —CH$_2$NH$_2$, and —CH$_2$CH$_2$NH$_2$. In yet a further aspect, each of $R^{3a}$, $R^{3b}$, $R^{3c}$, $R^{3d}$, $R^{3e}$, and $R^{3f}$ is independently selected from hydrogen, —F, —Cl, —CN, —NH$_2$, —OH, —NO$_2$, methyl, —CCl$_3$, —CF$_3$, —CHCl$_2$, —CHF$_2$, —CH$_2$Cl, —CH$_2$F, —CH$_2$CN, —CH$_2$OH, —OCCl$_3$, —OCF$_3$, —OCHCl$_2$, —OCHF$_2$, —OCH$_2$Cl, —OCH$_2$F, —OCH$_3$, —NHCH$_3$, —N(CH$_3$)$_2$, and —CH$_2$NH$_2$.

In various aspects, each of $R^{3a}$, $R^{3b}$, $R^{3c}$, $R^{3d}$, $R^{3e}$, and $R^{3f}$ is independently selected from hydrogen, halogen, —CN, —NH$_2$, —OH, —NO$_2$, C1-C4 alkyl, and C2-C4 alkenyl.

In a further aspect, each of $R^{3a}$, $R^{3b}$, $R^{3c}$, $R^{3d}$, $R^{3e}$, and $R^{3f}$ is independently selected from hydrogen, —F, —Cl, —CN, —NH$_2$, —OH, —NO$_2$, methyl, ethyl, n-propyl, isopropyl, ethenyl, and propenyl. In a still further aspect, each of $R^{3a}$, $R^{3b}$, $R^{3c}$, $R^{3d}$, $R^{3e}$, and $R^{3f}$ is independently selected from hydrogen, —F, —Cl, —CN, —NH$_2$, —OH, —NO$_2$, methyl, ethyl, and ethenyl. In yet a further aspect, each of $R^{3a}$, $R^{3b}$, $R^{3c}$, $R^{3d}$, $R^{3e}$, and $R^{3f}$ is independently selected from hydrogen, —F, —Cl, —CN, —NH$_2$, —OH, —NO$_2$, and methyl.

In various aspects, each of $R^{3a}$, $R^{3b}$, $R^{3c}$, $R^{3d}$, $R^{3e}$, and $R^{3f}$ is independently selected from hydrogen, C1-C4 alkyl, and C2-C4 alkenyl. In a further aspect, each of $R^{3a}$, $R^{3b}$, $R^{3c}$, $R^{3d}$, $R^{3e}$, and $R^{3f}$ is independently selected from hydrogen, methyl, ethyl, n-propyl, isopropyl, ethenyl, and propenyl. In a still further aspect, each of $R^{3a}$, $R^{3b}$, $R^{3c}$, $R^{3d}$, $R^{3e}$, and $R^{3f}$ is independently selected from hydrogen, methyl, ethyl, and ethenyl. In yet a further aspect, each of $R^{3a}$, $R^{3b}$, $R^{3c}$, $R^{3d}$, $R^{3e}$, and $R^{3f}$ is independently selected from hydrogen and methyl.

In various aspects, each of $R^{3a}$, $R^{3b}$, $R^{3c}$, $R^{3d}$, $R^{3e}$, and $R^{3f}$ is independently selected from hydrogen, halogen, —CN, —NH$_2$, —OH, —NO$_2$, C1-C4 haloalkyl, and C1-C4 cyanoalkyl. In a further aspect, each of $R^{3a}$, $R^{3b}$, $R^{3c}$, $R^{3d}$, $R^{3e}$, and $R^{3f}$ is independently selected from hydrogen, —F, —Cl, —CN, —NH$_2$, —OH, —NO$_2$, —CCl$_3$, —CF$_3$, —CHCl$_2$, —CHF$_2$, —CH$_2$Cl, —CH$_2$F, —CH$_2$CH$_2$Cl, —CH$_2$CH$_2$F, —CH$_2$CH$_2$CH$_2$Cl, —CH$_2$CH$_2$CH$_2$F, —CH(CH$_3$)CH$_2$Cl, —CH(CH$_3$)CH$_2$F, —CH$_2$CN, —CH$_2$CH$_2$CN, —CH$_2$CH$_2$CH$_2$CN, and —CH(CH$_3$)CH$_2$CN. In a still further aspect, each of $R^{3a}$, $R^{3b}$, $R^{3c}$, $R^{3d}$, $R^{3e}$, and $R^{3f}$ is independently selected from hydrogen, —F, —Cl, —CN, —NH$_2$, —OH, —NO$_2$, —CCl$_3$, —CF$_3$, —CHCl$_2$, —CHF$_2$, —CH$_2$Cl, —CH$_2$F, —CH$_2$CH$_2$Cl, —CH$_2$CH$_2$F, —CH$_2$CN, and —CH$_2$CH$_2$CN. In yet a further aspect, each of R$^{3a}$, R$^{3b}$, R$^{3c}$, R$^{3d}$, R$^{3e}$, and R$^{3f}$ is independently selected from hydrogen, —F, —Cl, —CN, —NH$_2$, —OH, —NO$_2$, —CCl$_3$, —CF$_3$, —CHCl$_2$, —CHF$_2$, —CH$_2$Cl, —CH$_2$F, and —CH$_2$CN.

In various aspects, each of R$^{3a}$, R$^{3b}$, R$^{3c}$, R$^{3d}$, R$^{3e}$, and R$^{3f}$ is independently selected from hydrogen, C1-C4 haloalkyl, and C1-C4 cyanoalkyl. In a further aspect, each of R$^{3a}$, R$^{3b}$, R$^{3c}$, R$^{3d}$, R$^{3e}$, and R$^{3f}$ is independently selected from hydrogen, —CCl$_3$, —CF$_3$, —CHCl$_2$, —CHF$_2$, —CH$_2$Cl, —CH$_2$F, —CH$_2$CH$_2$Cl, —CH$_2$CH$_2$F, —CH$_2$CH$_2$CH$_2$Cl, —CH$_2$CH$_2$CH$_2$F, —CH(CH$_3$)CH$_2$Cl, —CH(CH$_3$)CH$_2$F, —CH$_2$CN, —CH$_2$CH$_2$CN, —CH$_2$CH$_2$CH$_2$CN, and —CH(CH$_3$)CH$_2$CN. In a still further aspect, each of R$^{3a}$, R$^{3b}$, R$^{3c}$, R$^{3d}$, R$^{3e}$, and R$^{3f}$ is independently selected from hydrogen, —CCl$_3$, —CF$_3$, —CHCl$_2$, —CHF$_2$, —CH$_2$Cl, —CH$_2$F, —CH$_2$CH$_2$Cl, —CH$_2$CH$_2$F, —CH$_2$CN, and —CH$_2$CH$_2$CN. In yet a further aspect, each of R$^{3a}$, R$^{3b}$, R$^{3c}$, R$^{3d}$, R$^{3e}$, and R$^{3f}$ is independently selected from hydrogen, —CCl$_3$, —CF$_3$, —CHCl$_2$, —CHF$_2$, —CH$_2$Cl, —CH$_2$F, and —CH$_2$CN.

In various aspects, each of R$^{3a}$, R$^{3b}$, R$^{3c}$, R$^{3d}$, R$^{3e}$, and R$^{3f}$ is independently selected from hydrogen, halogen, —CN, —NH$_2$, —OH, —NO$_2$, C1-C4 hydroxyalkyl, C1-C4 haloalkoxy, and C1-C4 alkoxy. In a further aspect, each of R$^{3a}$, R$^{3b}$, R$^{3c}$, R$^{3d}$, R$^{3e}$, and R$^{3f}$ is independently selected from hydrogen, —F, —Cl, —CN, —NH$_2$, —OH, —NO$_2$, —CH$_2$OH, —CH$_2$CH$_2$OH, —CH$_2$CH$_2$CH$_2$OH, —CH(CH$_3$)CH$_2$OH, —OCCl$_3$, —OCF$_3$, —OCHCl$_2$, —OCHF$_2$, —OCH$_2$Cl, —OCH$_2$F, —OCH$_2$CH$_2$Cl, —OCH$_2$CH$_2$F, —OCH$_2$CH$_2$CH$_2$Cl, —OCH$_2$CH$_2$CH$_2$F, —OCH(CH$_3$)CH$_2$Cl, —OCH(CH$_3$)CH$_2$F, —OCH$_3$, —OCH$_2$CH$_3$, —OCH$_2$CH$_2$CH$_3$, and —OCH(CH$_3$)$_2$. In a still further aspect, each of R$^{3a}$, R$^{3b}$, R$^{3c}$, R$^{3d}$, R$^{3e}$, and R$^{3f}$ is independently selected from hydrogen, —F, —Cl, —CN, —NH$_2$, —OH, —NO$_2$, —CH$_2$OH, —CH$_2$CH$_2$OH, —OCCl$_3$, —OCF$_3$, —OCHCl$_2$, —OCHF$_2$, —OCH$_2$Cl, —OCH$_2$F, —OCH$_2$CH$_2$Cl, —OCH$_2$CH$_2$F, —OCH$_3$, and —OCH$_2$CH$_3$. In yet a further aspect, each of R$^{3a}$, R$^{3b}$, R$^{3c}$, R$^{3d}$, R$^{3e}$, and R$^{3f}$ is independently selected from hydrogen, —F, —Cl, —CN, —NH$_2$, —OH, —NO$_2$, —CH$_2$OH, —OCCl$_3$, —OCF$_3$, —OCHCl$_2$, —OCHF$_2$, —OCH$_2$Cl, —OCH$_2$F, and —OCH$_3$.

In various aspects, each of R$^{3a}$, R$^{3b}$, R$^{3c}$, R$^{3d}$, R$^{3e}$, and R$^{3f}$ is independently selected from hydrogen, C1-C4 hydroxyalkyl, C1-C4 haloalkoxy, and C1-C4 alkoxy. In a further aspect, each of R$^{3a}$, R$^{3b}$, R$^{3c}$, R$^{3d}$, R$^{3e}$, and R$^{3f}$ is independently selected from hydrogen, —CH$_2$OH, —CH$_2$CH$_2$OH, —CH$_2$CH$_2$CH$_2$OH, —CH(CH$_3$)CH$_2$OH, —OCCl$_3$, —OCF$_3$, —OCHCl$_2$, —OCHF$_2$, —OCH$_2$Cl, —OCH$_2$F, —OCH$_2$CH$_2$Cl, —OCH$_2$CH$_2$F, —OCH$_2$CH$_2$CH$_2$Cl, —OCH$_2$CH$_2$CH$_2$F, —OCH(CH$_3$)CH$_2$Cl, —OCH(CH$_3$)CH$_2$F, —OCH$_3$, —OCH$_2$CH$_3$, —OCH$_2$CH$_2$CH$_3$, and —OCH(CH$_3$)$_2$. In a still further aspect, each of R$^{3a}$, R$^{3b}$, R$^{3c}$, R$^{3d}$, R$^{3e}$, and R$^{3f}$ is independently selected from hydrogen, —CH$_2$OH, —CH$_2$CH$_2$OH, —OCCl$_3$, —OCF$_3$, —OCHCl$_2$, —OCHF$_2$, —OCH$_2$Cl, —OCH$_2$F, —OCH$_2$CH$_2$Cl, —OCH$_2$CH$_2$F, —OCH$_3$, and —OCH$_2$CH$_3$. In yet a further aspect, each of R$^{3a}$, R$^{3b}$, R$^{3c}$, R$^{3d}$, R$^{3e}$, and R$^{3f}$ is independently selected from hydrogen, —CH$_2$OH, —OCCl$_3$, —OCF$_3$, —OCHCl$_2$, —OCHF$_2$, —OCH$_2$Cl, —OCH$_2$F, and —OCH$_3$.

In various aspects, each of R$^{3a}$, R$^{3b}$, R$^{3c}$, R$^{3d}$, R$^{3e}$, and R$^{3f}$ is independently selected from hydrogen, halogen, —CN, —NH$_2$, —OH, —NO$_2$, C1-C4 alkylamino, (C1-C4)(C1-C4) dialkylamino, and C1-C4 aminoalkyl. In a further aspect, each of R$^{3a}$, R$^{3b}$, R$^{3c}$, R$^{3d}$, R$^{3e}$, and R$^{3f}$ is independently selected from hydrogen, —F, —Cl, —CN, —NH$_2$, —OH, —NO$_2$, —NHCH$_3$, —NHCH$_2$CH$_3$, —NHCH$_2$CH$_2$CH$_3$, —NHCH(CH$_3$)$_2$, —N(CH$_3$)$_2$, —N(CH$_3$)CH$_2$CH$_3$, —N(CH$_2$CH$_3$)CH$_2$CH$_2$CH$_3$, —N(CH$_3$)CH(CH$_3$)$_2$, —CH$_2$NH$_2$, —CH$_2$CH$_2$NH$_2$, —CH$_2$CH$_2$CH$_2$NH$_2$, and —CH(CH$_3$)CH$_2$NH$_2$. In a still further aspect, each of R$^{3a}$, R$^{3b}$, R$^{3c}$, R$^{3d}$, R$^{3e}$, and R$^{3f}$ is independently selected from hydrogen, —F, —Cl, —CN, —NH$_2$, —OH, —NO$_2$, —NHCH$_3$, —NHCH$_2$CH$_3$, —N(CH$_3$)$_2$, —N(CH$_3$)CH$_2$CH$_3$, —CH$_2$NH$_2$, and —CH$_2$CH$_2$NH$_2$. In yet a further aspect, each of R$^{3a}$, R$^{3b}$, R$^{3c}$, R$^{3d}$, R$^{3e}$, and R$^{3f}$ is independently selected from hydrogen, —F, —Cl, —CN, —NH$_2$, —OH, —NO$_2$, —NHCH$_3$, —N(CH$_3$)$_2$, and —CH$_2$NH$_2$.

In various aspects, each of R$^{3a}$, R$^{3b}$, R$^{3c}$, R$^{3d}$, R$^{3e}$, and R$^{3f}$ is independently selected from hydrogen, C1-C4 alkylamino, (C1-C4)(C1-C4) dialkylamino, and C1-C4 aminoalkyl. In a further aspect, each of R$^{3a}$, R$^{3b}$, R$^{3c}$, R$^{3d}$, R$^{3e}$, and R$^{3f}$ is independently selected from hydrogen, —NHCH$_3$, —NHCH$_2$CH$_3$, —NHCH$_2$CH$_2$CH$_3$, —NHCH(CH$_3$)$_2$, —N(CH$_3$)$_2$, —N(CH$_3$)CH$_2$CH$_3$, —N(CH$_2$CH$_3$)CH$_2$CH$_2$CH$_3$, —N(CH$_3$)CH(CH$_3$)$_2$, —CH$_2$NH$_2$, —CH$_2$CH$_2$NH$_2$, —CH$_2$CH$_2$CH$_2$NH$_2$, and —CH(CH$_3$)CH$_2$NH$_2$. In a still further aspect, each of R$^{3a}$, R$^{3b}$, R$^{3c}$, R$^{3d}$, R$^{3e}$, and R$^{3f}$ is independently selected from hydrogen, —NHCH$_3$, —NHCH$_2$CH$_3$, —N(CH$_3$)$_2$, —N(CH$_3$)CH$_2$CH$_3$, —CH$_2$NH$_2$, and —CH$_2$CH$_2$NH$_2$. In yet a further aspect, each of R$^{3a}$, R$^{3b}$, R$^{3c}$, R$^{3d}$, R$^{3e}$, and R$^{3f}$ is independently selected from hydrogen, —NHCH$_3$, —N(CH$_3$)$_2$, and —CH$_2$NH$_2$.

In various aspects, each of R$^{3a}$, R$^{3b}$, R$^{3c}$, R$^{3d}$, R$^{3e}$, and R$^{3f}$ is independently selected from hydrogen and halogen. In a further aspect, each of R$^{3a}$, R$^{3b}$, R$^{3c}$, R$^{3d}$, R$^{3e}$, and R$^{3f}$ is independently selected from hydrogen, —F, —Cl, and —Br. In a still further aspect, each of R$^{3a}$, R$^{3b}$, R$^{3c}$, R$^{3d}$, R$^{3e}$, and R$^{3f}$ is independently selected from hydrogen, —F, and —Cl. In yet a further aspect, each of R$^{3a}$, R$^{3b}$, R$^{3c}$, R$^{3d}$, R$^{3e}$, and R$^{3f}$ is independently selected from hydrogen and —Cl. In an even further aspect, each of R$^{3a}$, R$^{3b}$, R$^{3c}$, R$^{3d}$, R$^{3e}$, and R$^{3f}$ is independently selected from hydrogen and —F.

In various aspects, each of R$^{3a}$, R$^{3b}$, R$^{3e}$, R$^{3d}$, R$^{3e}$, and R$^{3f}$ is hydrogen.

2. Example Thioquinolinones

In one aspect, a compound can be present as:

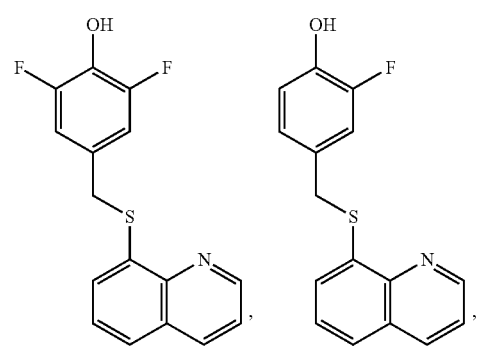

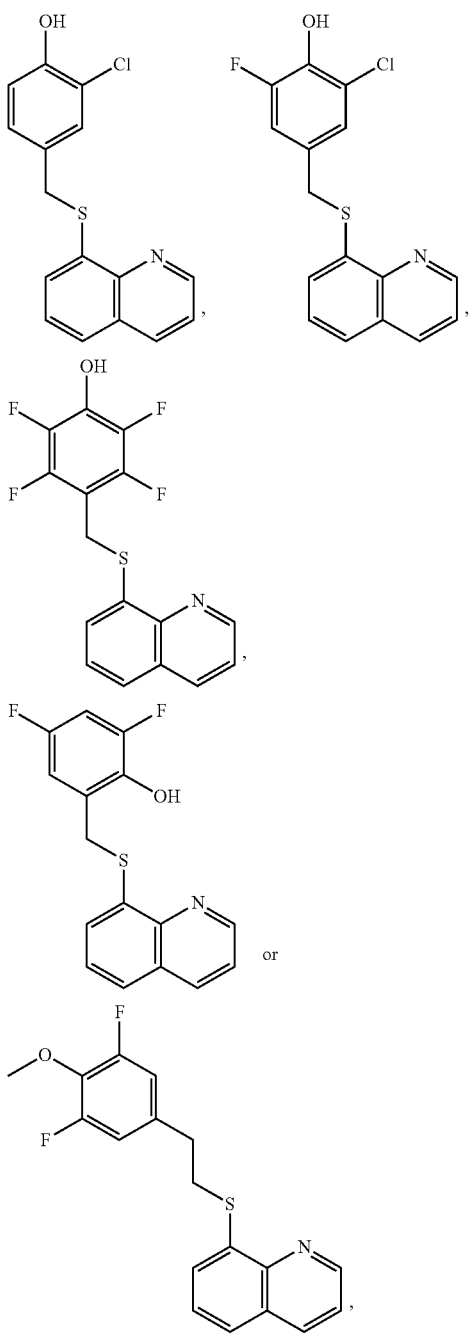

or a pharmaceutically acceptable salt thereof.

In one aspect, a compound can be present as:

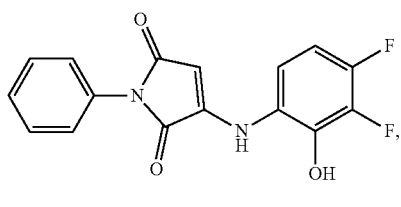 [SMILES: O=C1C=C(Nc2ccc(F)c(F)c2O)C(=O)N1c1ccccc1]

or a pharmaceutically acceptable salt thereof.

3. Prophetic Thioquinolinone Examples

The following compound examples are prophetic, and can be prepared using the synthesis methods described herein above and other general methods as needed as would be known to one skilled in the art. It is anticipated that the prophetic compounds would be active as modulators of heme oxygenase-1 signaling, and such activity can be determined using the assay methods described herein below.

In one aspect, a compound can be selected from:

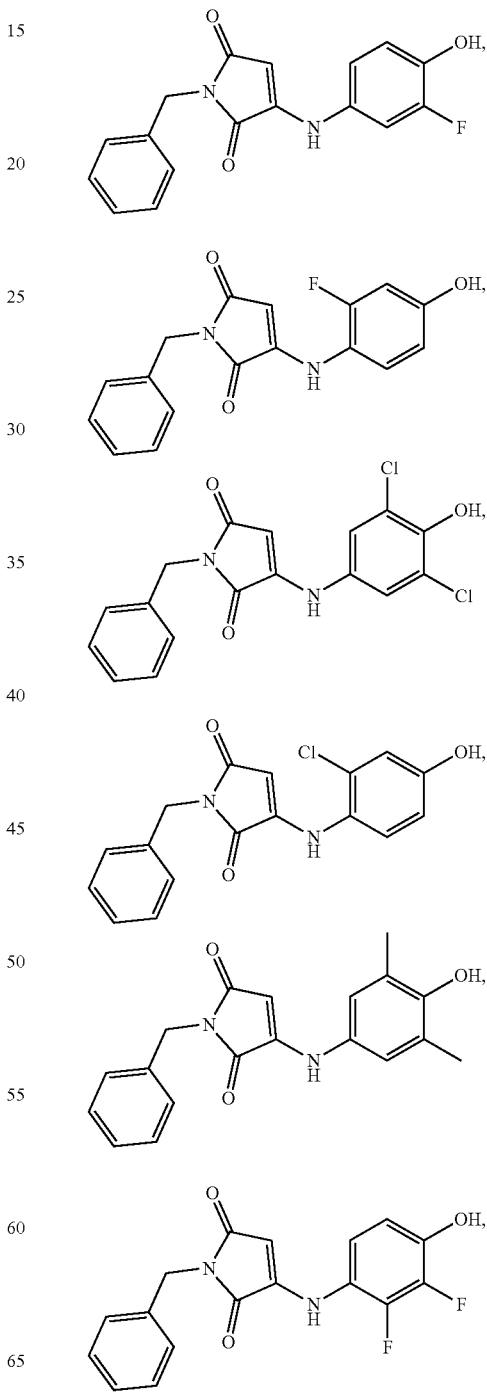

-continued
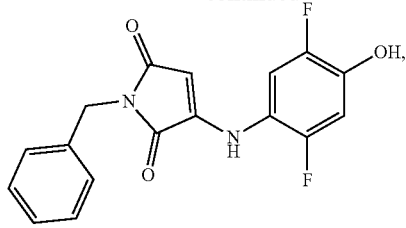
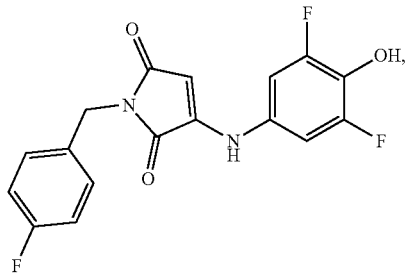
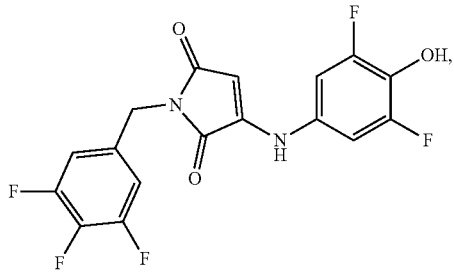
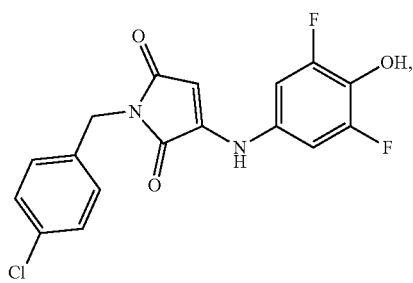
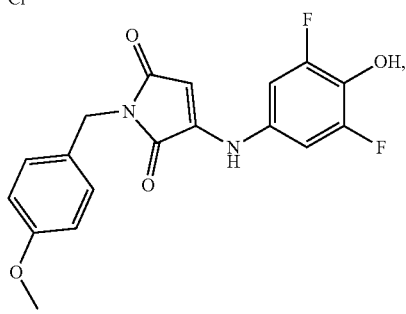
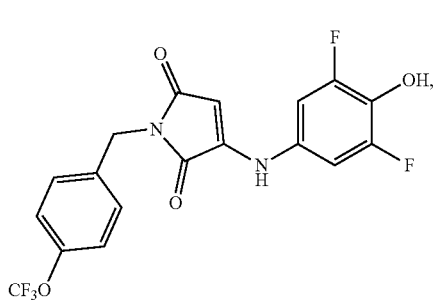
-continued
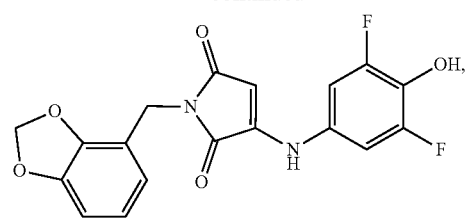
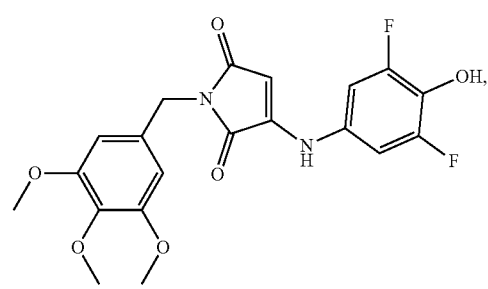
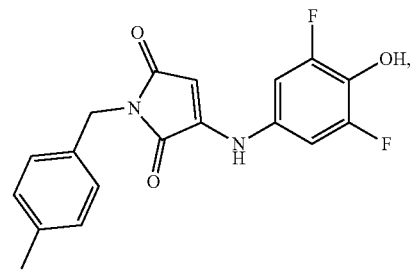
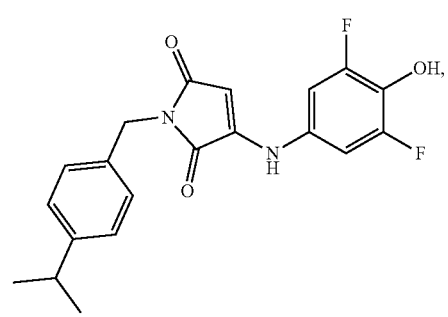
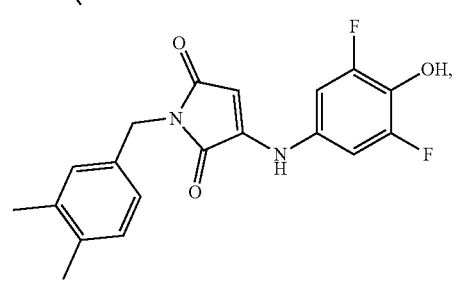
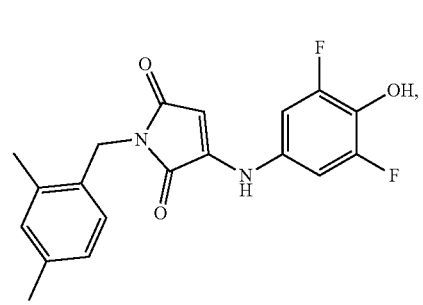

-continued
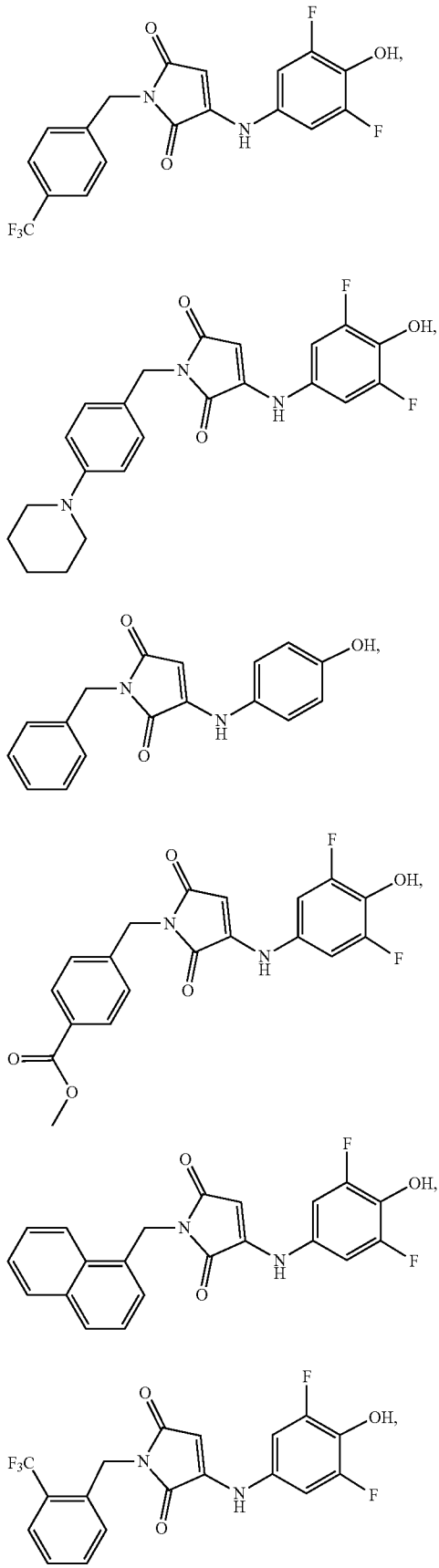
-continued
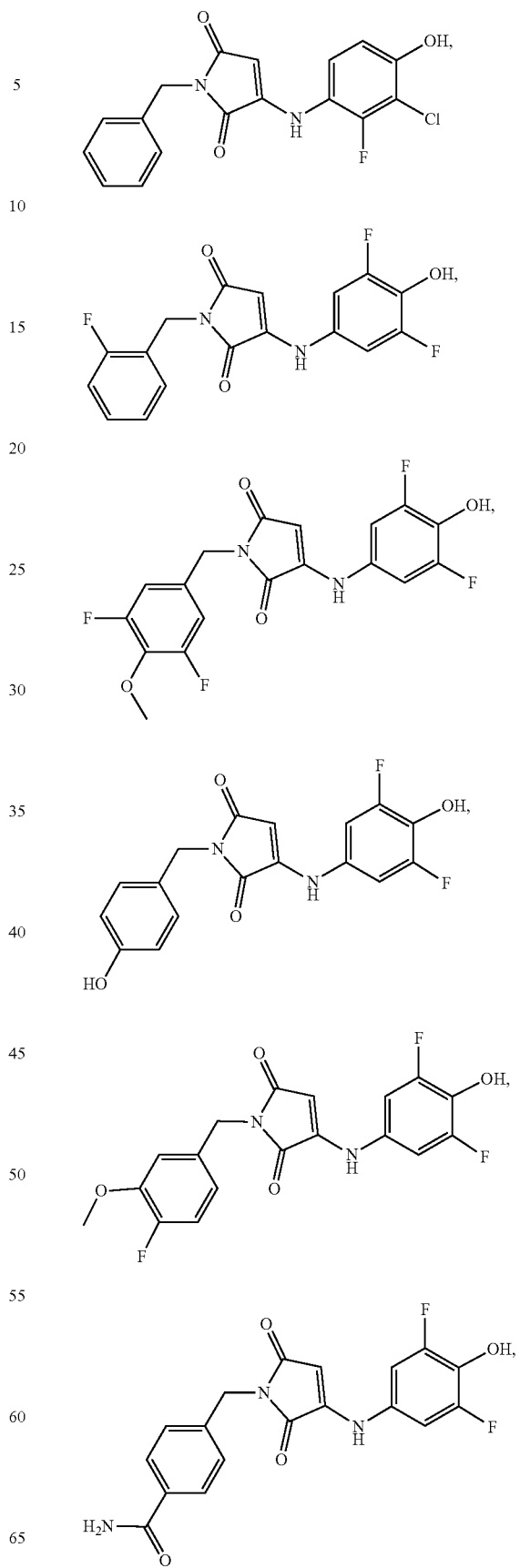

-continued
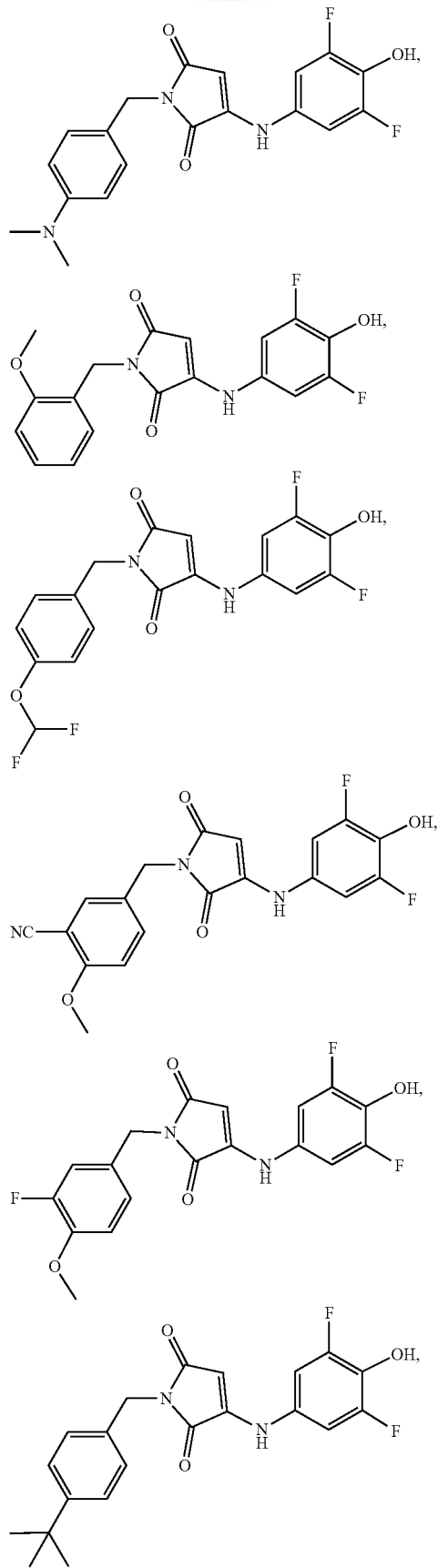
-continued
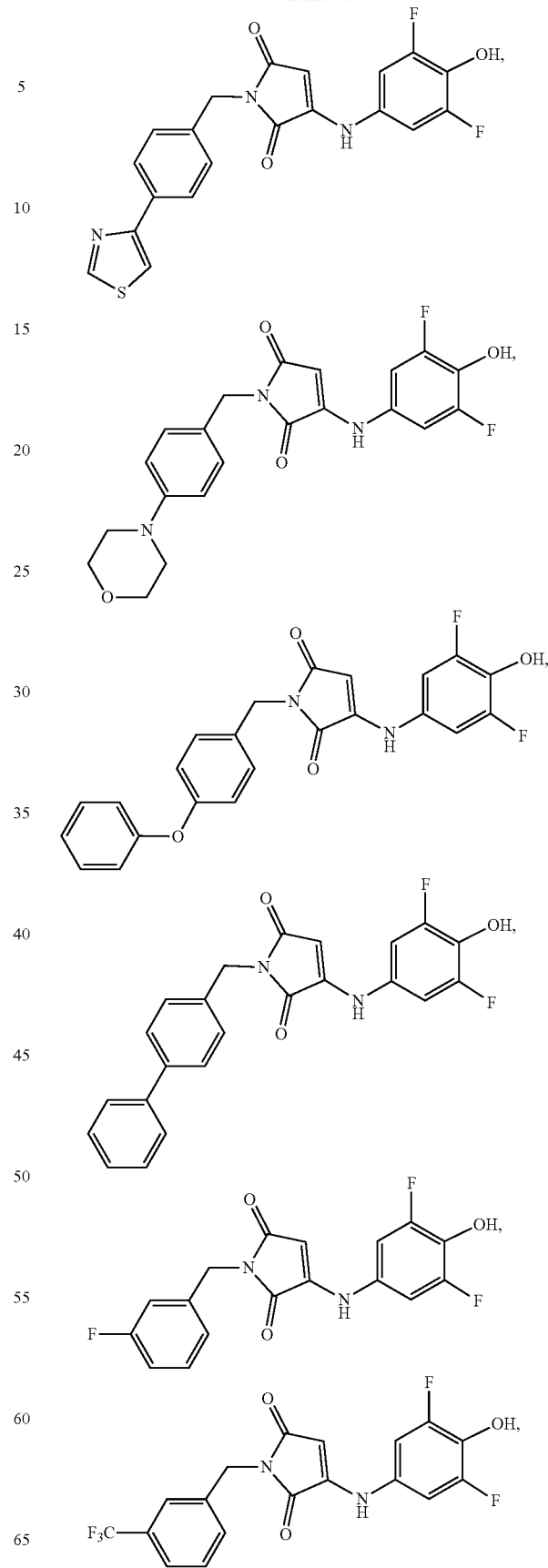

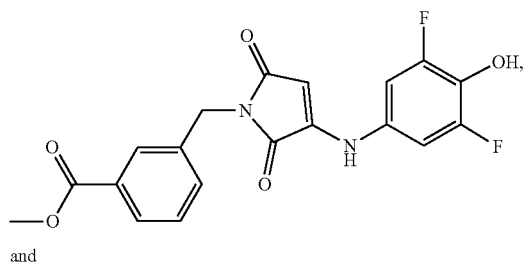
and
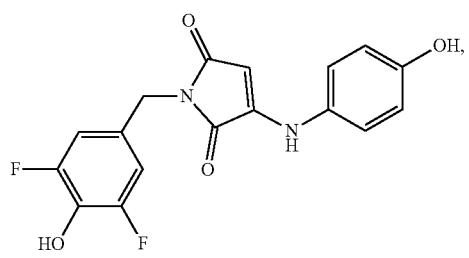
In one aspect, a compound can be selected from:
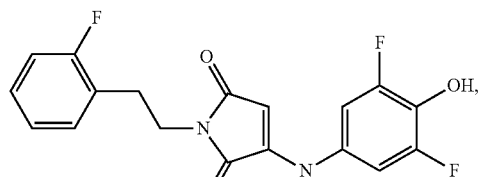
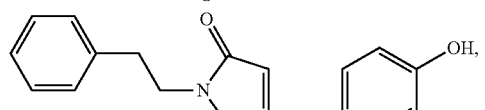
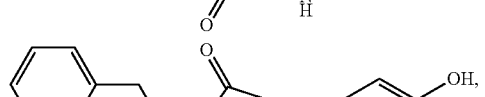
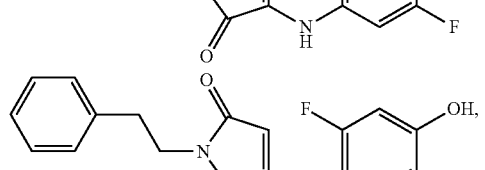
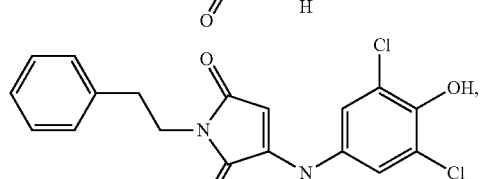
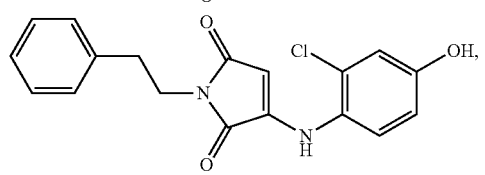
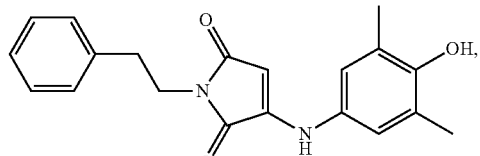
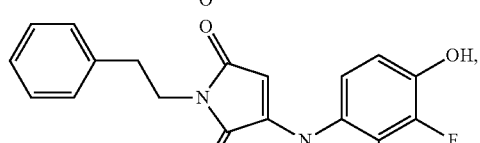
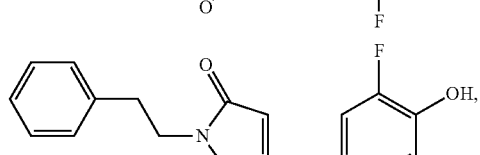
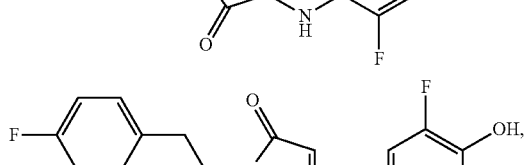
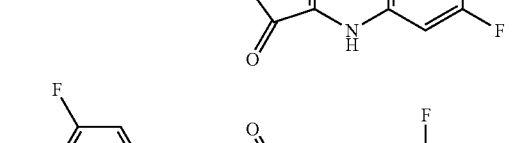
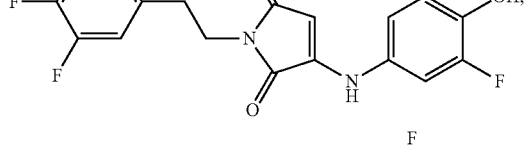
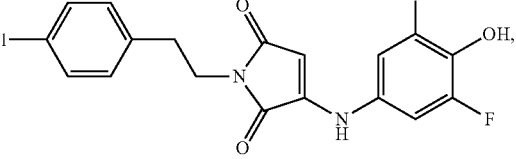
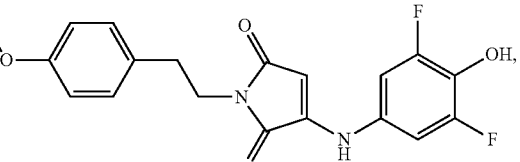
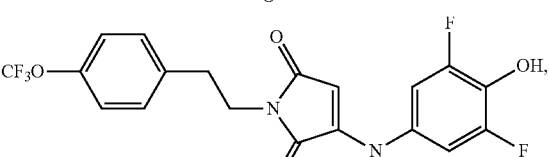
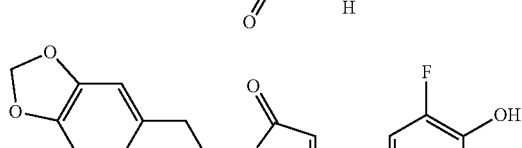
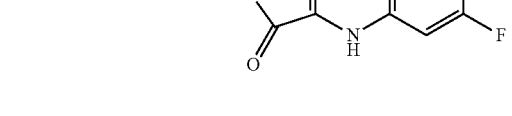

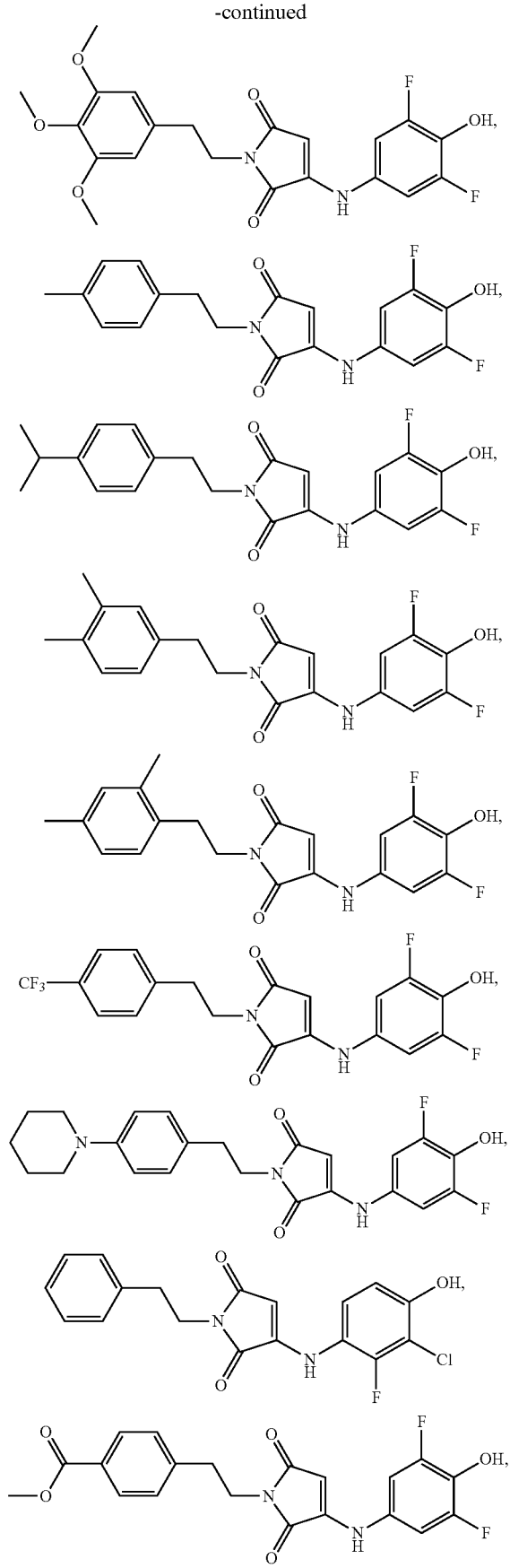
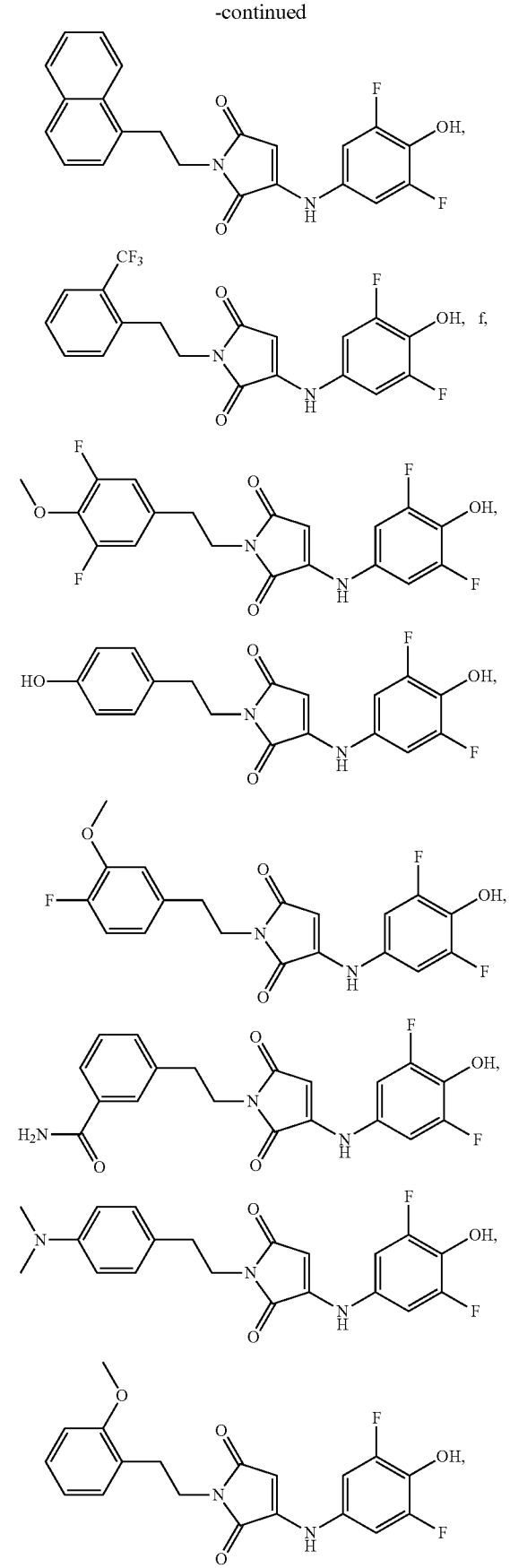

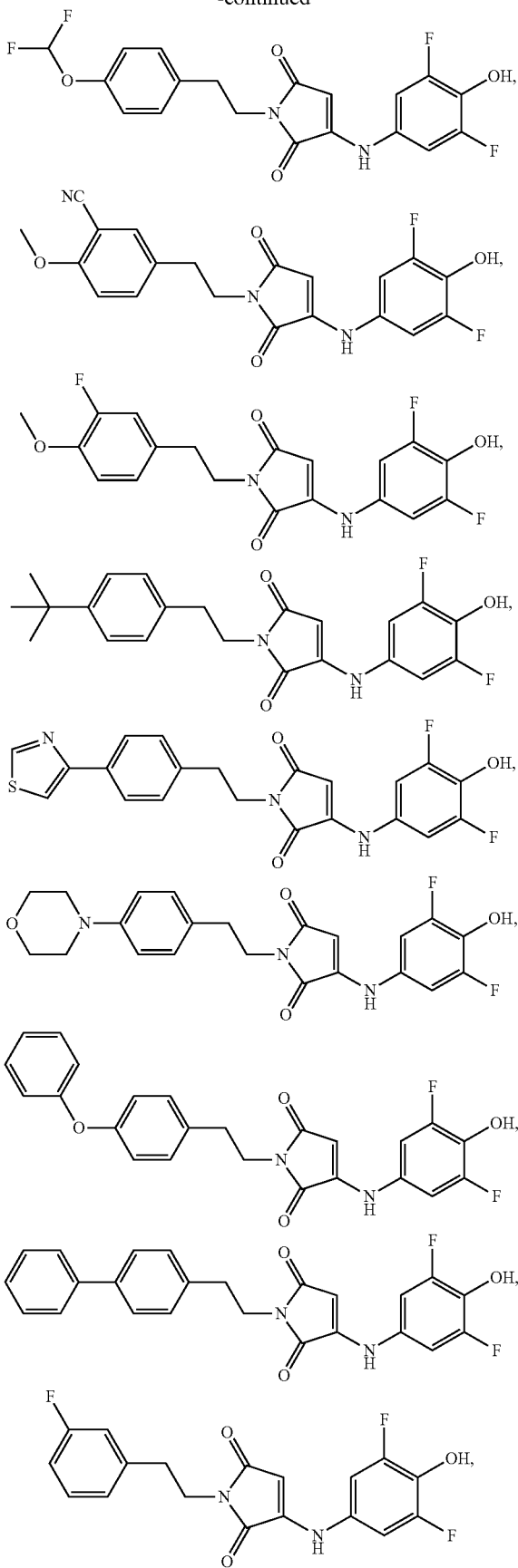
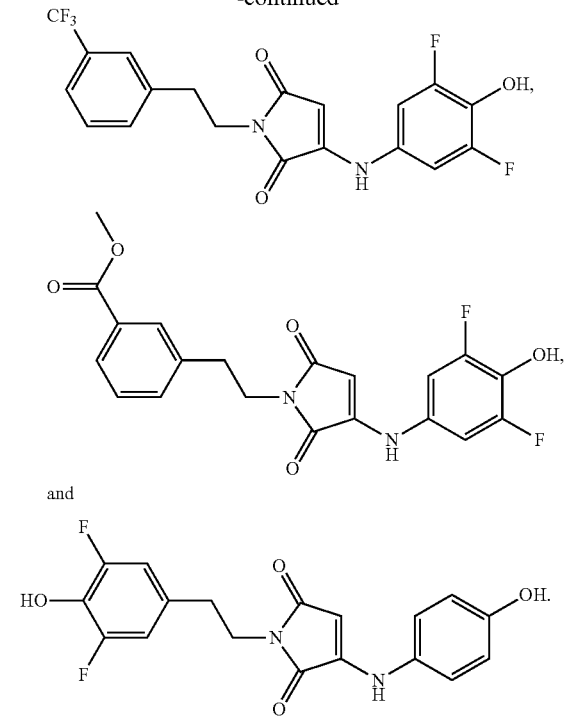
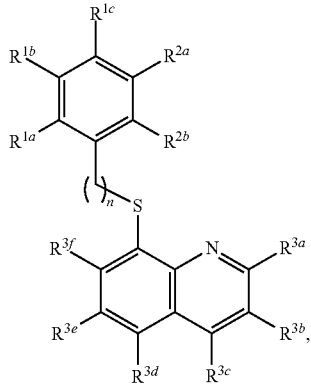

It is contemplated that one or more compounds can optionally be omitted from the disclosed invention.

It is understood that the disclosed compounds can be used in connection with the disclosed methods, compositions, kits, and uses.

It is understood that pharmaceutical acceptable derivatives of the disclosed compounds can be used also in connection with the disclosed methods, compositions, kits, and uses. The pharmaceutical acceptable derivatives of the compounds can include any suitable derivative, such as pharmaceutically acceptable salts as discussed below, isomers, radiolabeled analogs, tautomers, and the like.

C. Pharmaceutical Compositions

In one aspect, disclosed are pharmaceutical compositions comprising an effective amount of a disclosed compound and a pharmaceutically acceptable carrier.

Thus, in one aspect, disclosed are pharmaceutical compositions comprising a therapeutically effective amount of a compound having a structure represented by a formula:

wherein n is 1 or 2; wherein each of $R^{1a}$, $R^{1b}$, and $R^{1c}$ is independently selected from hydrogen, halogen, —CN, —NH₂, —OH, —NO₂, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl, provided that at least one of $R^{1a}$, $R^{1b}$, and $R^{1c}$ is —OH, C1-C4 alkoxy, or C1-C4 alkylamino; wherein each of $R^{2a}$ and $R^{2b}$ is independently selected from hydrogen, halogen, —CN, —NH₂, —OH, —NO₂, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; and wherein each of $R^{3a}$, $R^{3b}$, $R^{3c}$, $R^{3d}$, $R^{3e}$, and $R^{3f}$ is independently selected from hydrogen, halogen, —CN, —NH₂, —OH, —NO₂, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl, provided that at least two of $R^{1a}$, $R^{1b}$, $R^{1c}$, $R^{2a}$, and $R^{2b}$ are non-hydrogen groups, and provided that when n is 1, Z is —S—, and $R^{1a}$ is —OH or C1-C4 alkoxy, then exactly two of $R^{1a}$, $R^{1b}$, $R^{1c}$, $R^{2a}$, and $R^{2b}$ are non-hydrogen groups, or a pharmaceutically acceptable salt thereof, and a pharmaceutically acceptable carrier.

In one aspect, disclosed are pharmaceutical compositions comprising a therapeutically effective amount of a compound having a structure represented by a formula:

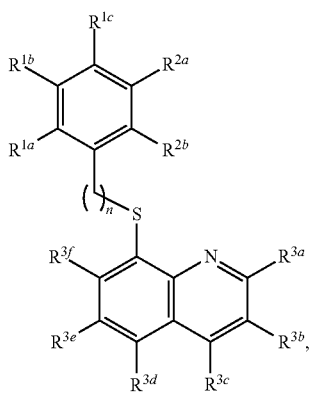

wherein n is 1 or 2; wherein each of $R^{1a}$, $R^{1b}$, and $R^{1c}$ is independently selected from hydrogen, halogen, —CN, —NH₂, —OH, —NO₂, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl, provided that at least one of $R^{1a}$, $R^{1b}$, and $R^{1c}$ is —OH, C1-C4 alkoxy, or C1-C4 alkylamino; wherein each of $R^{2a}$ and $R^{2b}$ is independently selected from hydrogen, halogen, —CN, —NH₂, —OH, —NO₂, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; and wherein each of $R^{3a}$, $R^{3b}$, $R^{3c}$, $R^{3d}$, $R^{3e}$, and $R^{3f}$ is independently selected from hydrogen, halogen, —CN, —NH₂, —OH, —NO₂, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl, provided that at least two of $R^{1a}$, $R^{1b}$, $R^{1c}$, $R^{2a}$, and $R^{2b}$ are non-hydrogen groups, and provided that when n is 1, Z is —S—, and $R^{1a}$ is —OH or C1-C4 alkoxy, then exactly two of $R^{1a}$, $R^{1b}$, $R^{1c}$, $R^{2a}$, and $R^{2b}$ are non-hydrogen groups, and a pharmaceutically acceptable carrier.

In one aspect, disclosed are pharmaceutical compositions comprising a therapeutically effective amount of a compound having a structure selected from:

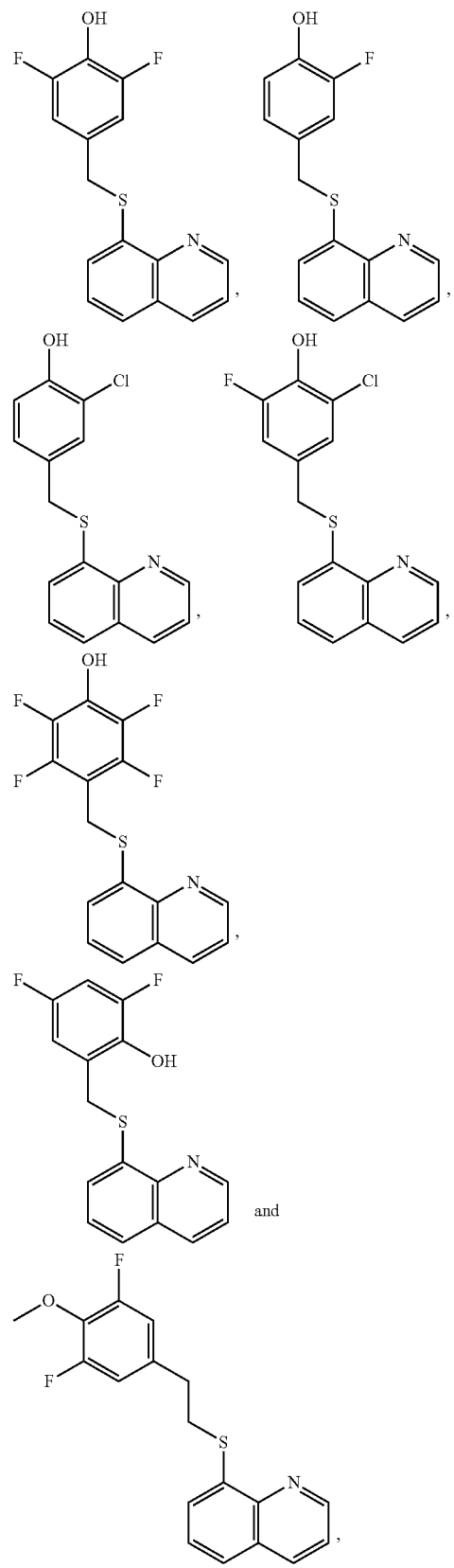

or a pharmaceutically acceptable salt thereof, and a pharmaceutically acceptable carrier.

In one aspect, disclosed are pharmaceutical compositions comprising a therapeutically effective amount of a compound having a structure selected from:

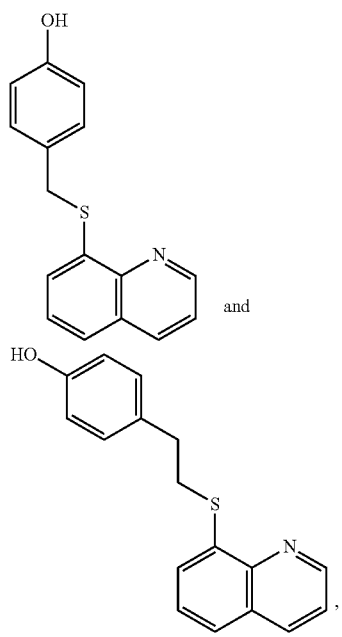

and or a pharmaceutically acceptable salt thereof, and a pharmaceutically acceptable carrier.

In various aspects, the compounds and compositions of the invention can be administered in pharmaceutical compositions, which are formulated according to the intended method of administration. The compounds and compositions described herein can be formulated in a conventional manner using one or more physiologically acceptable carriers or excipients. For example, a pharmaceutical composition can be formulated for local or systemic administration, intravenous, topical, or oral administration.

The nature of the pharmaceutical compositions for administration is dependent on the mode of administration and can readily be determined by one of ordinary skill in the art. In various aspects, the pharmaceutical composition is sterile or sterilizable. The therapeutic compositions featured in the invention can contain carriers or excipients, many of which are known to skilled artisans. Excipients that can be used include buffers (for example, citrate buffer, phosphate buffer, acetate buffer, and bicarbonate buffer), amino acids, urea, alcohols, ascorbic acid, phospholipids, polypeptides (for example, serum albumin), EDTA, sodium chloride, liposomes, mannitol, sorbitol, water, and glycerol. The nucleic acids, polypeptides, small molecules, and other modulatory compounds featured in the invention can be administered by any standard route of administration. For example, administration can be parenteral, intravenous, subcutaneous, or oral. A modulatory compound can be formulated in various ways, according to the corresponding route of administration. For example, liquid solutions can be made for administration by drops into the ear, for injection, or for ingestion; gels or powders can be made for ingestion or topical application. Methods for making such formulations are well known and can be found in, for example, Remington's Pharmaceutical Sciences, 18th Ed., Gennaro, ed., Mack Publishing Co., Easton, Pa. 1990.

In various aspects, the disclosed pharmaceutical compositions comprise the disclosed compounds (including pharmaceutically acceptable salt(s) thereof) as an active ingredient, a pharmaceutically acceptable carrier, and, optionally, other therapeutic ingredients or adjuvants. The instant compositions include those suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions can be conveniently presented in unit dosage form and prepared by any of the methods well known in the art of pharmacy.

In various aspects, the pharmaceutical compositions of this invention can include a pharmaceutically acceptable carrier and a compound or a pharmaceutically acceptable salt of the compounds of the invention. The compounds of the invention, or pharmaceutically acceptable salts thereof, can also be included in pharmaceutical compositions in combination with one or more other therapeutically active compounds.

The pharmaceutical carrier employed can be, for example, a solid, liquid, or gas. Examples of solid carriers include lactose, terra alba, sucrose, talc, gelatin, agar, pectin, acacia, magnesium stearate, and stearic acid. Examples of liquid carriers are sugar syrup, peanut oil, olive oil, and water. Examples of gaseous carriers include carbon dioxide and nitrogen.

In preparing the compositions for oral dosage form, any convenient pharmaceutical media can be employed. For example, water, glycols, oils, alcohols, flavoring agents, preservatives, coloring agents and the like can be used to form oral liquid preparations such as suspensions, elixirs and solutions; while carriers such as starches, sugars, microcrystalline cellulose, diluents, granulating agents, lubricants, binders, disintegrating agents, and the like can be used to form oral solid preparations such as powders, capsules and tablets. Because of their ease of administration, tablets and capsules are the preferred oral dosage units whereby solid pharmaceutical carriers are employed. Optionally, tablets can be coated by standard aqueous or nonaqueous techniques.

A tablet containing the composition of this invention can be prepared by compression or molding, optionally with one or more accessory ingredients or adjuvants. Compressed tablets can be prepared by compressing, in a suitable machine, the active ingredient in a free-flowing form such as powder or granules, optionally mixed with a binder, lubricant, inert diluent, surface active or dispersing agent. Molded tablets can be made by molding in a suitable machine, a mixture of the powdered compound moistened with an inert liquid diluent.

The pharmaceutical compositions of the present invention comprise a compound of the invention (or pharmaceutically acceptable salts thereof) as an active ingredient, a pharmaceutically acceptable carrier, and optionally one or more additional therapeutic agents or adjuvants. The instant compositions include compositions suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions can be conveniently presented in unit dosage form and prepared by any of the methods well known in the art of pharmacy.

Pharmaceutical compositions of the present invention suitable for parenteral administration can be prepared as solutions or suspensions of the active compounds in water. A suitable surfactant can be included such as, for example, hydroxypropylcellulose. Dispersions can also be prepared in glycerol, liquid polyethylene glycols, and mixtures thereof in oils. Further, a preservative can be included to prevent the detrimental growth of microorganisms.

Pharmaceutical compositions of the present invention suitable for injectable use include sterile aqueous solutions or dispersions. Furthermore, the compositions can be in the form of sterile powders for the extemporaneous preparation of such sterile injectable solutions or dispersions. In all cases, the final injectable form must be sterile and must be effectively fluid for easy syringability. The pharmaceutical compositions must be stable under the conditions of manufacture and storage; thus, preferably should be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), vegetable oils, and suitable mixtures thereof.

Pharmaceutical compositions of the present invention can be in a form suitable for topical use such as, for example, an aerosol, cream, ointment, lotion, dusting powder, mouth washes, gargles, and the like. Further, the compositions can be in a form suitable for use in transdermal devices. These formulations can be prepared, utilizing a compound of the invention, or pharmaceutically acceptable salts thereof, via conventional processing methods. As an example, a cream or ointment is prepared by mixing hydrophilic material and water, together with about 5 wt % to about 10 wt % of the compound, to produce a cream or ointment having a desired consistency.

Pharmaceutical compositions of this invention can be in a form suitable for rectal administration wherein the carrier is a solid. It is preferable that the mixture forms unit dose suppositories. Suitable carriers include cocoa butter and other materials commonly used in the art. The suppositories can be conveniently formed by first admixing the composition with the softened or melted carrier(s) followed by chilling and shaping in molds.

In addition to the aforementioned carrier ingredients, the pharmaceutical formulations described above can include, as appropriate, one or more additional carrier ingredients such as diluents, buffers, flavoring agents, binders, surface-active agents, thickeners, lubricants, preservatives (including anti-oxidants) and the like. Furthermore, other adjuvants can be included to render the formulation isotonic with the blood of the intended recipient. Compositions containing a compound of the invention, and/or pharmaceutically acceptable salts thereof, can also be prepared in powder or liquid concentrate form.

In a further aspect, an effective amount is a therapeutically effective amount. In a still further aspect, an effective amount is a prophylactically effective amount.

In a further aspect, the pharmaceutical composition is administered to a mammal. In a still further aspect, the mammal is a human. In an even further aspect, the human is a patient.

In a further aspect, the pharmaceutical composition is used to treat a disorder associated with heme oxygenase-1 (HO-1) signaling such as, for example, kidney diseases including, but not limited to, chronic kidney disease and acute kidney injury.

It is understood that the disclosed compositions can be prepared from the disclosed compounds. It is also understood that the disclosed compositions can be employed in the disclosed methods of using.

D. Methods of Making Thioquinolinones

The compounds of this invention can be prepared by employing reactions as shown in the following schemes, in addition to other standard manipulations that are known in the literature, exemplified in the experimental sections or clear to one skilled in the art. For clarity, examples having a single substituent are shown where multiple substituents are allowed under the definitions disclosed herein.

Reactions used to generate the compounds of this invention are prepared by employing reactions as shown in the following Reaction Schemes, as described and exemplified below. In certain specific examples, the disclosed compounds can be prepared by Route I, as described and exemplified below. The following examples are provided so that the invention might be more fully understood, are illustrative only, and should not be construed as limiting.

1. Route I

In one aspect, substituted thioquinolinones can be prepared as shown below.

SCHEME 1A.

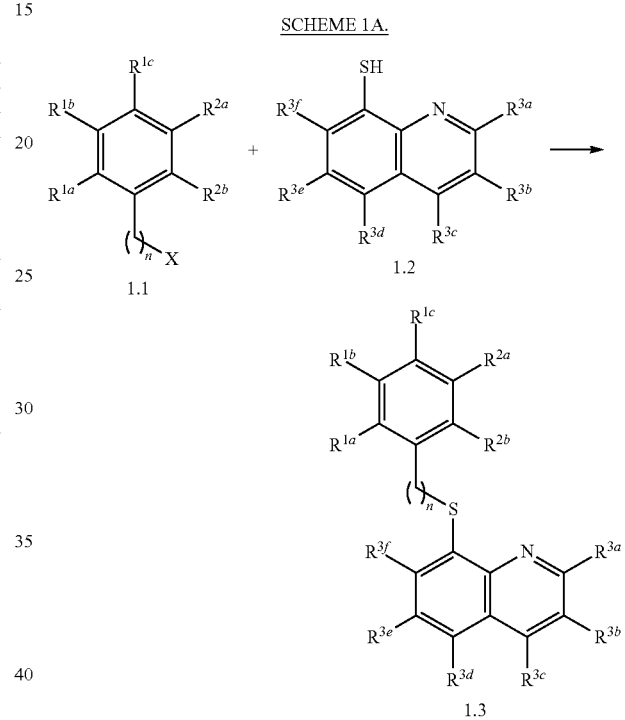

Compounds are represented in generic form, where X is a halogen, and with other substituents as noted in compound descriptions elsewhere herein. A more specific example is set forth below.

SCHEME 1B.

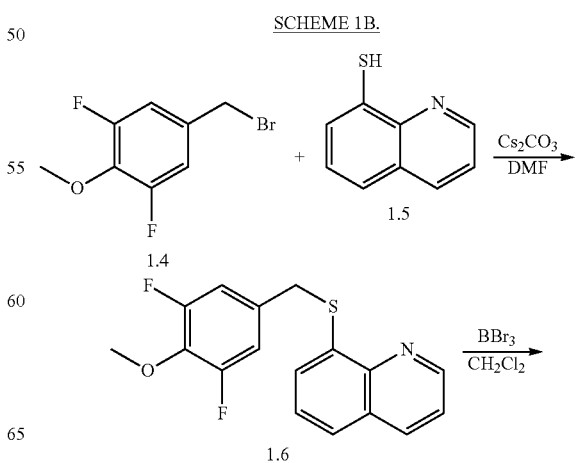

-continued

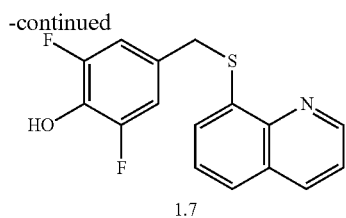

1.7

In one aspect, compounds of type 1.7, and similar compounds, can be prepared according to reaction Scheme 1B above. Thus, compounds of type 1.6 can be prepared by a coupling reaction between an appropriate halide, e.g., 1.4 as shown above, and an appropriate benzenethiol, e.g., 1.5 as shown above. Appropriate halides and appropriate benzenethiol are commercially available or prepared by methods known to one skilled in the art. The coupling reaction is carried out in the presence of an appropriate base, e.g., cesium carbonate, in an appropriate solvent, e.g., dimethylformamide. Compounds of type 1.7 can be prepared by a dealkylation reaction of an appropriate methoxy derivative, e.g., 1.6 as shown above. The dealkylation reaction is carried out in the presence of an appropriate Lewis acid, e.g., boron tribromide, in an appropriate solvent, e.g., dichloromethane. As can be appreciated by one skilled in the art, the above reaction provides an example of a generalized approach wherein compounds similar in structure to the specific reactants above (compounds similar to compounds of type 1.1 and 1.2), can be substituted in the reaction to provide substituted thioquinolinone derivatives similar to Formula 1.3.

E. Treating a Disorder Associated with HO-1 Signaling

In one aspect, disclosed are methods for treating a disorder associated with heme oxygenase-1 signaling in a subject, the method comprising administering to the subject an effective amount of a disclosed compound, thereby treating the disorder.

Thus, in one aspect, disclosed are methods for treating a disorder associated with HO-1 signaling dysfunction in a subject in need thereof, the method comprising administering to the subject an effective amount of a compound having a structure represented by a formula:

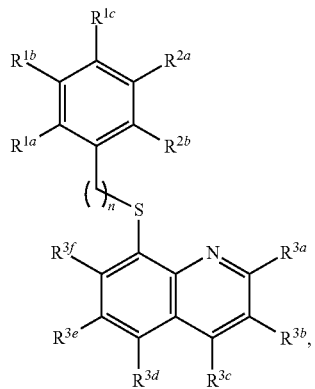

wherein n is 1 or 2; wherein each of $R^{1a}$, $R^{1b}$, and $R^{1c}$ is independently selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl, provided that at least one of $R^{1a}$, $R^{1b}$, and $R^{1c}$ is —OH, C1-C4 alkoxy, or C1-C4 alkylamino; wherein each of $R^{2a}$ and $R^{2b}$ is independently selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; and wherein each of $R^{3a}$, $R^{3b}$, $R^{3c}$, $R^{3d}$, $R^{3e}$, and $R^{3f}$ is independently selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl, provided that at least two of $R^{1a}$, $R^{1b}$, $R^{1c}$, $R^{2a}$, and $R^{2b}$ are non-hydrogen groups, and provided that when n is 1, Z is —S—, and $R^{1a}$ is —OH or C1-C4 alkoxy, then exactly two of $R^{1a}$, $R^{1b}$, $R^{1c}$, $R^{2a}$, and $R^{2b}$ are non-hydrogen groups, or a pharmaceutically acceptable salt thereof, thereby treating the disorder in the subject.

In one aspect, disclosed are methods for treating a disorder associated with HO-1 signaling dysfunction in a subject in need thereof, the method comprising administering to the subject an effective amount of a compound having a structure represented by a formula:

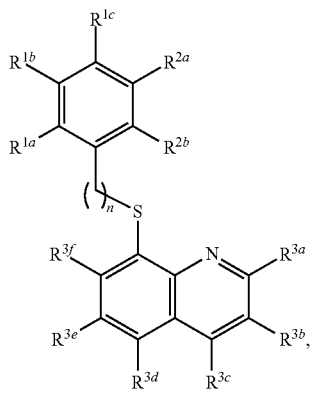

wherein n is 1 or 2; wherein each of $R^{1a}$, $R^{1b}$, and $R^{1c}$ is independently selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl, provided that at least one of $R^{1a}$, $R^{1b}$, and $R^{1c}$ is —OH, C1-C4 alkoxy, or C1-C4 alkylamino; wherein each of $R^{2a}$ and $R^{2b}$ is independently selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; and wherein each of $R^{3a}$, $R^{3b}$, $R^{3c}$, $R^{3d}$, $R^{3e}$, and $R^{3f}$ is independently selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl, provided that at least two of $R^{1a}$, $R^{1b}$, $R^{1c}$, $R^{2a}$, and $R^{2b}$ are non-hydrogen groups, and provided that when n is 1, Z is —S—, and $R^{1a}$ is —OH or C1-C4 alkoxy, then exactly two of $R^{1a}$, $R^{1b}$, $R^{1c}$, $R^{2a}$, and $R^{2b}$ are non-hydrogen groups, or a pharmaceutically acceptable salt thereof, thereby treating the disorder in the subject.

In one aspect, disclosed are methods for treating a disorder associated with HO-1 signaling dysfunction in a subject in need thereof, the method comprising administering to the subject an effective amount of a compound having a structure selected from:

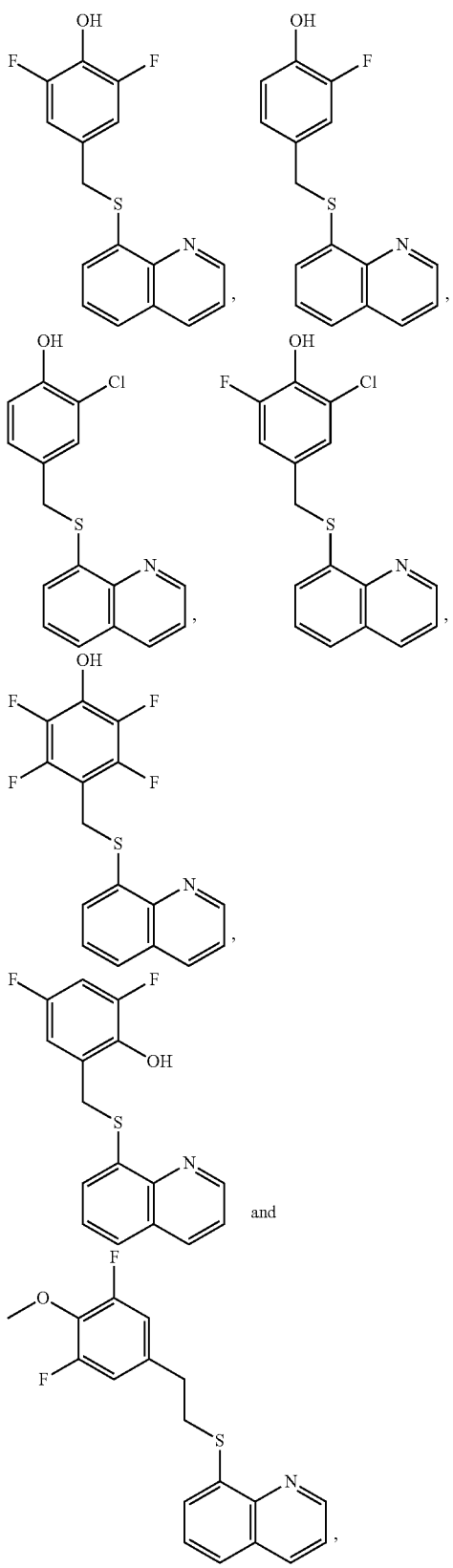

or a pharmaceutically acceptable salt thereof, thereby treating the disorder in the subject.

In one aspect, disclosed are methods for treating a disorder associated with HO-1 signaling dysfunction in a subject in need thereof, the method comprising administering to the subject an effective amount of a compound having a structure selected from:

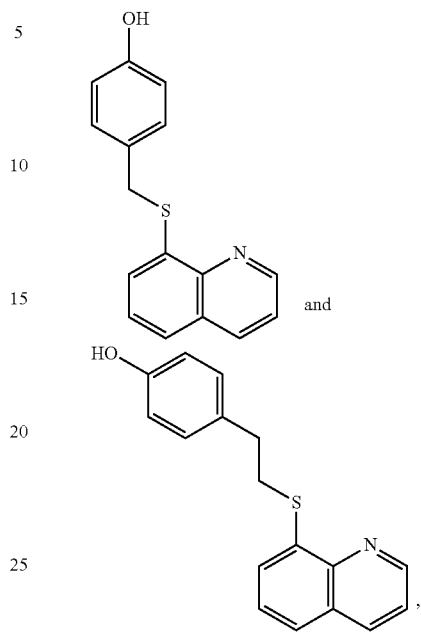

or a pharmaceutically acceptable salt thereof, thereby treating the disorder in the subject.

In a further aspect, the subject has been diagnosed with a need for treatment of the disorder prior to the administering step. In a still further aspect, the subject is at risk for developing the disorder prior to the administering step.

In a further aspect, the subject is a mammal. In a still further aspect, the mammal is a human.

In a further aspect, the method further comprises the step of identifying a subject in need of treatment of the disorder.

In a further aspect, the disorder associated with HO-1 signaling dysfunction is a kidney disease. In a still further aspect, the kidney disease is chronic kidney disease or acute kidney injury (AKI).

In a further aspect, the effective amount is a therapeutically effective amount. In a still further aspect, the effective amount is a prophylactically effective amount.

In a further aspect, the method further comprises the step of administering a therapeutically effective amount of at least one agent associated with the treatment of a disorder associated with HO-1 signaling dysfunction. In a still further aspect, the agent is a an angiotensin-converting enzyme (ACE) inhibitor or an angiotensin II receptor blocker.

In a further aspect, the compound and the agent are administered sequentially. In a still further aspect, the compound and the agent are administered simultaneously.

In a further aspect, the compound and the agent are co-formulated. In a still further aspect, the compound and the agent are co-packaged.

In a further aspect, the compound is administered as a single active agent.

F. Modifying HO-1 Signaling in a Subject

In one aspect, disclosed are methods for modifying HO-1 signaling in a subject, the method comprising administering to the subject an effective amount of a disclosed compound, thereby modifying HO-1 signaling in the subject. Also disclosed are methods for increasing HO-1 signaling in a subject, the method comprising administering a compound that increases HO-1 signaling, wherein the ability of the compound to increase HO-1 signaling is determined by a disclosed method.

Thus, in one aspect, disclosed are methods for modifying HO-1 signaling in a subject, the method comprising administering to the subject an effective amount of a compound having a structure represented by a formula:

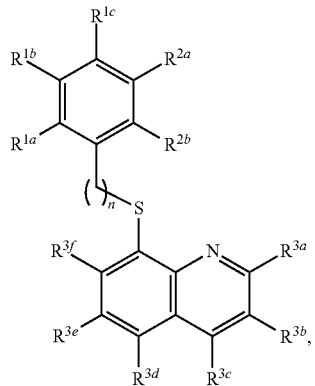

wherein n is 1 or 2; wherein each of $R^{1a}$, $R^{1b}$, and $R^{1c}$ is independently selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl, provided that at least one of $R^{1a}$, $R^{1b}$, and $R^{1c}$ is —OH, C1-C4 alkoxy, or C1-C4 alkylamino; wherein each of $R^{2a}$ and $R^{2b}$ is independently selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; and wherein each of $R^{3a}$, $R^{3b}$, $R^{3c}$, $R^{3d}$, $R^{3e}$, and $R^{3f}$ is independently selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl, provided that at least two of $R^{1a}$, $R^{1b}$, $R^{1c}$, $R^{2a}$, and $R^{2b}$ are non-hydrogen groups, and provided that when n is 1, Z is —S—, and $R^{1a}$ is —OH or C1-C4 alkoxy, then exactly two of $R^{1a}$, $R^{1b}$, $R^{1c}$, $R^{2a}$, and $R^{2b}$ are non-hydrogen groups, or a pharmaceutically acceptable salt thereof, thereby modifying HO-1 signaling in the subject.

In one aspect, disclosed are methods for modifying HO-1 signaling in a subject, the method comprising administering to the subject an effective amount of a compound having a structure represented by a formula:

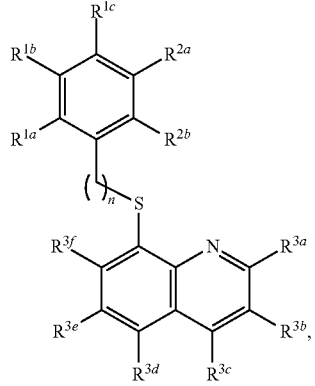

wherein n is 1 or 2; wherein each of $R^{1a}$, $R^{1b}$, and $R^{1c}$ is independently selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl, provided that at least one of $R^{1a}$, $R^{1b}$, and $R^{1c}$ is —OH, C1-C4 alkoxy, or C1-C4 alkylamino; wherein each of $R^{2a}$ and $R^{2b}$ is independently selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; and wherein each of $R^{3a}$, $R^{3b}$, $R^{3c}$, $R^{3d}$, $R^{3e}$, and $R^{3f}$ is independently selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl, provided that at least two of $R^{1a}$, $R^{1b}$, $R^{1c}$, $R^{2a}$, and $R^{2b}$ are non-hydrogen groups, and provided that when n is 1, Z is —S—, and $R^{1a}$ is —OH or C1-C4 alkoxy, then exactly two of $R^{1a}$, $R^{1b}$, $R^{1c}$, $R^{2a}$, and $R^{2b}$ are non-hydrogen groups, or a pharmaceutically acceptable salt thereof, thereby modifying HO-1 signaling in the subject.

In one aspect, disclosed are methods for modifying HO-1 signaling in a subject, the method comprising administering to the subject an effective amount of a compound having a structure selected from:

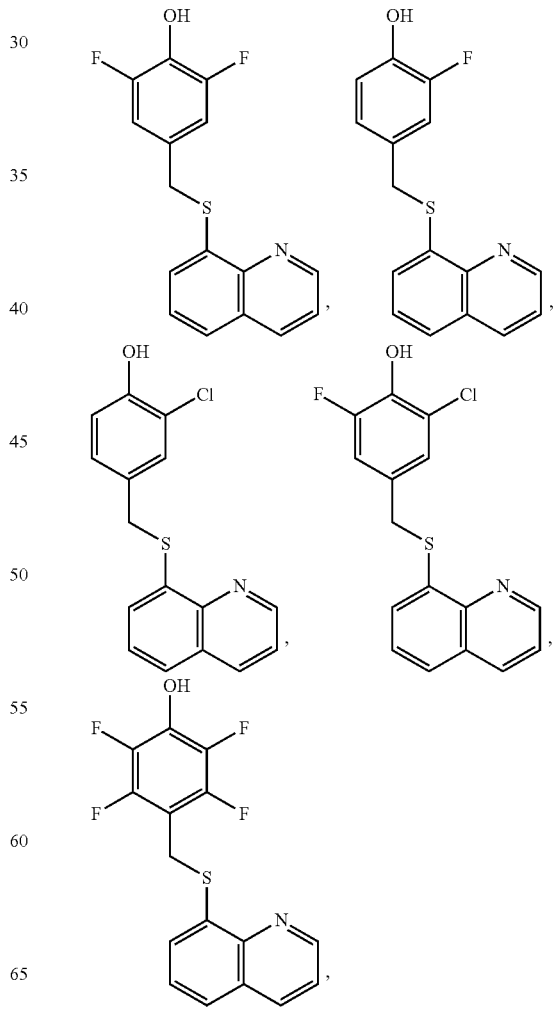

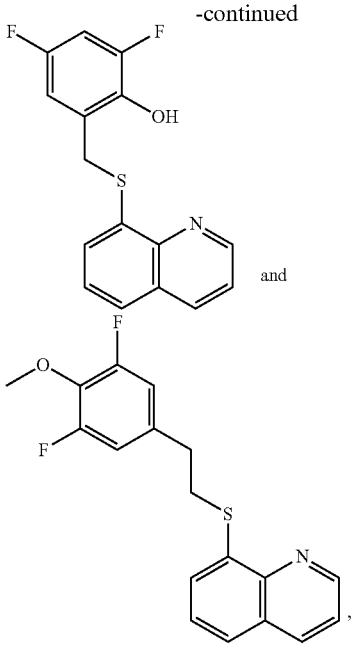

or a pharmaceutically acceptable salt thereof, thereby modifying HO-1 signaling in the subject.

In one aspect, disclosed are methods for modifying HO-1 signaling in a subject, the method comprising administering to the subject an effective amount of a compound having a structure selected from:

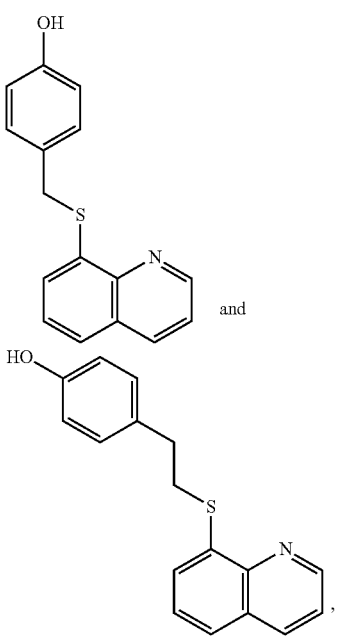

or a pharmaceutically acceptable salt thereof, thereby modifying HO-1 signaling in the subject.

In one aspect, disclosed are methods of increasing heme oxygenase-1 (HO-1) signaling in a subject, the method comprising administering a compound that increases HO-1 signaling, wherein the ability of the compound to increase HO-1 signaling is determined by: (a) contacting a cell with a candidate compound, wherein the cell comprises: (i) a vector comprising: (1) a promoter operably linked to a nucleic acid comprising the sequence of NCBI accession no. Z82244; (2) an enhancer, wherein the enhancer comprises the sequence of SEQ ID NO: 1; and (3) a selectable marker; or (ii) a vector comprising: (1) a promoter operably linked to a nucleic acid comprising a triple mutant of the sequence of NCBI accession no. Z82244; and (2) a selectable marker; wherein the vector expresses HO-1 or a mutant thereof, (b) determining expression of the selectable marker in the cell; and (c) identifying the candidate compound as a compound that that increases HO-1 signaling when expression of the selectable marker is increased in the cell.

In a further aspect, modifying is increasing. In a still further aspect, modifying is activating.

In a further aspect, the subject has been diagnosed with a disorder associated with HO-1 signaling prior to the administering step. In still a further aspect, the subject has been diagnosed with a need for modifying HO-1 signaling prior to the administering step. In yet a further aspect, the subject has been diagnosed with a need for treatment of a disorder associated with HO-I signaling dysfunction prior to the administering step.

In a further aspect, the method further comprises the step of identifying a subject in need of treatment of a disorder associated with HO-I signaling dysfunction.

In a further aspect, the disorder associated with HO-1 signaling dysfunction is a kidney disease. In a still further aspect, the kidney disease is chronic kidney disease or acute kidney injury (AKI).

In a further aspect, the effective amount is a therapeutically effective amount. In a still further aspect, the effective amount is a prophylactically effective amount.

In a further aspect, the method further comprises the step of administering a therapeutically effective amount of at least one agent associated with the treatment of a disorder associated with HO-1 signaling dysfunction. In a still further aspect, the agent is a an angiotensin-converting enzyme (ACE) inhibitor or an angiotensin II receptor blocker.

In a further aspect, the compound and the agent are administered sequentially. In a still further aspect, the compound and the agent are administered simultaneously.

In a further aspect, the compound and the agent are co-formulated. In a still further aspect, the compound and the agent are co-packaged.

In a further aspect, the compound is administered as a single active agent.

G. Modifying HO-I Signaling in at Least One Cell

In one aspect, disclosed are methods for modifying HO-1 signaling in a cell, the method comprising contacting the cell with an effective amount of a disclosed compound, thereby modifying HO-1 signaling in the cell.

Thus, in one aspect, disclosed are methods for modifying HO-1 signaling in a cell, the method comprising contacting the cell with an effective amount of a compound having a structure represented by a formula:

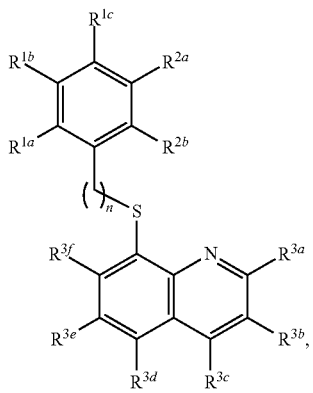

wherein n is 1 or 2; wherein each of $R^{1a}$, $R^{1b}$, and $R^{1c}$ is independently selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl, provided that at least one of $R^{1a}$, $R^{1b}$, and $R^{1c}$ is —OH, C1-C4 alkoxy, or C1-C4 alkylamino; wherein each of $R^{2a}$ and $R^{2b}$ is independently selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; and wherein each of $R^{3a}$, $R^{3b}$, $R^{3e}$, $R^{3d}$, $R^{3e}$, and $R^{31}$ is independently selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl, provided that at least two of $R^{1a}$, $R^{1b}$, $R^{1c}$, $R^{2a}$, and $R^{2b}$ are non-hydrogen groups, and provided that when n is 1, Z is —S—, and $R^{1a}$ is —OH or C1-C4 alkoxy, then exactly two of $R^{1a}$, $R^{1b}$, $R^{1c}$, $R^{2a}$, and $R^{2b}$ are non-hydrogen groups, or a pharmaceutically acceptable salt thereof, thereby modifying HO-1 signaling in the cell.

In one aspect, disclosed are methods for modifying HO-1 signaling in a cell, the method comprising contacting the cell with an effective amount of a compound having a structure represented by a formula:

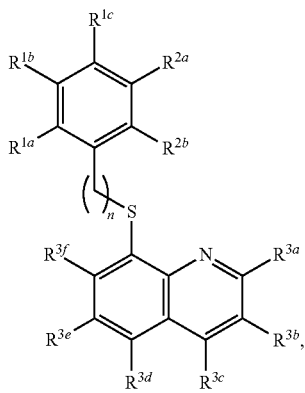

wherein n is 1 or 2; wherein each of $R^{1a}$, $R^{1b}$, and $R^{1c}$ is independently selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl, provided that at least one of $R^{1a}$, $R^{1b}$, and $R^{1c}$ is —OH, C1-C4 alkoxy, or C1-C4 alkylamino; wherein each of $R^{2a}$ and $R^{2b}$ is independently selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; and wherein each of $R^{3a}$, $R^{3b}$, $R^{3e}$, $R^{3d}$, $R^{3e}$, and $R^{31}$ is independently selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl, provided that at least two of $R^{1a}$, $R^{1b}$, $R^{1c}$, $R^{2a}$, and $R^{2b}$ are non-hydrogen groups, and provided that when n is 1, Z is —S—, and $R^{1a}$ is —OH or C1-C4 alkoxy, then exactly two of $R^{1a}$, $R^{1b}$, $R^{1c}$, $R^{2a}$, and $R^{2b}$ are non-hydrogen groups, or a pharmaceutically acceptable salt thereof, thereby modifying HO-1 signaling in the cell.

In one aspect, disclosed are methods for modifying HO-1 signaling in a cell, the method comprising contacting the cell with an effective amount of a compound having a structure selected from:

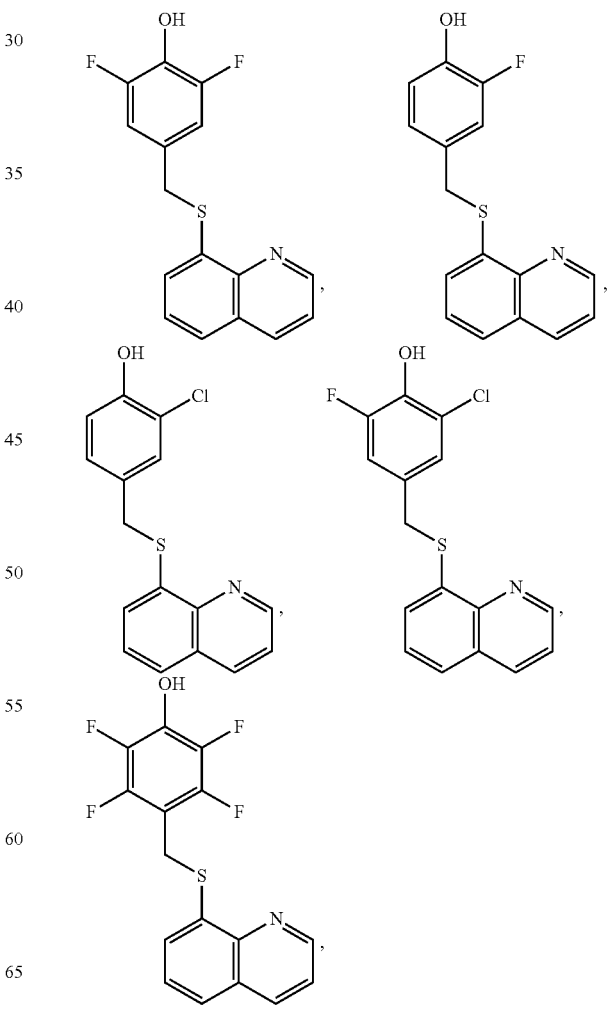

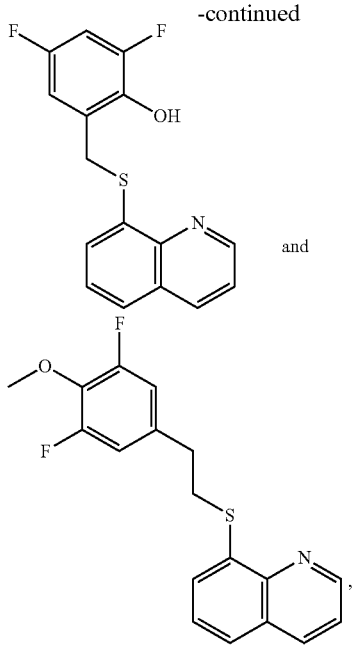

or a pharmaceutically acceptable salt thereof, thereby modifying HO-1 signaling in the cell.

In one aspect, disclosed are methods for modifying HO-1 signaling in a cell, the method comprising contacting the cell with an effective amount of a compound having a structure selected from:

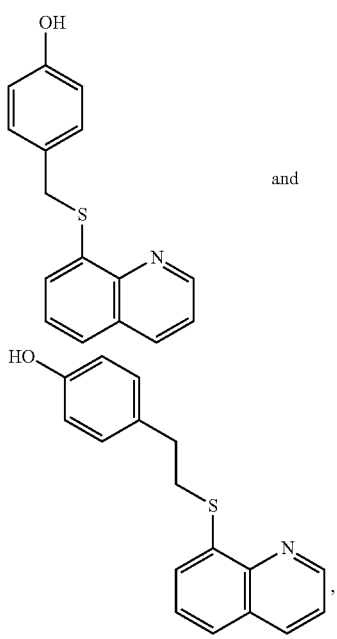

or a pharmaceutically acceptable salt thereof, thereby modifying HO-1 signaling in the cell.

In a further aspect, modifying is increasing. In a still further aspect, modifying is activating.

In a further aspect, the cell is mammalian. In a still further aspect, the cell is human.

In a further aspect, the cell has been isolated from a human prior to the administering step.

In a further aspect, contacting is via administration to a subject. In a still further aspect, the subject has been diagnosed with a need for modification of HO-1 signaling prior to the administering step. In yet a further aspect, the subject has been diagnosed with a need for treatment of a disorder associated with HO-I signaling dysfunction.

In a further aspect, the disorder associated with HO-1 signaling dysfunction is a kidney disease. In a still further aspect, the kidney disease is chronic kidney disease or acute kidney injury (AKI).

H. Identifying a Compound that Modulates HO-1 Signaling

In one aspect, disclosed are methods of identifying a compound that modulates heme oxygenase-1 (HO-1) signaling, the method comprising: (a) contacting a cell with a candidate compound, wherein the cell comprises: (i) a vector comprising: (1) a promoter operably linked to a nucleic acid comprising the sequence of NCBI Accession No. Z82244; (2) an enhancer, wherein the enhancer comprises the sequence of SEQ ID NO: 1; and (3) a selectable marker; or (ii) a vector comprising: (1) a promoter operably linked to a nucleic acid comprising a triple mutant of the sequence of NCBI Accession No. Z82244; and (2) a selectable marker; wherein the vector expresses HO-1 or a mutant thereof, (b) determining expression of the selectable marker in the cell; and (c) identifying the candidate compound as a compound that modulates HO-1 signaling when expression of the selectable marker is modulated in the cell. Also disclosed are compounds that modulate heme oxygenase-1 (HO-1) identified by a disclosed method.

In various aspects, the cell is a eukaryotic cell. In a further aspect, the eukaryotic cell is a mammalian or human cell.

In various aspects, the method further comprises purifying the compound. In a further aspect, the method further comprises isolating the compound.

In various aspects, the selectable marker is a fluorescent marker.

In various aspects, the candidate compound increases expression of the selectable marker in the cell. In a further aspect, the candidate compound decreases expression of the selectable marker in the cell.

In various aspects, the compound that modulates HO-1 identified by a disclosed method has a structure represented by a formula:

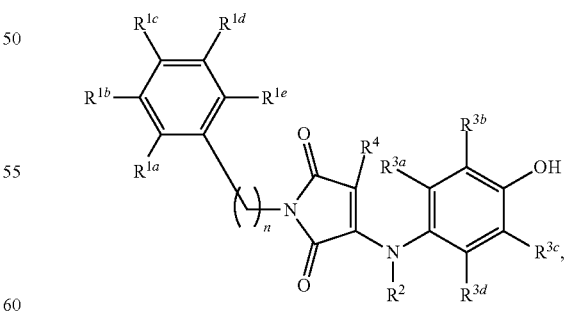

wherein n is 0, 1, or 2; wherein each of $R^{1a}$, $R^{1b}$, $R^{1c}$, $R^{1d}$, and $R^{1e}$ is independently selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, C1-C4 aminoalkyl, —C(O)R$^{10}$, —CO$_2$R$^{11}$, Cy$^1$, and —OCy$^1$; wherein R$^{10}$, when present, is selected from hydrogen, —NH$_2$, C1-C4 alkyl, C1-C4 haloalkyl, C1-C4 alkylamino, (C1-C4)(C1-C4) dialkylamino, and C1-C4 aminoalkyl; wherein R$^{11}$, when present, is selected from hydrogen and C1-C4 alkyl; and wherein Cy$^1$ is selected from C6 aryl, C2-C5 heteroaryl, C3-C6 cycloalkyl, and C2-C5 heterocycloalkyl, and is substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; or wherein two adjoining R$^{1a}$, R$^{1b}$, R$^{1c}$, R$^{1d}$, and R$^{1e}$ groups are covalently bonded and, together with the intermediate atoms, comprise a 5- or 6-membered cycloalkyl, a 5- or 6-membered heterocycloalkyl, a 6-membered aryl, or a 5- or 6-membered heteroaryl, and is substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein R$^2$ is selected from hydrogen and C1-C4 alkyl; wherein each of R$^{3a}$, R$^{3b}$, R$^{3e}$, and R$^{3d}$ is independently selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; and wherein R$^4$ is selected from hydrogen, halogen, and C1-C4 alkyl, or a pharmaceutically acceptable salt thereof, thereby modifying HO-1 signaling in the subject.

In various aspects, the compound that modulates HO-1 identified by a disclosed method has a structure represented by a formula:

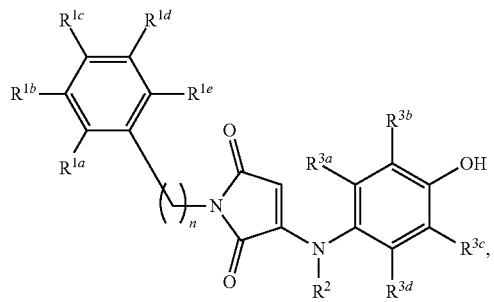

wherein n is 0, 1, or 2; wherein each of R$^{1a}$, R$^{1b}$, R$^{1c}$, R$^{1d}$, and R$^{1e}$ is independently selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, C1-C4 aminoalkyl, —C(O)R$^{10}$, —CO$_2$R$^{11}$, Cy$^1$, and —OCy$^1$; wherein R$^{10}$, when present, is selected from hydrogen, —NH$_2$, C1-C4 alkyl, C1-C4 haloalkyl, C1-C4 alkylamino, (C1-C4)(C1-C4) dialkylamino, and C1-C4 aminoalkyl; wherein R$^{11}$, when present, is selected from hydrogen and C1-C4 alkyl; and wherein Cy$^1$ is selected from C6 aryl, C2-C5 heteroaryl, C3-C6 cycloalkyl, and C2-C5 heterocycloalkyl, and is substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; or wherein two adjoining R$^{1a}$, R$^{1b}$, R$^{1c}$, R$^{1d}$, and R$^{1e}$ groups are covalently bonded and, together with the intermediate atoms, comprise a 5- or 6-membered cycloalkyl, a 5- or 6-membered heterocycloalkyl, a 6-membered aryl, or a 5- or 6-membered heteroaryl, and is substituted with 0, 1, 2, or 3 groups independently selected from halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein R$^2$ is selected from hydrogen and C1-C4 alkyl; and wherein each of R$^{3a}$, R$^{3b}$, R$^{3c}$, and R$^{3d}$ is independently selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl, provided that when one or two of R$^{1a}$, R$^{1b}$, R$^{1c}$, R$^{1d}$, and R$^{1e}$ is —OH or C1-C4 alkoxy and the remaining R$^{1a}$, R$^{1b}$, R$^{1c}$, R$^{1d}$, and R$^{1e}$ groups are hydrogen, then at least two of R$^{3a}$, R$^{3b}$, R$^{3c}$, and R$^{3d}$ are non-hydrogen groups, provided that when one or two of R$^{1a}$, R$^{1b}$, R$^{1c}$, R$^{1d}$, and R$^{1e}$ is —OH or C1-C4 alkoxy and at least one of the remaining R$^{1a}$, R$^{1b}$, R$^{1c}$, R$^{1d}$, and R$^{1e}$ groups is a different non-hydrogen group, then at least one of R$^{3a}$, R$^{3b}$, R$^{3c}$, and R$^{3d}$ are non-hydrogen groups, and provided that when one of R$^{1a}$, R$^{1b}$, R$^{1c}$, R$^{1d}$, and R$^{1e}$ is C1-C4 hydroxyalkyl, then at least one of R$^{1a}$, R$^{1b}$, R$^{1c}$, R$^{1d}$, R$^{1e}$, R$^{3a}$, R$^{3b}$, R$^{3c}$, and R$^{3d}$ is a non-hydrogen group, or a pharmaceutically acceptable salt thereof, thereby modifying HO-1 signaling in the subject.

In various aspects, the compound that modulates HO-1 identified by a disclosed method has a structure selected from:

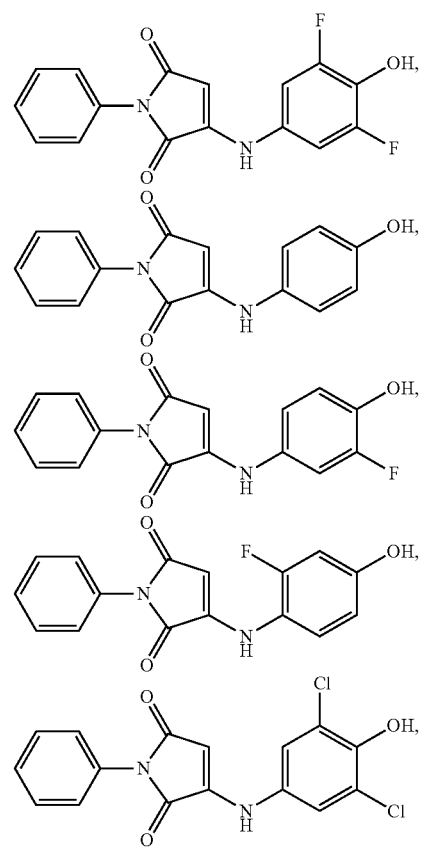

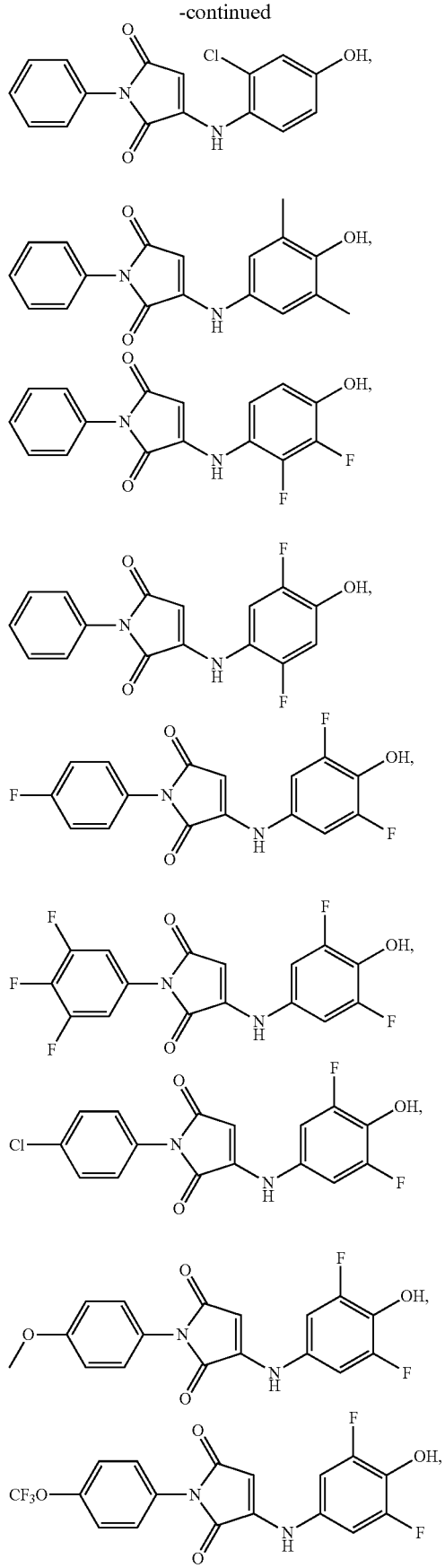
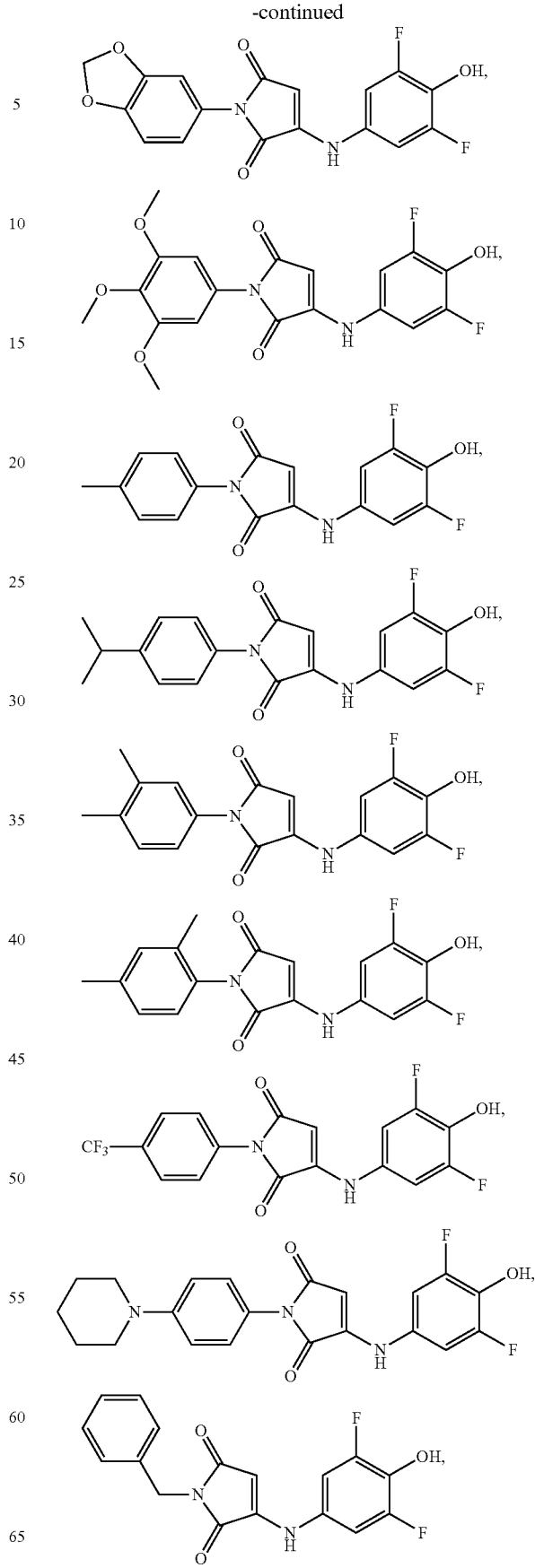

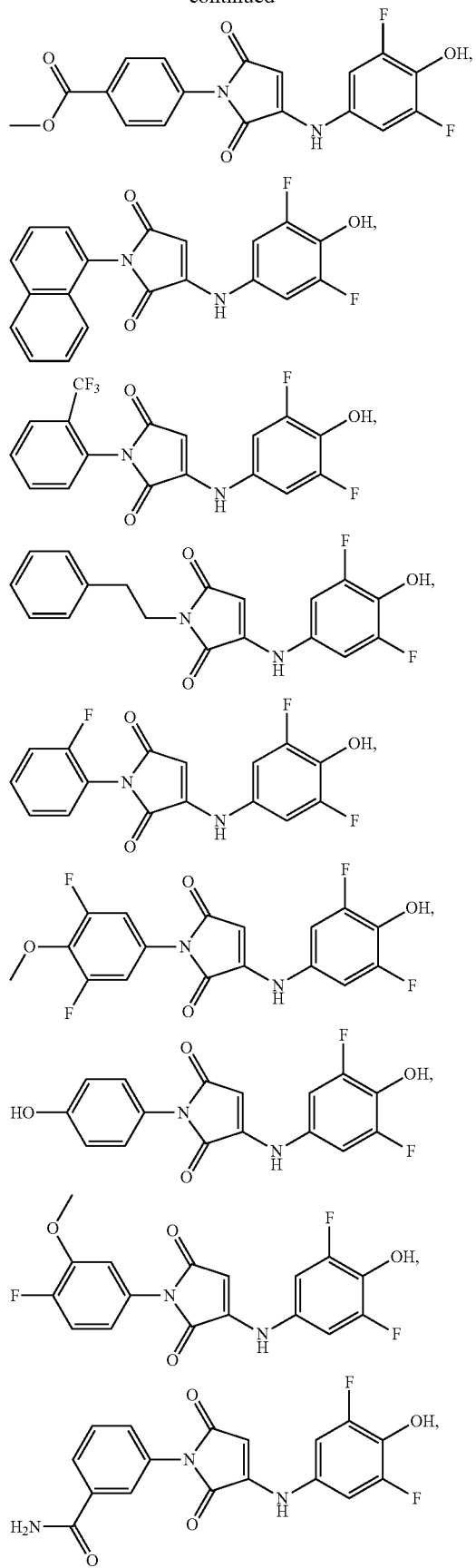
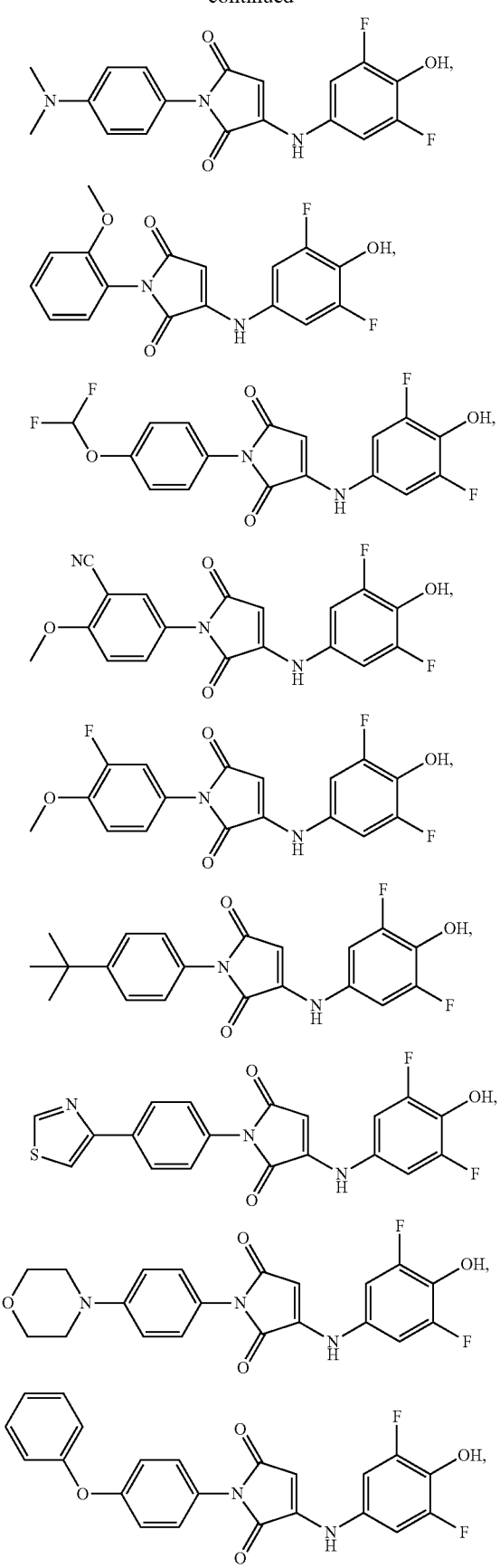

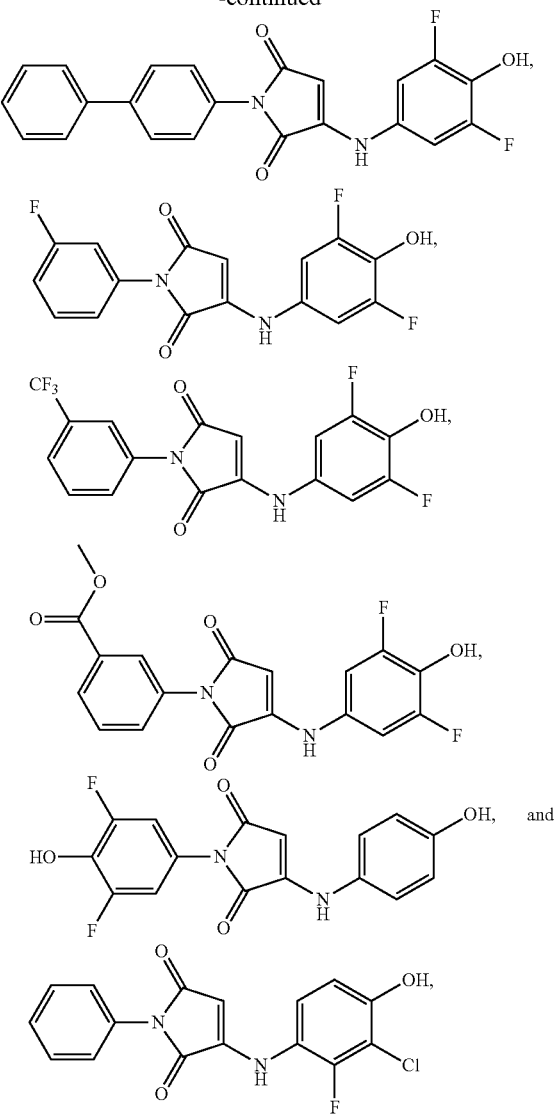

or a pharmaceutically acceptable salt thereof, thereby modifying HO-1 signaling in the subject.

In various aspects, the compound that modulates HO-1 identified by a disclosed method has a structure:

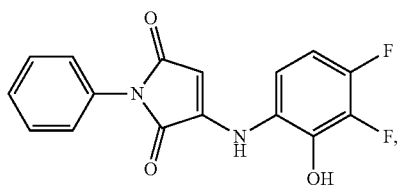 [SMILES: O=C1C=C(Nc2ccc(F)c(F)c2O)C(=O)N1c1ccccc1]

or a pharmaceutically acceptable salt thereof, thereby modifying HO-1 signaling in the subject.

I. Additional Methods of Using the Compounds

The compounds and pharmaceutical compositions of the invention are useful in treating or controlling disorders associated with HO-1 signaling dysfunction, and, in particular, a kidney disease.

Examples of disorders associated with HO-1 signaling dysfunction for which the compounds and compositions can be useful in treating, include, but are not limited to, kidney diseases such as, for example, chronic kidney disease and acute kidney injury.

To treat or control the disorder, the compounds and pharmaceutical compositions comprising the compounds are administered to a subject in need thereof, such as a vertebrate, e.g., a mammal, a fish, a bird, a reptile, or an amphibian. The subject can be a human, non-human primate, horse, pig, rabbit, dog, sheep, goat, cow, cat, guinea pig or rodent. The term does not denote a particular age or sex. Thus, adult and newborn subjects, as well as fetuses, whether male or female, are intended to be covered. The subject is preferably a mammal, such as a human. Prior to administering the compounds or compositions, the subject can be diagnosed with a need for treatment of a disorder associated with HO-1 signaling dysfunction such as a kidney disease.

The compounds or compositions can be administered to the subject according to any method. Such methods are well known to those skilled in the art and include, but are not limited to, oral administration, transdermal administration, administration by inhalation, nasal administration, topical administration, intravaginal administration, ophthalmic administration, intraaural administration, intracerebral administration, rectal administration, sublingual administration, buccal administration and parenteral administration, including injectable such as intravenous administration, intra-arterial administration, intramuscular administration, and subcutaneous administration. Administration can be continuous or intermittent. A preparation can be administered therapeutically; that is, administered to treat an existing disease or condition. A preparation can also be administered prophylactically; that is, administered for prevention of a disorder associated with HO-1 signaling dysfunction such as a kidney disease.

The therapeutically effective amount or dosage of the compound can vary within wide limits. Such a dosage is adjusted to the individual requirements in each particular case including the specific compound(s) being administered, the route of administration, the condition being treated, as well as the patient being treated. In general, in the case of oral or parenteral administration to adult humans weighing approximately 70 Kg or more, a daily dosage of about 10 mg to about 10,000 mg, preferably from about 200 mg to about 1,000 mg, should be appropriate, although the upper limit may be exceeded. The daily dosage can be administered as a single dose or in divided doses, or for parenteral administration, as a continuous infusion. Single dose compositions can contain such amounts or submultiples thereof of the compound or composition to make up the daily dose. The dosage can be adjusted by the individual physician in the event of any contraindications. Dosage can vary, and can be administered in one or more dose administrations daily, for one or several days.

1. Use of Compounds

In one aspect, the invention relates to the use of a disclosed compound or a product of a disclosed method. In a further aspect, a use relates to the manufacture of a medicament for the treatment of a disorder associated with HO-1 signaling dysfunction in a subject.

Also provided are the uses of the disclosed compounds and products. In one aspect, the invention relates to use of at least one disclosed compound; or a pharmaceutically acceptable salt, hydrate, solvate, or polymorph thereof. In a further aspect, the compound used is a product of a disclosed method of making.

In a further aspect, the use relates to a process for preparing a pharmaceutical composition comprising a therapeutically effective amount of a disclosed compound or a product of a disclosed method of making, or a pharmaceutically acceptable salt, solvate, or polymorph thereof, for use as a medicament.

In a further aspect, the use relates to a process for preparing a pharmaceutical composition comprising a therapeutically effective amount of a disclosed compound or a product of a disclosed method of making, or a pharmaceutically acceptable salt, solvate, or polymorph thereof, wherein a pharmaceutically acceptable carrier is intimately mixed with a therapeutically effective amount of the compound or the product of a disclosed method of making.

In various aspects, the use relates to a treatment of a disorder associated with HO-1 signaling dysfunction in a subject. In one aspect, the use is characterized in that the subject is a human. In one aspect, the use is characterized in that the disorder associated with HO-1 signaling dysfunction is a kidney disease.

In a further aspect, the use relates to the manufacture of a medicament for the treatment of a disorder associated with HO-1 signaling dysfunction in a subject.

It is understood that the disclosed uses can be employed in connection with the disclosed compounds, products of disclosed methods of making, methods, compositions, and kits. In a further aspect, the invention relates to the use of a disclosed compound or a disclosed product in the manufacture of a medicament for the treatment of a disorder associated with HO-1 signaling dysfunction in a mammal. In a further aspect, the disorder associated with HO-1 signaling dysfunction is a kidney disease.

2. Manufacture of a Medicament

In one aspect, the invention relates to a method for the manufacture of a medicament for treating a disorder associated with HO-1 signaling dysfunction in a subject having the disorder, the method comprising combining a therapeutically effective amount of a disclosed compound or product of a disclosed method with a pharmaceutically acceptable carrier or diluent.

As regards these applications, the present method includes the administration to an animal, particularly a mammal, and more particularly a human, of a therapeutically effective amount of the compound effective in the treatment of a disorder associated with HO-1 signaling dysfunction (e.g., a kidney disease). The dose administered to an animal, particularly a human, in the context of the present invention should be sufficient to affect a therapeutic response in the animal over a reasonable timeframe. One skilled in the art will recognize that dosage will depend upon a variety of factors including the condition of the animal and the body weight of the animal.

The total amount of the compound of the present disclosure administered in a typical treatment is preferably between about 0.05 mg/kg and about 100 mg/kg of body weight for mice, and more preferably between 0.05 mg/kg and about 50 mg/kg of body weight for mice, and between about 100 mg/kg and about 500 mg/kg of body weight for humans, and more preferably between 200 mg/kg and about 400 mg/kg of body weight for humans per daily dose. This total amount is typically, but not necessarily, administered as a series of smaller doses over a period of about one time per day to about three times per day for about 24 months, and preferably over a period of twice per day for about 12 months.

The size of the dose also will be determined by the route, timing and frequency of administration as well as the existence, nature and extent of any adverse side effects that might accompany the administration of the compound and the desired physiological effect. It will be appreciated by one of skill in the art that various conditions or disease states, in particular chronic conditions or disease states, may require prolonged treatment involving multiple administrations.

Thus, in one aspect, the invention relates to the manufacture of a medicament comprising combining a disclosed compound or a product of a disclosed method of making, or a pharmaceutically acceptable salt, solvate, or polymorph thereof, with a pharmaceutically acceptable carrier or diluent.

3. Kits

In one aspect, disclosed are kits comprising a disclosed compound, and one or more of: (a) an agent associated with the treatment of a disorder associated with HO-1 signaling dysfunction; (b) instructions for administering the compound in connection with treating a disorder associated with HO-1 signaling dysfunction; and (c) instructions for treating a disorder associated with HO-1 signaling dysfunction.

Thus, in one aspect, disclosed are kits comprising a compound having a structure represented by a formula:

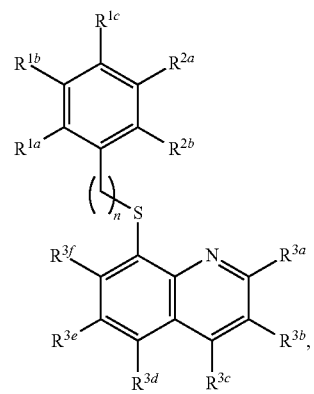

wherein n is 1 or 2; wherein each of $R^{1a}$, $R^{1b}$, and $R^{1c}$ is independently selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl, provided that at least one of $R^{1a}$, $R^{1b}$, and $R^{1c}$ is —OH, C1-C4 alkoxy, or C1-C4 alkylamino; wherein each of $R^{2a}$ and $R^{2b}$ is independently selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; and wherein each of $R^{3a}$, $R^{3b}$, $R^{3c}$, $R^{3d}$, $R^{3e}$, and $R^{3f}$ is independently selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl, provided that at least two of $R^{1a}$, $R^{1b}$, $R^{1c}$, $R^{2a}$, and $R^{2b}$ are non-hydrogen groups, and provided that when n is 1, Z is —S—, and $R^{1a}$ is —OH or C1-C4 alkoxy, then exactly two of $R^{1a}$, $R^{1b}$, $R^{1c}$, $R^{2a}$, and $R^{2b}$ are non-hydrogen groups, or a pharmaceutically acceptable salt thereof, and one or more of: (a) an agent associated with the treatment of a disorder associated with HO-1 signaling dysfunction; (b) instructions for administering the compound in connection with treating a disorder associated with HO-1 signaling dysfunction; and (c) instructions for treating a disorder associated with HO-1 signaling dysfunction.

In one aspect, disclosed are kits comprising a compound having a structure represented by a formula:

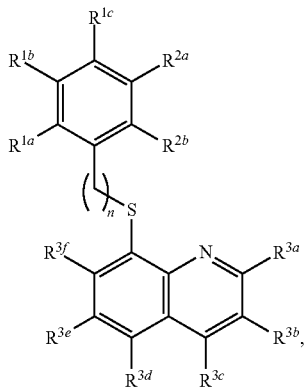

wherein n is 1 or 2; wherein each of $R^{1a}$, $R^{1b}$, and $R^{1c}$ is independently selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl, provided that at least one of $R^{1a}$, $R^{1b}$, and $R^{1c}$ is —OH, C1-C4 alkoxy, or C1-C4 alkylamino; wherein each of $R^{2a}$ and $R^{2b}$ is independently selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; and wherein each of $R^{3a}$, $R^{3b}$, $R^{3c}$, $R^{3d}$, $R^{3e}$, and $R^{3f}$ is independently selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl, provided that at least two of $R^{1a}$, $R^{1b}$, $R^{1c}$, $R^{2a}$, and $R^{2b}$ are non-hydrogen groups, and provided that when n is 1, Z is —S—, and $R^{1a}$ is —OH or C1-C4 alkoxy, then exactly two of $R^{1a}$, $R^{1b}$, $R^{1c}$, $R^{2a}$, and $R^{2b}$ are non-hydrogen groups, or a pharmaceutically acceptable salt thereof, and one or more of: (a) an agent associated with the treatment of a disorder associated with HO-1 signaling dysfunction; (b) instructions for administering the compound in connection with treating a disorder associated with HO-1 signaling dysfunction; and (c) instructions for treating a disorder associated with HO-1 signaling dysfunction.

In one aspect, disclosed are kits comprising a compound having a structure selected from:

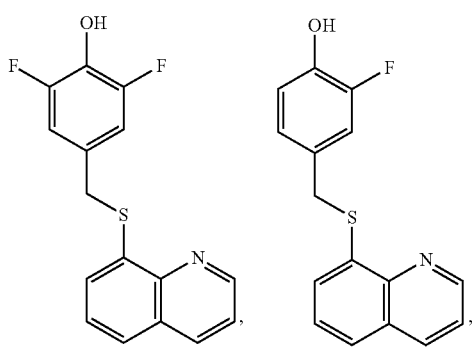

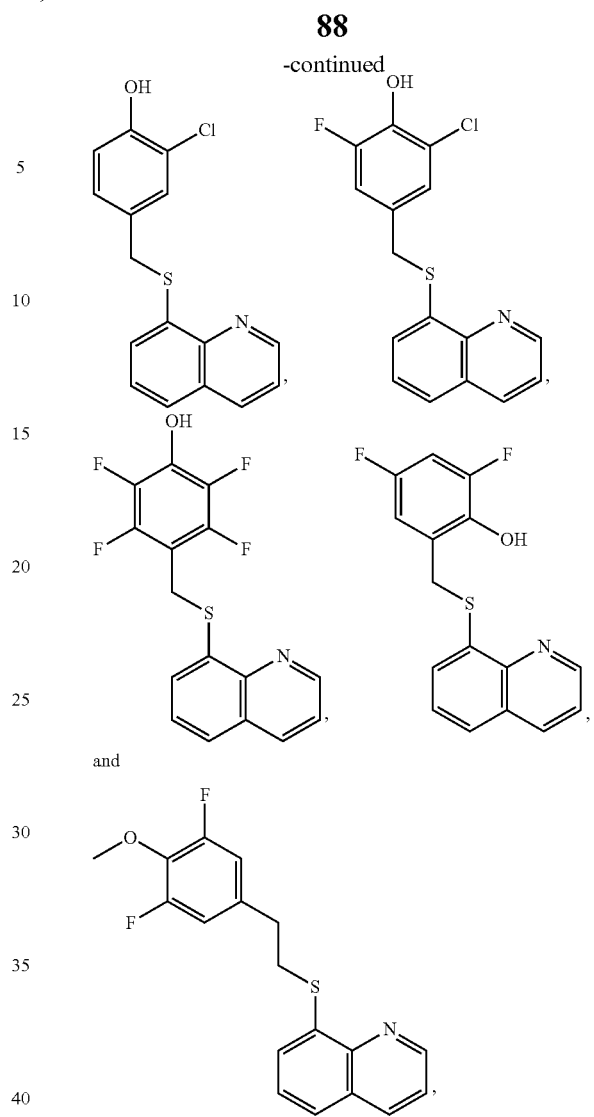

or a pharmaceutically acceptable salt thereof, and one or more of: (a) an agent associated with the treatment of a disorder associated with HO-1 signaling dysfunction; (b) instructions for administering the compound in connection with treating a disorder associated with HO-1 signaling dysfunction; and (c) instructions for treating a disorder associated with HO-1 signaling dysfunction.

In one aspect, disclosed are kits comprising a compound having a structure selected from:

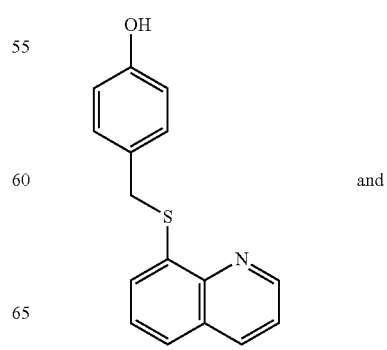

-continued or a pharmaceutically acceptable salt thereof, and one or more of: (a) an agent associated with the treatment of a disorder associated with HO-1 signaling dysfunction; (b) instructions for administering the compound in connection with treating a disorder associated with HO-1 signaling dysfunction; and (c) instructions for treating a disorder associated with HO-1 signaling dysfunction.

In a further aspect, the disorder associated with HO-1 signaling dysfunction is a kidney disease. In a still further aspect, the kidney disease chronic kidney disease or acute kidney injury (AKI).

In a further aspect, the agent is an angiotensin-converting enzyme (ACE) inhibitor or an angiotensin II receptor blocker.

In a further aspect, the compound and the agent are co-formulated. In a further aspect, the compound and the agent are co-packaged.

The kits can also comprise compounds and/or products co-packaged, co-formulated, and/or co-delivered with other components. For example, a drug manufacturer, a drug reseller, a physician, a compounding shop, or a pharmacist can provide a kit comprising a disclosed compound and/or product and another component for delivery to a patient.

It is understood that the disclosed kits can be prepared from the disclosed compounds, products, and pharmaceutical compositions. It is also understood that the disclosed kits can be employed in connection with the disclosed methods of using.

The foregoing description illustrates and describes the disclosure. Additionally, the disclosure shows and describes only the preferred embodiments but, as mentioned above, it is to be understood that it is capable to use in various other combinations, modifications, and environments and is capable of changes or modifications within the scope of the invention concepts as expressed herein, commensurate with the above teachings and/or the skill or knowledge of the relevant art. The embodiments described herein above are further intended to explain best modes known by applicant and to enable others skilled in the art to utilize the disclosure in such, or other, embodiments and with the various modifications required by the particular applications or uses thereof. Accordingly, the description is not intended to limit the invention to the form disclosed herein. Also, it is intended to the appended claims be construed to include alternative embodiments.

All publications and patent applications cited in this specification are herein incorporated by reference, and for any and all purposes, as if each individual publication or patent application were specifically and individually indicated to be incorporated by reference. In the event of an inconsistency between the present disclosure and any publications or patent application incorporated herein by reference, the present disclosure controls.

J. EXAMPLES

The following examples are put forth so as to provide those of ordinary skill in the art with a complete disclosure and description of how the compounds, compositions, articles, devices and/or methods claimed herein are made and evaluated, and are intended to be purely exemplary of the invention and are not intended to limit the scope of what the inventors regard as their invention. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

The Examples are provided herein to illustrate the invention, and should not be construed as limiting the invention in any way. Examples are provided herein to illustrate the invention and should not be construed as limiting the invention in any way.

1. Generation of pHOGL3/4.5+220

The generation of the pHOGL3/4.5+220 construct is described in Deshane, et al. (2010) "Sp1 regulates chromatin looping between an intronic enhancer and distal promoter of the human heme oxygenase-1 gene in renal cells" *J Biol Chem* 285(22): 16476-86. See also FIG. 1.

Briefly, BamHI sites were added to the 4.5-kb PCR product generated by long-range PCR from a bacterial artificial chromosome clone containing portions of chromosome 22 (accession no. Z82244), including the HO-1 gene. This fragment was cloned into the BglII restriction site of the multiple cloning region to make the parental clone (pHOGL3/4.5). The 220-bp intronic enhancer was amplified with SalI sites on either end and cloned into the SalI site of the vector to generate pHOGL3/4.5+220.

2. Generation of pHOGL3/4.5+220 and pHOGL3/Triple Mutant

Figure 2:
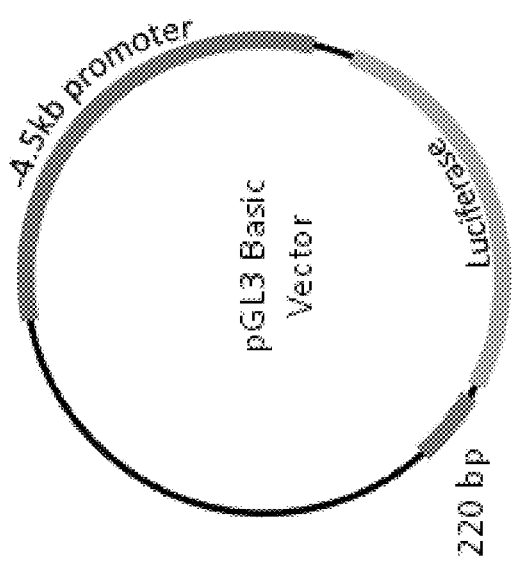
FIG. 2 shows a representative schematic of a pHOGL3/Triple Mutant construct.

The Triple Mutant used for the counter-screen is described in Liby, et al. (2005) "The synthetic triterpenoids, CDDO and CDDO-imidazolide, are potent inducers of heme oxygenase-1 and Nrf2/ARE signaling" *Cancer Res* 65(11): 4789. See also FIG. 2.

Briefly, pHOGL3/4.5 was used as the parental clone. Mutations and deletions were made sequentially using the QuikChange XL site-directed mutagenesis kit to create the pHOGL3/Triple Mutant.

3. DNA SEQUENCES
The DNA sequence for the 220-bp enhancer is as follows:

(SEQ ID NO: 1)
acaaggctgcatcttaaagcgattgagaacgtggcctgaatgaggatgggagtctcttgaaggcctgccc acaggtgggaggctcagcagttgggaaggacccaccccagccagctttgtgttcacctttcccatttc ctcctcagcatgccccaggatttgtcagaggccctgaaggaggccaccaaggaggtgcacacccaggcag agaa.

-continued

The DNA sequence for the 4.5-kb promoter is as follows:

(SEQ ID NO: 2)
gcccagggtccttcctgccttccttggcaggtgggtccctgacctcctgcattgtggtcactcccaacca aacacctcccgggaggcggaagttgcaatgagccaagatcaggccattgcactccagtgtgggcaacaag agcaaagctccatctcaaaaaaaaaaaaaaaaaaaaaaaaaaagttgcccttcgaatccaagggctgct gttttgcaagtggatgaaggctttccctgagtattcctcttgcttcctcccacctcctcctgtaactga aggattgtcctgtcctccttaagcattcattctgcatgttaccccagcaggaccaggaaccccaaataca aattttcctctattcctctaatcacttccatgcccttctcaagatgcatcaagaccctcaaggtcaggcc gggcacggtggctcaagcctggaatcccagcactttgggaggctgaggagggcggatcacgaggtcagga gatcaagaccatcctggctaacacagtgaaacctggtctctactaaaaacacaaaaaattagccgggcgt ggtcgcgggcacctgtagtcccagctactcgggaggctgaggcaggagaatggtgtgaacccgggaggcg gagcttgcagtcacccaagatcgcgccaccgcactccagcctgggcaacagagcgaaacccccgtcacaaa aaaaaaaagaaaaagaaaaaaagaaaaaaaaagaccctcaaggtcatattcaagggaaggaagtcca gcccccttgaggcagctggctgaaaaacaggtttctcatatactaaaagaacttgggaaatgggaatcag aaatggataatcattttgttgctagcatgctccaagctagggtcattataaggtgatggagacaaggaca taggctggcccaaggccacaggcacaggagacaaaaatacccgcaggacagagatgaaggctgatcccag gctaacagatgaccattagaacacagatgaaggccaggttaaactggtttattctggaaccccaaggatg aagagggagcccccggttcacttcagtatctcctctgttctcagtgggtaattatgatgagatgggcca aggttaagggtacacagtaagactggttcattccgaaaccctaaggatgaatgaggaacgccctgttcag gaaaggataacaggaaaataagaggatgccttcttttctgttttttttttctgctttgttctctctttgc aggtgggtaatcacgtcaccgtatgtcaggacatgcccctgcattctcaaaaactgggaagtttgatcac ccaaatcttggaacaaaaagccacttttccttttgaatactgtttggcctaaaaatgaactgggagaaaa ttacaaaagtcagcctttctttctccaaaagaatccagtgcctctatgcaggaaatcctcaaattagcct tctcaggtcttttataatcaacagcagaatgaggaggacagggataaagagacagagaaatgcagggaac agagagaggctcaactattggctgttttataagccctccagccccacccaggttgccctcagaatcccct cctaggtaactgccatcagcgccagaagccaggccactggcagataaactgcccccatgggataaatggg gaaaagccccacatagcttgttcccttgccacaagctcagccactggaaacgggactgccctgagggtc ataggaaccccccaggacagaatcccaacccctgatggccatgagctgaaggggttctctgccctggct ggcttccaaatcagacattgtcattaacaggacaaagccaagggtaactttggaggcggcaagtaaaatt ataaatttccctcttgagttcaagagctgcctactctgtgctaatctcccttatctgagcaactctcttcc aaatcctgagggtaatgggggaaaatggcaccttctttctccaaaagaaaaaaatctttatattactta agggaccaaggagtttgagaccagcctgggcaacatagtgagaccctgtctccatcagaaacacaaaaaa attagccaggtggacgtggtggcacaggcctgtggtcctagctacttgggaggctagggtgggaggatcg cttgagcccgggtgatggaggctgcagtgagccgagatcgtgccactgcactccagcctgagtgacagag tgagaccccatcgcaaaaaaaaaaaaaataagtcaaggatgatgatgatatagactcagggaatatcat taagtgaacgagaaattatctttattccccacttttaacatggggaaactgaggccccaggaagacaacc aagtattggctgaattgagctgagggagatctcaaatcactcaatagcgaccaccaccttcccaggcagc tatcgaagttcccataatgggcagatggatcacctggggtcaggagttcgagaccagcctggccaacatg ataaaacccatctctactaaaaaatacaaaattagccggatgtggtataattacagctgtaatccca gctactagggaggatgaggcaggaaaattgcttgaacctgggagacaggttgcagtgagccgaaatcacg ccactgcactccagcctgggcgacagagcaagactcgtcaaaaaaaaaaaaaaaaaaaggccgggtgcg gtggctcacacctgtaatcacagcactttgggaggctgaggcaggtggatcacgaggtcaggagttcaag

```
                                    -continued
acctgcctggccaaaatggtgaaaccccatctgtactaaaaatacaaaaattagctgggcatggtgatg ggtgcctgtaatcccagctactcgggaggctgaggcagagaattgcttgaacccaggaggcagaggttgc agtgagccaagatcgtgccactgcactccagcctgggtgacagagcaagactccatctcaaaaaaaaaaa aaaaaaaagttcccacggtgctgccgagcctgtgattggcagaggcattgtttattcgttcaaggtttt ttgttaagggacccggtgagtatcaactactaggcagttctcacttctgctcacttctgggctcacttaa gcctaccagcagccctgaaggctgttaaccaccctttagagcttagagagtcgaagaggcagggggccagg tcctaaagaaaggcacactgtcccccagagcctggggcgcgatgccacccgcccccccccccccgcccag gcgtaccccccttaccccgcccccacccgctcgccgcgcccagcccatctggcgccgctctgcccctg ctgagtaatcctttcccgagccacgtggccgtgttttcctgctgagtcacggtcccgaggtctattttc gctaagtcaccgccccgagatctgttttcgctgagtcacggtcccggtgtctgttttcgctgagtcacgg tctagagatttgttttcctcagagttccagctgctccaggtttaatcccctggggcaaagtccggactgt ccggctggagtctggagtcgggacatgcctcagccagcacgtcctcggcctcgtctgggcctgaatcct agggaagccatagcagctcctccaccttcctctcactcctcctctagcctcttgctactccccgcacca ctgttttagggaacctctatctcccgacggcctgccacgggccaggcgctgtgctgggggcttcacactt taaatcgctgttgagcgggcgcggggcgctgcaacctaaaggtgggagctactcaaatggaggggcat ctgttaaaatggccggcctgtcattttcaaaaacttcaaggccgggcgcggtggctcacgcctgtaatcc cagcactttgggaggccgaggcgggcggatcacgaggtcaggagatcgagatcatcttgtctaacacggt gaaacttcatctctactaaaaatagaaaaaattagccgggcgtggtggcgggcgcctgtaatcccagcta ctcaggaggctgaggcaggagaatggcatgaacccgggaggcggagcttgcagtgagccgaaatcgcgcc actgcagtccggcctgggcgaaagagcaagactccgcctcaaaaaaaaaaaaaaaaaaaaacttcaaagg ctgaggaacccaaagaggcaggacaagtgaatgcaatgcaacctcttgggctggaacctggactggtaaa acggctaaagaggaggttattggggcaatagggacatttgaatataggctttatattgaaggagttcag gatatgccacccaaaatgtgccactttggattaaggatcattattattattattattattttgagac agggtctctgtcacccaagctgcagtgcagtggcacaatctcggctcactgcaacctctgcctcctaggt tcaagcgattctcgtgcctc.
```

4. Generation of Stable Cell Lines

In order to generate cells that stably express luciferase expression vectors that lack a mammalian antibiotic selection cassette, HEK293 cells were co-transfected with either pHOGL3/4.5+220 (Deshane et al, 2010) or the Triple Mutant construct (Liby, Hock et al, 2005; Hock et al, 2007) and pcDNA3.1 Zeocin using Lipofectamine 2000. Cells were cultured in Zeocin (400 ug/ml; Invitrogen) for selection. Individual clones were sorted by flow cytometry and plated into a 96-well plate at a density of one cell per well. Clones were maintained and expanded in complete media (DMEM/10% FBS/1× antibiotic-antimycotic) supplemented with 100 ug/ml Zeocin, and incubated at 37° C. in 5% carbon dioxide. Incorporation of the Luciferase expression vectors was validated by assaying for luciferase.

5. High Throughput Screen (HTS)

A library of over 150,000 compounds, as well as a library of over 4,000 FDA approved compounds, were used in the HTS assay. To identify false positive hits, a secondary screen was employed using a similar stable cell line in which three point mutations in the promoter region render it inactive. This led to the identification of approximately 800 compounds that induce HO-1 and have desirable chemical structures. Compounds exhibiting $E_{max} \geq 70\%$ of 5 µM hemin and $EC_{50} < 10$ µM were assayed for endogenous HO-1 expression in HEK-293 cells. The In-Cell Western assay was optimized to screen for endogenous HO-1 in a high throughput platform, and results were validated by Western blot, real-time PCR, and enzyme activity assays. Additional RNA sequencing studies highlighted a role for the transcription factor Nrf2 and other targets in HO-1 induction by several small molecules. Furthermore, the ability of these compounds to inhibit cisplatin-induced cytotoxicity in HEK-293 cells was demonstrated.

6. Chemistry Experimentals

All reactions were carried out in an oven-dried glassware under argon atmosphere using standard gas-tight syringe, cannula, and septa. The reaction temperatures were measured externally. Stirring was achieved with oven dried magnetic bars. All the reactions were done in anhydrous solvents ($CH_2Cl_2$, THF, MeOH) purchased from Sigma-Aldrich. All commercially purchased reagents were used without purification. The reactions were monitored by thin-layer chromatography (TLC) on a pre-coated silica gel (60 F254) glass plates from EMD Millipore and visualized using UV light (254 nm). Purification of the compounds was performed on Teledyne-ISCO Combiflash Rf 200 purification systemby using Redisep Rf® normal phase silica gel columns 230-400 mesh. ESI-MS spectra were recorded on a BioTof-2 time-of-flight mass spectrometer. Proton NMR spectra were recorded on a Varian Unity 400 NMR spectrometer operating at 400 MHz calibrated to the solvent peak and TMS peak. The chemical formula and Exact Mass for target compounds were determined from the (M+H)+ by high resolution mass spectroscopy using an Agilent 6210 Electrospray Time of Flight.

a. Representative Synthesis of Compound 1

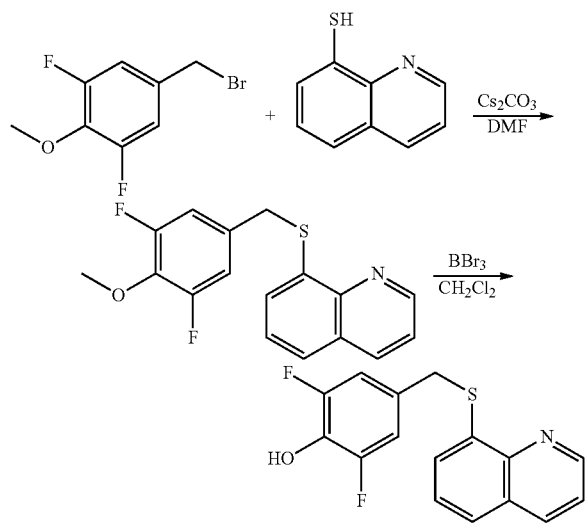

All exemplary compounds were prepared as illustrated above and described more fully below for compound no. 1.

Briefly, a solution of quinoline-8-thiol hydrochloride (250 g, 1.27 mmol), 5-(bromomethyl)-1,3-difluoro-2-methoxybenzene (360 g, 1.52 mmol) and cesium carbonate (1.24 g, 3.8 mmol) in DMF (2 mL) was stirred at rt overnight. DMF was removed from the reaction mixture and the resulted residue was washed with water (20 mL). The aqueous layer was extracted with $CH_2Cl_2$ (3 times) and the combined organic layer was dried over anhydrous $Na_2SO_4$. The filtrate was concentrated in vacuo and the crude product was purified on Teledyne Isco Combiflash® Rf purification machine to afford 8-((3,5-difluoro-4-methoxybenzyl)thio)quinolone, SRI-37617 as a colorless solid in 95% yield (HPLC purity: 100%). ESI-MS m/z: 318.1. $^1$H NMR (400 MHz, DMSO-d6): δ 8.87 (dd, J=4.2, 1.7 Hz, 1H), 8.35 (dd, J=8.3, 1.8 Hz, 1H), 7.72 (dd, J=8.0, 1.4 Hz, 1H), 7.62-7.47 (m, 3H), 7.27 (d, J=9.4 Hz, 2H), 4.31 (s, 2H), 3.87 (s, 3H). HRMS calcd for $[C_{17}H_{13}F_2NOS+H]^+$: 318.07587, Found: 318.07552.

$BBr_3$ (0.315 ml, 0.315 mmol) was added to a solution of 8-((3,5-difluoro-4-methoxy benzyl)thio)quinoline (20 mg, 0.063 mmol) in dichloromethane (2 ml) at 0° C. under Argon atmosphere and the resulted reaction mixture was stirred at rt for overnight. The reaction mixture was diluted with water and extracted with $CH_2Cl_2$ (3 times) and the combined organic layer was dried over anhydrous $Na_2SO_4$. The filtrate was concentrated in vacuo and the crude product was purified on Teledyne Isco Combiflash® Rf purification machine to afford 2,6-difluoro-4-((quinolin-8-ylthio)methyl)phenol SRI-37618 as a colorless solid in 68% yield (HPLC purity: 99.2%). ESI-MS m/z: 318.1. $^1$H NMR (400 MHz, DMSO-d6): δ 10.14 (s, 1H), 8.87 (dd, J=4.2, 1.7 Hz, 1H), 8.34 (dd, J=8.3, 1.8 Hz, 1H), 7.71 (dd, J=8.0, 1.4 Hz, 1H), 7.62-7.44 (m, 3H), 7.24-7.06 (m, 2H), 4.25 (s, 2H). HRMS calcd for $[C_{16}H_{11}F_2NOS+H]^+$: 304.0602, Found: 304.0612.

7. Evaluation of Thioquinolinones

A list of compounds evaluated is shown in Table 1 below.

TABLE 1

| No. | Structure | $EC_{50}$ (μM) | $E_{max}$ | HPLC Purity (%) | HRMS |
|---|---|---|---|---|---|
| 1 37618 | (structure) | 0.43 | 154 | 99.2 | Calculated: 303.0529, Found: 303.0539 |
| 2 38637 | (structure) | 0.34 | 127 | 99.3 | Calculated: 267.0718, Found: 267.0722 |
| 3 38935 | (structure) | 0.2 | 83.7 | 99.3 | Calculated: 285.0624, Found: 285.0626 |

TABLE 1-continued
| No. | Structure | EC$_{50}$ (μM) | E$_{max}$ | HPLC Purity (%) | HRMS |
|---|---|---|---|---|---|
| 4 38936 | 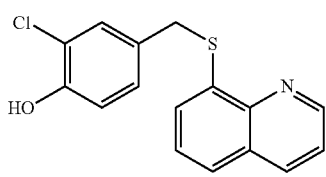 [SMILES: Oc1ccc(CSc2cccc3cccnc23)cc1Cl] | 0.34 | 106 | 98.9 | Calculated: 301.0328, Found: 301.0327 |
| 5 38934 | 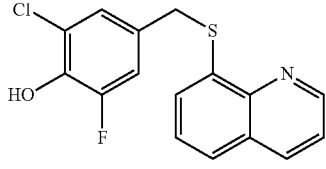 [SMILES: Oc1c(F)cc(CSc2cccc3cccnc23)cc1Cl] | 0.42 | 112.6 | 97.3 | Calculated: 319.0234, Found: 319.0231 |
| 6 38937 | 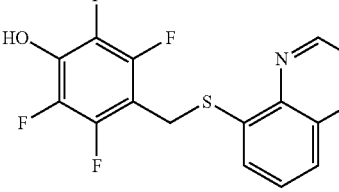 | 1.05 | 113.2 | 100 | Calculated: 339.0341, Found: 339.0345 |
| 7 39539 | 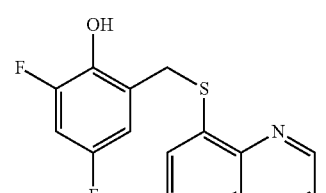 | 5.25 | 55.2 | 99.1 | Calculated: 303.0529, Found: 303.0533 |
| 8 38941 | 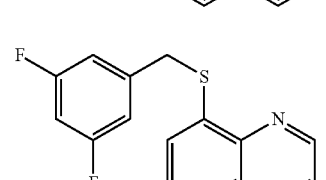 | Inactive | | 100 | Calculated: 287.0580, Found: 287.0579 |
| 9 40105 | 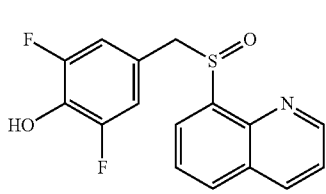 [SMILES: O=S(Cc1cc(F)c(O)c(F)c1)c1cccc2cccnc12] | 0.34 | 105.6 | 96.5 | Calculated: 319.0479, Found: 319.0478 |
| 10 38634 | 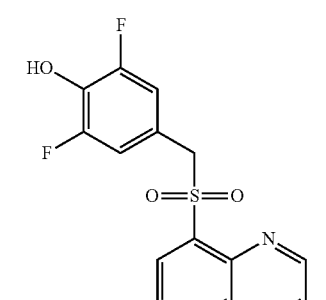 | Inactive | | 98.8 | Calculated: 335.0428, Found: 335.0430 |

TABLE 1-continued
| No. | Structure | EC$_{50}$ (μM) | E$_{max}$ | HPLC Purity (%) | HRMS |
|---|---|---|---|---|---|
| 11 39548 | 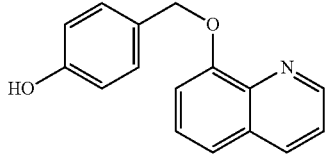 [SMILES: Oc1ccc(COc2cccc3cccnc23)cc1] | Inactive | | 100 | Calculated: 251.0946, Found: 251.0948 |
| 12 38942 | 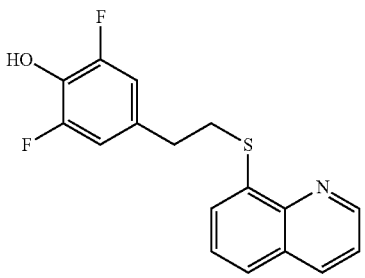 [SMILES: Oc1c(F)cc(CCSc2cccc3cccnc23)cc1F] | Inactive | | 98.4 | Calculated: 317.0686, Found: 317.0682 |
| 13 38943 | 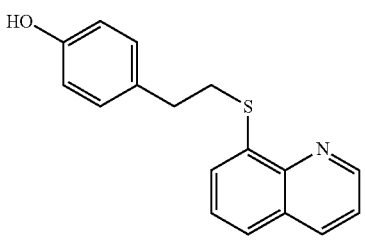 [SMILES: Oc1ccc(CCSc2cccc3cccnc23)cc1] | 19.02 | 121.8 | 98.4 | Calculated: 281.0874, Found: 281.0873 |
| 14 38933 | 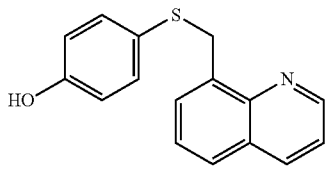 [SMILES: Oc1ccc(SCc2cccc3cccnc23)cc1] | Inactive | | 97.8 | Calculated: 267.0718, Found: 267.0712 |
| 15 38639 | 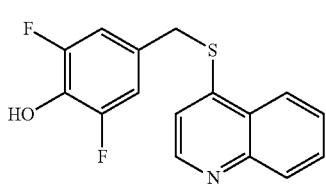 [SMILES: Oc1c(F)cc(CSc2ccnc3ccccc23)cc1F] | Inactive | | 98.9 | Calculated: 303.0529, Found: 303.0533 |
| 16 38638 | 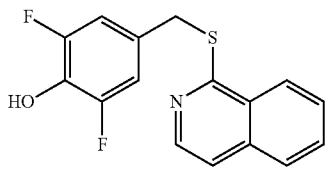 [SMILES: Oc1c(F)cc(CSc2nccc3ccccc23)cc1F] | Inactive | | 98.1 | Calculated: 303.0529, Found: 303.0520 |
| 17 38949 | 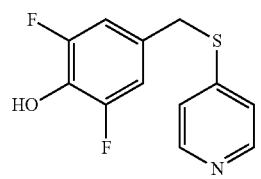 [SMILES: Oc1c(F)cc(CSc2ccncc2)cc1F] | Inactive | | 97.6 | Calculated: 253.0373, Found: 253.0373 |

TABLE 1-continued

| No. | Structure | EC$_{50}$ (μM) | E$_{max}$ | HPLC Purity (%) | HRMS |
|---|---|---|---|---|---|
| 18 38950 | 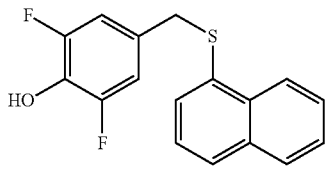 [SMILES: Oc1c(F)cc(CSc2cccc3ccccc23)cc1F] | Inactive | | 96.3 | Calculated: 302.0577, Found: 302.0571 |
| 19 37617 | 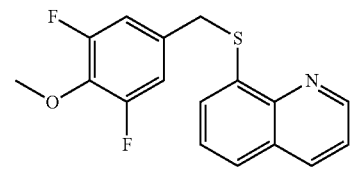 [SMILES: COc1c(F)cc(CSc2cccc3cccnc23)cc1F] | Inactive | | 100 | Calculated: 317.0686, Found: 317.0682 |
| 20 38939 | 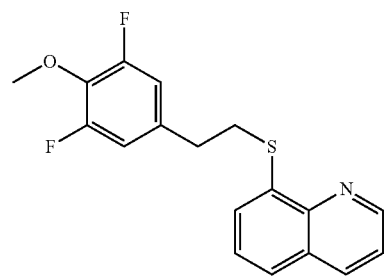 [SMILES: COc1c(F)cc(CCSc2cccc3cccnc23)cc1F] | 20 | 69.9 | 97.3 | Calculated: 331.0842, Found: 331.0843 |
| 21 38640 | 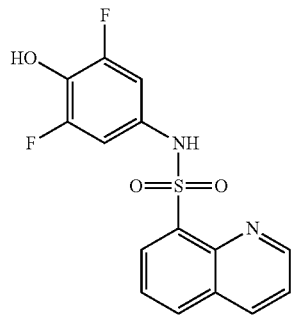 [SMILES: O=S(=O)(Nc1cc(F)c(O)c(F)c1)c1cccc2cccnc12] | Inactive | | 100 | Calculated: 336.038, Found: 336.088 |
| 22 38339 | 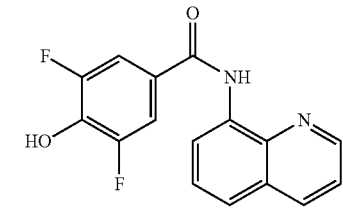 [SMILES: O=C(Nc1cccc2cccnc12)c1cc(F)c(O)c(F)c1] | Inactive | | 98.23 | Calculated: 300.0710, Found: 300.0707 |
| 23 38336 | 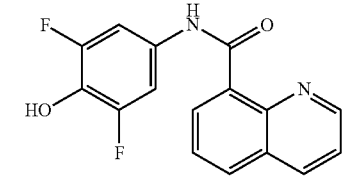 [SMILES: O=C(Nc1cc(F)c(O)c(F)c1)c1cccc2cccnc12] | Inactive | | 100 | Calculated: 300.0710, Found: 300.0705 |

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A compound having a structure represented by a formula:

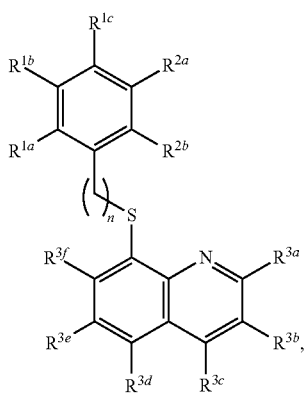

wherein n is 1 or 2;
wherein each of $R^{1a}$, $R^{1b}$, and $R^{1c}$ is independently selected from hydrogen, halogen, —CN, —NH$_2$, —OH, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl, provided that at least one of $R^{1a}$, $R^{1b}$, and $R^{1c}$ is —OH, C1-C4 alkoxy, or C1-C4 alkylamino;
wherein each of $R^{2a}$ and $R^{2b}$ is independently selected from hydrogen, halogen, —CN, —NH$_2$, —OH, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; and
wherein each of $R^{3a}$, $R^{3b}$, $R^{3c}$, $R^{3d}$, $R^{3e}$, and $R^{3f}$ is independently selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl,
provided that at least two of $R^{1a}$, $R^{1b}$, $R^{1c}$, $R^{2a}$, and $R^{2b}$ are non-hydrogen groups, and
provided that when n is 1, Z is —S—, and $R^{1a}$ is —OH or C1-C4 alkoxy, then exactly two of $R^{1a}$, $R^{1b}$, $R^{1c}$, $R^{2a}$, and $R^{2b}$ are non-hydrogen groups,
or a pharmaceutically acceptable salt thereof.

2. The compound of claim 1, wherein n is 1.

3. The compound of claim 1, wherein n is 2.

4. The compound of claim 1, wherein one of $R^{1a}$, $R^{1b}$, and $R^{1c}$ is —OH or C1-C4 alkoxy.

5. The compound of claim 1, wherein $R^{1c}$ is —OH or C1-C4 alkoxy.

6. The compound of claim 1, wherein $R^{1c}$ is —OH or —OMe.

7. The compound of claim 1, wherein one of $R^{1a}$, $R^{1b}$, and $R^{1c}$ is —OH or C1-C4 alkoxy, and two of $R^{1a}$, $R^{1b}$, and $R^{1c}$ are independently selected from hydrogen and halogen.

8. The compound of claim 1, wherein each of $R^{2a}$ and $R^{2b}$ is independently selected from hydrogen and halogen.

9. The compound of claim 1, wherein each of $R^{3a}$, $R^{3b}$, $R^{3c}$, $R^{3d}$, $R^{3e}$, and $R^{3f}$ is hydrogen.

10. The compound of claim 1, wherein the compound has a structure represented by a formula selected from:

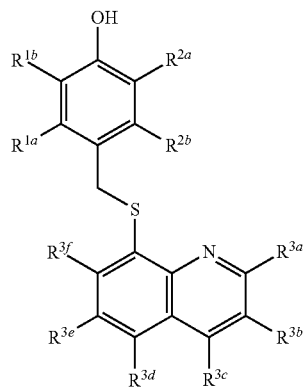

and

-continued
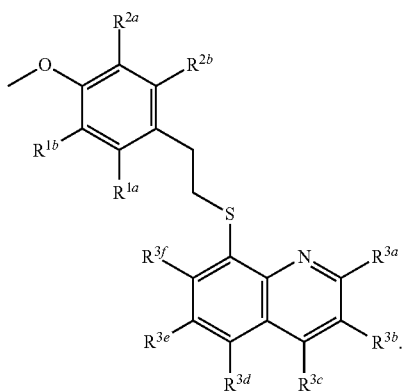
11. The compound of claim 1, wherein the compound has a structure represented by a formula selected from:
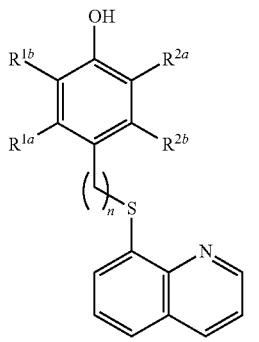
and
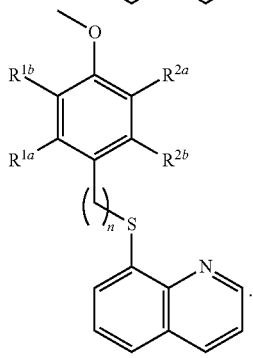
12. The compound of claim 1, wherein the compound is not:
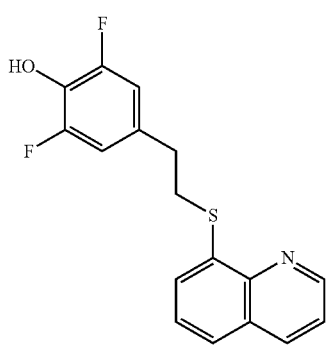
and
-continued
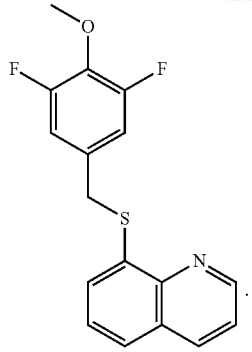
13. The compound of claim 1, wherein the compound is selected from:
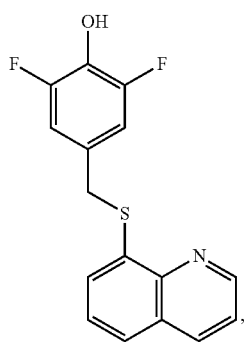 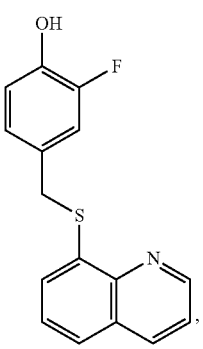
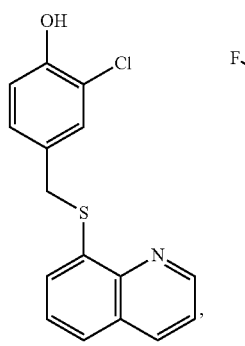 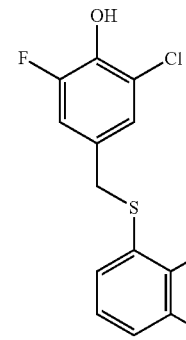
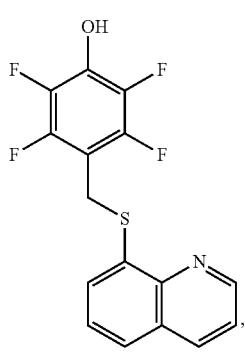 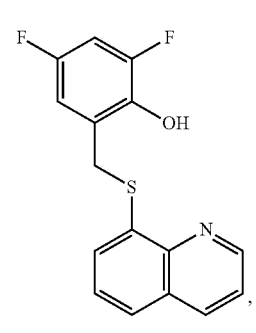
and -continued

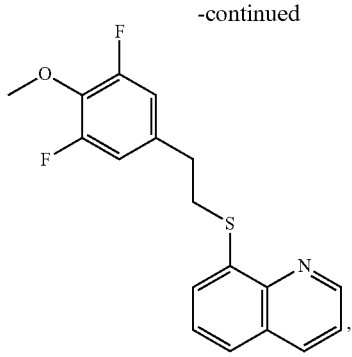

or a pharmaceutically acceptable salt thereof.

14. A pharmaceutical composition comprising a therapeutically effective amount of the compound of claim 1 and a pharmaceutically acceptable carrier.

15. A method for treating a disorder associated with heme oxygenase-1 (HO-1) signaling dysfunction, wherein the disorder associated with HO-1 is a kidney disease, in a subject in need thereof, the method comprising administering to the subject an effective amount of compound having a structure represented by a formula.

16. The method of claim 15, wherein the kidney disease is chronic kidney disease or acute kidney injury (AKI).

17. The method of claim 15, wherein the subject is a human.

18. A method for modifying HO-1 signaling in a subject, the method comprising administering to the subject an effective amount of compound having a structure represented by a formula:

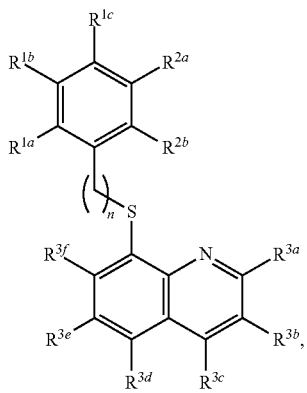

wherein n is 1 or 2;

wherein each of $R^{1a}$, $R^{1b}$, and $R^{1c}$ is independently selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl, provided that at least one of $R^{1a}$, $R^{1b}$, and $R^{1c}$ is —OH, C1-C4 alkoxy, or C1-C4 alkylamino;

wherein each of $R^{2a}$ and $R^{2b}$ is independently selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; and wherein each of $R^{3a}$, $R^{3b}$, $R^{3c}$, $R^{3d}$, $R^{3e}$, and $R^{3f}$ is independently selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl, or a pharmaceutically acceptable salt thereof, thereby modifying HO-1 signaling in the subject.

19. The method of claim 18, wherein modifying is activating.

* * * * *

UNITED STATES PATENT AND TRADEMARK OFFICE
CERTIFICATE OF CORRECTION

| | |
|---|---|
| PATENT NO. | : 11,623,918 B2 |
| APPLICATION NO. | : 17/529201 |
| DATED | : April 11, 2023 |
| INVENTOR(S) | : Mark J. Suto et al. |

It is certified that error appears in the above-identified patent and that said Letters Patent is hereby corrected as shown below:

In the Specification

Column 1, insert the following new paragraph after Line 10 but before the heading "REFERENCE TO THE SEQUENCE LISTING" on Line 12:
-- "STATEMENT REGARDING FEDERALLY SPONSORED RESEARCH
This invention was made with government support under grant number DK059600 awarded by the National Institutes of Health. The government has certain rights in the invention." --

Signed and Sealed this
Tenth Day of October, 2023

Katherine Kelly Vidal
*Director of the United States Patent and Trademark Office*